(12) United States Patent
Antle et al.

(10) Patent No.: US 9,493,582 B2
(45) Date of Patent: Nov. 15, 2016

(54) ALKYLATED CYCLODEXTRIN COMPOSITIONS AND PROCESSES FOR PREPARING AND USING THE SAME

(71) Applicant: Cydex Pharmaceuticals, Inc., La Jolla, CA (US)

(72) Inventors: Vincent D. Antle, Olathe, KS (US); Alvaro Lopes, Loures (PT); Daniel Monteiro, Loures (PT)

(73) Assignee: Cydex Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 14/381,568

(22) PCT Filed: Feb. 27, 2013

(86) PCT No.: PCT/US2013/028094
§ 371 (c)(1),
(2) Date: Aug. 27, 2014

(87) PCT Pub. No.: WO2013/130666
PCT Pub. Date: Sep. 6, 2013

(65) Prior Publication Data
US 2015/0045311 A1 Feb. 12, 2015

Related U.S. Application Data

(60) Provisional application No. 61/604,504, filed on Feb. 28, 2012.

(51) Int. Cl.
| | | |
|---|---|---|
| C08B 37/16 | (2006.01) |
| A61K 47/40 | (2006.01) |
| C08L 5/16 | (2006.01) |
| A61K 38/07 | (2006.01) |

(52) U.S. Cl.
CPC .......... *C08B 37/0012* (2013.01); *A61K 38/07* (2013.01); *A61K 47/40* (2013.01); *C08L 5/16* (2013.01)

(58) Field of Classification Search
None
See application file for complete search history.

(56) References Cited

U.S. PATENT DOCUMENTS

| | | |
|---|---|---|
| 2,744,938 A | 7/1952 | Urban |
| 3,426,011 A | 2/1969 | Parmerter et al. |
| 3,453,257 A | 7/1969 | Parmerter et al. |
| 3,453,259 A | 7/1969 | Parmerter et al. |
| 3,459,731 A | 8/1969 | Gramera et al. |
| 4,317,881 A | 3/1982 | Yagi et al. |
| 4,477,568 A | 10/1984 | Hokse et al. |
| 4,597,946 A | 7/1986 | Ward |
| 4,658,058 A | 4/1987 | Umezawa et al. |
| 4,738,923 A | 4/1988 | Ammeraal |
| 4,904,306 A | 2/1990 | Ammeraal |
| 4,920,214 A | 4/1990 | Friedman |
| 5,019,562 A | 5/1991 | Folkman et al. |
| 5,134,127 A | 7/1992 | Stella et al. |
| 5,173,481 A | 12/1992 | Pitha et al. |
| 5,183,809 A | 2/1993 | Weisz et al. |
| 5,241,059 A | 8/1993 | Yoshinaga |
| 5,324,718 A | 6/1994 | Loftsson |
| 5,376,537 A | 12/1994 | Orsan et al. |
| 5,376,645 A | 12/1994 | Stella et al. |
| 5,393,880 A | 2/1995 | Shieh et al. |
| 5,472,954 A | 12/1995 | Loftsson |
| 5,479,254 A | 12/1995 | Woskov et al. |
| 5,512,665 A | 4/1996 | Uchiyama et al. |
| 5,536,826 A | 7/1996 | Hirsenkorn |
| 5,550,222 A | 8/1996 | Shieh |
| 5,569,756 A | 10/1996 | Qi et al. |
| 5,578,719 A | 11/1996 | Gadelle et al. |
| 5,594,125 A | 1/1997 | Seyschab |
| 5,620,872 A | 4/1997 | Shieh et al. |
| 5,658,390 A | 8/1997 | Shieh et al. |
| 5,658,894 A | 8/1997 | Weisz et al. |
| 5,710,268 A | 1/1998 | Wimmer |
| 5,756,484 A | 5/1998 | Fuertes et al. |
| 5,760,015 A | 6/1998 | Joullie et al. |
| 5,831,081 A | 11/1998 | Reuscher |
| 5,846,954 A | 12/1998 | Joullie et al. |
| 5,874,418 A | 2/1999 | Stella et al. |
| 5,914,122 A | 6/1999 | Otterbeck et al. |
| 5,935,941 A | 8/1999 | Pitha |
| 6,033,573 A | 3/2000 | Toles et al. |
| 6,046,177 A | 4/2000 | Stella et al. |
| 6,133,248 A | 10/2000 | Stella |
| 6,153,746 A | 11/2000 | Shah et al. |

(Continued)

FOREIGN PATENT DOCUMENTS

| | | |
|---|---|---|
| EP | 0 579 435 | 1/1994 |
| EP | 1 067 143 | 1/2001 |
| EP | 1 950 227 | 7/2008 |
| EP | 2 018 866 | 1/2009 |
| JP | 04-57801 | 2/1992 |
| JP | 05-001102 | 1/1993 |

(Continued)

OTHER PUBLICATIONS

Yang et al., "Pharmacokinetics, Pharmacodynamics, Metabolism, Distribution, and Excretion of Carfilzomib in Rats" Drug Metabolism and Distribution (2011) vol. 39 No. 10 pp. 1873-1882.*

(Continued)

*Primary Examiner* — Eric Olson
(74) *Attorney, Agent, or Firm* — Knobbe Martens Olson & Bear LLP

(57) ABSTRACT

The present invention related to low-chloride alkylated cyclodextrin compositions, along with processes for preparing and using the same. The processes of the present invention provide alkylated cyclodextrins with low levels of drug-degrading agents and chloride.

64 Claims, 10 Drawing Sheets

(56) References Cited

U.S. PATENT DOCUMENTS

| | | |
|---|---|---|
| 6,235,505 B1 | 5/2001 | Grull et al. |
| 6,337,302 B1 | 1/2002 | Teng et al. |
| 6,407,079 B1 | 6/2002 | Muller et al. |
| 6,479,467 B1 | 11/2002 | Buchanan et al. |
| 6,524,595 B1 | 2/2003 | Perrier et al. |
| 6,610,671 B2 | 8/2003 | Buchanan et al. |
| 6,869,939 B2 | 3/2005 | Mosher et al. |
| 7,034,013 B2 | 4/2006 | Thompson et al. |
| 7,582,758 B2 | 9/2009 | Martin |
| 7,625,878 B2 | 12/2009 | Stella et al. |
| 7,629,331 B2 | 12/2009 | Pipkin et al. |
| 7,635,773 B2 | 12/2009 | Antle |
| 8,114,438 B2 | 2/2012 | Pipkin et al. |
| 8,236,782 B2 | 8/2012 | Mosher et al. |
| 8,410,077 B2 | 4/2013 | Antle |
| 8,492,538 B1 | 7/2013 | Matos |
| 2003/0055023 A1 | 3/2003 | Rajewski et al. |
| 2005/0164986 A1 | 7/2005 | Mosher et al. |
| 2005/0186267 A1 | 8/2005 | Thompson et al. |
| 2005/0250738 A1 | 11/2005 | Mosher et al. |
| 2002/0258537 | 11/2006 | Stella et al. |
| 2006/0258537 A1 | 11/2006 | Stella et al. |
| 2007/0020196 A1 | 1/2007 | Pipkin et al. |
| 2007/0020299 A1 | 1/2007 | Pipkin et al. |
| 2007/0175472 A1 | 8/2007 | Pipkin et al. |
| 2007/0202054 A1 | 8/2007 | Pipkin et al. |
| 2008/0194519 A1 | 8/2008 | Cloyd |
| 2009/0011037 A1 | 1/2009 | Pipkin et al. |
| 2009/0012042 A1 | 1/2009 | Ren et al. |
| 2009/0123540 A1 | 5/2009 | Pipkin et al. |
| 2009/0239942 A1 | 9/2009 | Cloyd |
| 2009/0270348 A1 | 10/2009 | Antle |
| 2010/0093663 A1 | 4/2010 | Antle |
| 2010/0292268 A1 | 11/2010 | Mosher et al. |
| 2012/0021013 A1 | 1/2012 | Esaki et al. |
| 2012/0136072 A1 | 5/2012 | Mosher et al. |
| 2013/0184357 A1 | 7/2013 | Antle |
| 2013/0331356 A1 | 12/2013 | Olhava et al. |

FOREIGN PATENT DOCUMENTS

| | | |
|---|---|---|
| JP | 05-504783 | 7/1993 |
| JP | 07-216002 | 8/1995 |
| JP | 10-504351 | 4/1998 |
| JP | 11-60610 | 3/1999 |
| JP | 2010-539193 | 12/2010 |
| WO | WO 90/12035 | 10/1990 |
| WO | WO 91/11172 | 8/1991 |
| WO | WO 99/42111 | 8/1999 |
| WO | WO 01/40316 | 6/2001 |
| WO | WO 02/055562 | 7/2002 |
| WO | WO 2005/042584 | 5/2005 |
| WO | WO 2005/118277 | 5/2005 |
| WO | WO 2006/071491 | 7/2006 |
| WO | WO 2008/005053 | 1/2008 |
| WO | WO 2008/005691 | 1/2008 |
| WO | WO 2008/005692 | 1/2008 |
| WO | WO 2008/005802 | 1/2008 |
| WO | WO 2008/005819 | 1/2008 |
| WO | WO 2008/034040 | 3/2008 |
| WO | WO 2008/135601 | 11/2008 |
| WO | WO 2009/018069 | 2/2009 |
| WO | WO 2009/045497 | 4/2009 |
| WO | WO 2009/134347 | 11/2009 |
| WO | WO 2010/053487 | 5/2010 |
| WO | WO 2013/123254 | 8/2013 |
| WO | WO 2014/066274 | 5/2014 |

OTHER PUBLICATIONS

U.S. Appl. No. 14/437,439, filed Apr. 2015, Antle et al.*
ISR and WO dated Apr. 19, 2013 in PCT/US13/028094.
Extended European Search Report dated Jun. 27, 2014 in European Application No. 13755899.5.

Adam et al., 2002, Cyclodextrin-derived host molecules as reversal agents for the neuromuscular blocker rocuronium bromide: synthesis and structure-activity relationships, J. Med. Chem. 45:1806-1816.
Baptista et al., 1996, Near-infrared detection of flow injection analysis by acoustooptic tunable filter-based spectrophotometry, Anal. Chem., 68(6):971-976.
Betadex, Jan.-Feb. 2008, Pharmacopeial Forum, The United States Pharmacopeial Convention, 34(1):127-130.
Comprehensive Supramolecular Chemistry, vol. 3 Cyclodextrins, Szejtli et al., eds., Elsevier Science Inc., Tarrytown, NY, 1996.
Connors et al., eds., Chemical Stability of Pharmaceuticals, 1st Ed., John Wiley & Sons, New York, 1979, pp. 134-135.
Connors et al., eds., Chemical Stability of Pharmaceuticals, 2nd Ed., John Wiley & Sons, New York, 1986, pp. 564-565, 584-565, 770-771, 776-779.
Crowley et al., Drug-Excipient Interactions, Pharmaceutical Technology, Mar. 2001, pp. 1-6, Advanstar Publication.
Cyclodextrins in Pharmacy, Fromming et al., eds., Kluwer Academic Publishiing, Dordrecht, Netherlands, 1994.
Norit Americas Inc., Jul. 2007, DARCO® KB-G Powdered Activated Carbon Product Datasheet, 2 pp.
Fridriksdottir et al., 1997, Formulation and testing of methazolamide cyclodextrin eye drop solutions, Journal of Controlled Release, 44(1):95-99.
Fridriksdottir et al., Jan. 1996, Design and in vivo testing of 17β-estradiol HPβCD sublingual tablets, Die Pharmazie, 51(1):39-42.
Fridriksdottir et al., Mar. 31-Apr. 2, 1996, Solubilization of β-cyclodextrin: the effect of polymers and various drugs on the solubility of β-cyclodextrin, Proceedings of the Eighth International Symposium on Cyclodextrins, eds. Szejtli et al., Budapest, 373-376.
Hughes et al., 2004, Array reactors for parallel synthesis, Journal of Combinatorial Chemistry, 6(3):308.
Jacquet et al., 2004, Liquid chromatography analysis of monosubstituted sulfobutyl ether-β-cyclodextrin isomers on porous graphitic carbon, J. Sep. Sci. 27(14):1221-1228.
Kristinsson et al., 1996, Dexamethasone-cyclodextrin-polymer co-complexes in aqueous eye drops, Investigative Ophthalmology & Visual Science, 37(6):1199-1203.
Lammers et al., 1971, Properties of cyclodextrins: Part VI. Water-soluble cyclodextrin-derivatives. Preparation and Analysis, Die Starke, 23(5):167-171.
Lammers et al., 1972, Properties of cyclodextrins, Part VIII Determination of the composition of inclusion complexes of hexane and 2,3-dimethylbutane with cyclodextrin derivatives in aqueous solution, Recl. Trav. Chim. Pays-Bas, 91(6):733-753.
Loftsson et al., 1994, The effect of polyvinylpyrrolidone and hydroxypropyl methylcellulose on HPβCD complexation of hydrocortisone and its permeability through hairless mouse skin, European Journal of Pharmaceutical Sciences, 2:297-301.
Lotfsson et al., 1994, The effect of water-soluble polymers on drug-cyclodextrin complexation, International Journal of Pharmaceutics (Netherlands), 110(2):169-177.
Loftsson et al., 1996, Effects of cyclodextrins and polymers on topical drug delivery to the eye—evaluations in humans, Proceedings of the 23rd International Symposium on Controlled Release of Bioactive Materials, pp. 453-454.
Lotfsson et al., 1996, The influence of water-soluble polymers and pH on hydroxypropyl-β-cyclodextrin complexation of drugs, Drug Development and Industrial Pharmacy, 22(5):401-405.
Loftsson et al., 1997, Cyclodextrins as pharmaceutical excipients, Pharm. Technol. Eur. 9(5):26-34.
Loftsson et al., 1997, Enhanced complexation efficiency of cyclodextrins, Pharmaceutical Research, 14(11):S203.
Loftsson et al., 1998, Cyclodextrin solubilization of ETH-615, a zwitterionic drug, Drug Development and Industrial Pharmacy, 24(4):365-370.
Loftsson et al., 1998, The effect of water-soluble polymers on the aqueous solubility and complexing abilities of β-cyclodextrin, International Journal of Pharmaceutics, 163(1-2):115-121.
Lotfsson et al., 1999, Methods to enhance the complexation efficiency of cyclodextrins, S.T.P. Pharma Sciences, 9(3):237-242.

(56) References Cited

OTHER PUBLICATIONS

Loftsson et al., 2001, Cyclodextrin solubilization of benzodiazepines: formulation of midazolam nasal spray, International Journal of Pharmaceutics, 212(1):29-40.
Loftsson et al., Apr. 11, 1994, The effect of hydroxypropyl methylcellulose on the release of dexamethasone from aqueous 2-hyroxypropyl-β-cyclodextrin formulations, International Journal of Pharmaceutics (Netherlands), 104:181-184.
Loftsson et al., Oct. 1994, Polymer-cyclodextrin-drug complexes, Pharmaceutical Research, 11(10):S225.
Loftsson et al., Oct. 1996, Pharmaceutical applications of cyclodextrins. 1. Drug solubilization and stabilization, Journal of Pharmaceutical Sciences, 85(10):1017-1025.
Loftsson et al., Sep. 16, 1996, Drug-cyclodextrin-polymer ternary complexes, European Journal of Pharmaceutical Sciences, 4(SUPPL):S144.
Loftsson et al., Sep. 1996, Solubilization of β-cyclodextrin, Eur. J. Pharm. Sci, 4(Suppl.):S143.
Loftsson et al., Sep. 2001, Sustained drug delivery system based on a cationic polymer and an anionic drug/cyclodextrin complex, Pharmazie, 56(9):746-747.
Lotfsson, 1996, Topically effective acetazolamide eye-drop solution in man, Pharmaceutical Sciences, 2(6):277-279.
Loftsson, 1998, Drug-cyclodextrin complexation in the presence of water soluble polymers: enhanced Loftsson, solubility and percutaneous transport, Abstracts of Papers Part 1, 216th ACS National Meeting, Boston, Aug. 23-27, CELL-016.
Loftsson, Apr. 2-6, 1995, The effect of polymers on cyclodextrin complexation, Book of Abstracts, 209th ACS National Meeting, 209(1):33-CELL.
Loftsson, Nov. 1988, Increasing the cyclodextrin complexation of drugs and drug biovailability through addition of water-soluble polymers, Pharmazie, 53(11):733-740.
Luna et al., 1997, Fractionation and characterization of 4-sulfobutyl ether derivatives of cyclomaltoheptaose (β-cyclodextrin), Carbohydrate Research, 299:103-110.
Malaekeh-Nikouei et al., May 16, 2009, Evaluation the effect of cyclodextrin complexation on aqueous solubility of fluorometholone to achieve ophthalmic solution, J Incl Phemon Macrocycl Chem, 6 pp.
Masson et al., 1999, Drug-cyclodextrin complexation in the presence of water-soluble polymers: enhanced solubility and percutaneous transport, ACS Symposium Series, 737 (Polysaccharide Applications), pp. 24-45.
Modified Cyclodextrins: Scaffolds and Templates for Supramolecular Chemistry, Easton et al. eds., Imperial College Press, London, UK, 1999.
Neunert et al., 2009, Glycosidic moiety changes the spectroscopic properties of DL-α-tocopherol in DMSO/water solution and in organic solvents, Molecular and biomolecular spectroscopy, Spectrochimica Acta Part A, 73:301-308.
New Trends in Cyclodextrins and Derivatives, Duchene ed., Editions de Sante, Parks, France, 1991.
Polymer Science, in Physical Pharmacy. Physical Chemical Principles in Pharmaceutical Sciences, 3rd edition, Martin et al., 1983, pp. 592-638.
Polymers and Macromolecules, in Physicochemical Principles of Pharmacy, 2nd edition, Florence et al., eds. pp. 281-334, 1988.

Qu et al., 2002, Sulfoalkyl ether β-cyclodextrin derivatives: synthesis and characterizations, J. Inclusion Phenom. Macro. Chem, 43:213-221.
Remington's Pharmaceutical Sciences, 18th Edition, Gennaro ed., 1990, Hydrophilic Dispersons, pp. 291-294.
Remington's Pharmaceutical Sciences, 18th Edition, Gennaro ed., 1990, Hydrophilic Dispersons, pp. 436-437.
Sandarusi et al., 1988, An automated flow calrimeter for heat capacity and enthalpy measurements, International Journal of Thermophysics, 9(6):993-1002.
Savolainen et al., 1998, Co-administration of a water-soluble polymer increases the usefulness of cyclodextrins in solid oral dosage forms, Pharmaceutical Research, 15(11):1696-1701.
Savolainen et al., May 31-Jun. 3, 1998, Coadministration of a water-soluble polymer increases the usefulness of cyclodextrins in solid oral dosage forms, 9th Proceedings of the International Symposium on Cyclodextrins, Santiago de Comostela, Spain, eds. Labandeira et al., pp. 261-264.
Sigurdardottir et al., Dec. 29, 1995, The effect of polyvinylpyrolidone on cyclodextrin complexation of hydrocortisone and its diffusion through hairless mouse skin, International Journal of Pharmaceutics (Netherlands), 126:73-78.
Sotthivirat et al., 2007, Evaluation of various properties of alternative salt forms of sulfobutylether-β-cyclodextrine, $(SBE)_{7M}$-β-CD, Int. J. Pharm. 330:73-81.
Stella, Mar. 31-Apr. 2, 1996, SBE7-β-CD, a new, novel and safe polyanionic β-cyclodextrin derivative: characterization and biomedical applications, Proceedings of the Eighth International Symposium on Cyclodextrins, Budapest, Hungary, pp. 471-476.
Szente et al., 1999, Highly soluble cyclodextrin derivatives: chemistry, properties, and trends in development, Advanced Drug Delivery Reviews 36:17-28.
Tarver et al., 2002, 2-O-substituted cyclodextrins as reversal agents for the neuromuscular blocker rocuronium bromide, Bioorganic & Medicinal Chemistry, 10:1819-1827.
The Handbook of Pharmaceutical Excipients, 5th Ed., Rowe et al., eds., The Pharmaceutical Press and American Pharmacists Association, London, UK and Washington, DC (2006).
Third European Congress of Pharmaceutical Sciences, Edinburgh, Scotland, UK, Sep. 15-17, 1996.
Tongiani et al., 2005, Sulfoalkyl ether-alkyl ether-cyclodextrin derivatives, their synthesis, NMR characterization, and binding of 6α-methylprednisolone, J. Pharm. Sci., 94(11):2380-2392.
Vegvari et al., 2000, A new easy-to-prepare continuous electrochromatographic bed for enantiomer recogniation, Electrophoresis, 21:3116-3125.
Wenz et al., 1999, Synthesis of highly water-soluble cyclodextrin sulfonates by addition of hydrogen sulfite to cyclodextrin allyl ethers, Carbohydr. Res. 322:153-165.
Wittung et al., 1994, Absorption flattening in the optical spectra of liposome-entrapped substances, FEBS Letters 352:37-40.
Blanchard et al., 1999, Some important considerations in the use of cyclodextrins, Pharmaceutical Research, 16(12):1796-1798.
Luna et al., 1996 Evaluation of the utility of capillary electrophoresis for the analysis of sulfobutyl ether β-cyclodextrin mixtures, J. Pharmaceutical and Biomedical Analysis 15:63-71.
Luna et al., 1996, Characterization of sulfobutyl ether β-cyclodextrin mixtures, Proceedings of the Eighth International Symposium on Cyclodextrins 133-136.

* cited by examiner

ALKYLATED CYCLODEXTRIN COMPOSITIONS AND PROCESSES FOR PREPARING AND USING THE SAME

RELATED APPLICATIONS

This application is the U.S. National Phase under 35 U.S.C. §371 of International Application No. PCT/US2013/028094, filed on Feb. 27, 2013, designating the U.S. and published in English as WO 2013/130666, which claims the benefit of U.S. Provisional Application No. 61/604,504, filed, Feb. 28, 2012, both of which are incorporated by reference herein in their entirety, including any drawings.

BACKGROUND OF THE INVENTION

1. Field of the Invention

The present invention relates to compositions comprising low-chloride alkylated cyclodextrin compositions, and processes for preparing and using the same.

2. Background of the Invention

Hydrophobic, hydrophilic, polymerized, ionized, non-ionized and many other derivatives of cyclodextrins have been developed, and their use in various industries has been established. Generally, cyclodextrin derivatization proceeds via reactions in which —OH groups at the 2-, 3-, and/or 6-position of the amylose rings of a cyclodextrin are replaced with substituent groups. Substituents include neutral, anionic and/or cationic functional groups.

Known cyclodextrin derivatives such as alkylated cyclodextrins include, but are not limited to, sulfoalkyl ether cyclodextrins, alkyl ether cyclodextrins (e.g., methyl, ethyl and propyl ether cyclodextrins), hydroxyalkyl cyclodextrins, thioalkyl ether cyclodextrins, carboxylated cyclodextrins (e.g., succinyl-β-cyclodextrin, and the like), sulfated cyclodextrins, and the like. Alkylated cyclodextrins having more than one type of functional group are also known, such as sulfoalkyl ether-alkyl ether-cyclodextrins (see, e.g., WO 2005/042584 and US 2009/0012042, each of which is hereby incorporated by reference in its entirety). In particular, alkylated cyclodextrins having 2-hydroxypropyl groups and/or sulfoalkyl ether groups have found use in pharmaceutical formulations.

A sulfobutyl ether derivative of β-cyclodextrin ("SBE-β-CD") has been commercialized by CyDex Pharmaceuticals, Inc. as Captisol® and Advasep®. The anionic sulfobutyl ether substituent improves the aqueous solubility and safety of the parent β-cyclodextrin, which can reversibly form complexes with active pharmaceutical agents, thereby increasing the solubility of active pharmaceutical agents and, in some cases, increase the stability of active pharmaceutical agents in aqueous solution. Captisol® has a chemical structure according to Formula X:

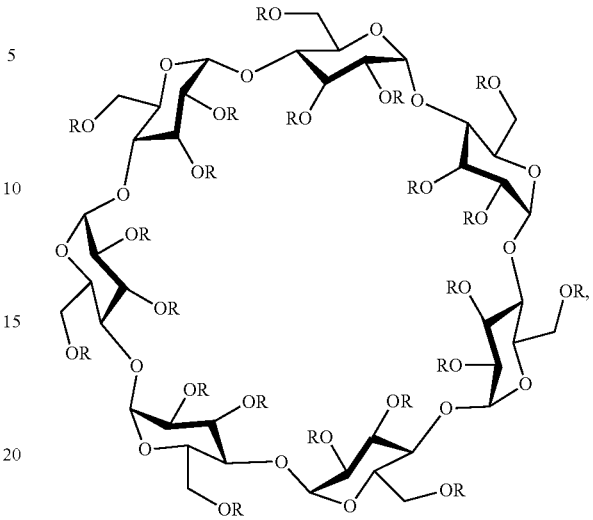

where R is $(-H)_{21-n}$ or $((-CH_2)_4-SO_3^-Na^+)_n$, and n is 6 to 7.1.

Sulfoalkyl ether derivatized cyclodextrins (such as Captisol®) are prepared using batch methods as described in, e.g., U.S. Pat. Nos. 5,134,127, 5,376,645 and 6,153,746, each of which is hereby incorporated by reference in its entirety.

Sulfoalkyl ether cyclodextrins and other derivatized cyclodextrins can also be prepared according to the methods described in the following patents and published patent applications: U.S. Pat. No. 3,426,011, U.S. Pat. No. 3,453,257, U.S. Pat. No. 3,453,259, U.S. Pat. No. 3,459,731, U.S. Pat. No. 4,638,058, U.S. Pat. No. 4,727,06, U.S. Pat. No. 5,019,562, U.S. Pat. No. 5,173,481, U.S. Pat. No. 5,183,809, U.S. Pat. No. 5,241,059, U.S. Pat. No. 5,536,826, U.S. Pat. No. 5,594,125, U.S. Pat. No. 5,658,894, U.S. Pat. No. 5,710,268, U.S. Pat. No. 5,756,484, U.S. Pat. No. 5,760,015, U.S. Pat. No. 5,846,954, U.S. Pat. No. 6,407,079, U.S. Pat. No. 7,625,878, U.S. Pat. No. 7,629,331, U.S. Pat. No. 7,635,773, US2009/0012042, JP 05001102, and WO 01/40316, as well as in the following non-patent publications: Lammers et al., Recl. Tray. Chim. Pays-Bas 91:733 (1972); Staerke 23:167 (1971), Adam et al., J. Med. Chem. 45:1806 (2002), Qu et al., J. Inclusion Phenom. Macrocyclic Chem. 43:213 (2002), Tarver et al., Bioorg. Med. Chem. 10:1819 (2002), Fromming et al., Cyclodextrins in Pharmacy (Kluwer Academic Publishing, Dordrecht, 1994), Modified Cyclodextrins: Scaffolds and Templates for Supramolecular Chemistry (C. J. Easton et al. eds., Imperial College Press, London, UK, 1999), New Trends in Cyclodextrins and Derivatives (Dominique Duchene ed., Editions de Sante, Paris, FR, 1991), Comprehensive Supramolecular Chemistry 3 (Elsevier Science Inc., Tarrytown, N.Y.), the entire disclosures of which are hereby incorporated by reference.

Impurities present in an alkylated cyclodextrin composition can reduce the shelf-life and potency of an active agent composition. Impurities can be removed from an alkylated cyclodextrin composition by exposure to (e.g., mixing with) activated carbon. The treatment of cyclodextrin-containing aqueous solutions and suspensions with activated carbon is known. See, e.g., U.S. Pat. Nos. 4,738,923, 5,393,880, and 5,569,756. However, there is a continued need for alkylated cyclodextrin compositions with higher purity.

BRIEF SUMMARY OF THE INVENTION

The present invention provides a process for preparing an alkylated cyclodextrin composition comprising an alkylated cyclodextrin, the process comprising: (a) mixing a cyclodextrin with an alkylating agent to form a reaction milieu comprising an alkylated cyclodextrin, one or more unwanted components, and one or more drug-degrading impurities; (b) conducting one or more separations to remove the one or more unwanted components from the reaction milieu to form a partially purified solution comprising the alkylated cyclodextrin and the one or more drug-degrading impurities, wherein the one or more separations are ultrafiltration, diafiltration, centrifugation, extraction, solvent precipitation, or dialysis; and (c) treating the partially purified solution with a phosphate-free activated carbon having a residual conductivity of 10 μS or less and producing the alkylated cyclodextrin.

In some embodiments, the alkylated cyclodextrin composition further comprises less than 500 ppm of a phosphate. In some embodiments, the alkylated cyclodextrin composition further comprises less than 125 ppm of a phosphate.

In some embodiments, the residual conductivity of the phosphate-free activated carbon is 9 μS or less. In some embodiments, the residual conductivity of the phosphate-free activated carbon is 8 μS or less.

In some embodiments, the alkylated cyclodextrin composition further comprises less than 0.5% (w/w) of a chloride. In some embodiments, the alkylated cyclodextrin composition further comprises less than 0.1% (w/w) of a chloride. In some embodiments, the alkylated cyclodextrin composition further comprises less than 0.05% (w/w) of a chloride.

In some embodiments, the alkylated cyclodextrin composition has an average degree of substitution of 2 to 9. In some embodiments, the alkylated cyclodextrin composition has an average degree of substitution of 4.5 to 7.5. In some embodiments, the alkylated cyclodextrin composition has an average degree of substitution of 6 to 7.5.

In some embodiments, the alkylated cyclodextrin composition has an absorption of less than 1 A.U., as determined by UV/vis spectrophotometry at a wavelength of 245 nm to 270 nm for an aqueous solution containing 300 mg of the alkylated cyclodextrin composition per mL of solution in a cell having a 1 cm path length. In some embodiments, said absorption of less than 1 A.U. is due to a drug degrading agent.

In some embodiments, the alkylated cyclodextrin composition has an absorption of less than 0.5 A.U., as determined by UV/vis spectrophotometry at a wavelength of 245 nm to 270 nm for an aqueous solution containing 300 mg of the alkylated cyclodextrin composition per mL of solution in a cell having a 1 cm path length. In some embodiments, said absorption of less than 0.5 A.U. is due to a drug degrading agent.

In some embodiments, the absorption is determined by UV/vis spectrophotometry at a wavelength of 245 nm to 270 nm for an aqueous solution containing 500 mg of the SAE-CD composition per mL of solution in a cell having a 1 cm path length.

In some embodiments, the alkylated cyclodextrin composition has an absorption of less than 1 A.U., as determined by UV/vis spectrophotometry at a wavelength of 320 nm to 350 nm for an aqueous solution containing 300 mg of the alkylated cyclodextrin composition per mL of solution in a cell having a 1 cm path length. In some embodiments, said absorption of less than 1 A.U. is due to a color forming agent.

In some embodiments, the alkylated cyclodextrin composition has an absorption of less than 0.5 A.U., as determined by UV/vis spectrophotometry at a wavelength of 320 nm to 350 nm for an aqueous solution containing 300 mg of the alkylated cyclodextrin composition per mL of solution in a cell having a 1 cm path length. In some embodiments, said absorption of less than 0.5 A.U. is due to a color forming agent.

In some embodiments, the absorption is determined by UV/vis spectrophotometry at a wavelength of 320 nm to 350 nm for an aqueous solution containing 500 mg of the alkylated cyclodextrin composition per mL of solution in a cell having a 1 cm path length.

In some embodiments, the phosphate-free activated carbon is washed with a solvent until the eluted solvent has reached the residual conductivity in (c). In some embodiments, the phosphate-free activated carbon is washed with water until the eluted water has reached the residual conductivity in (c).

In some embodiments, the alkylated cyclodextrin is a sulfoalkyl ether cyclodextrin of Formula (II):

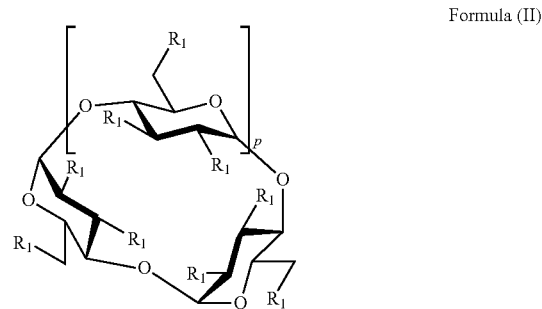

Formula (II)

wherein p is 4, 5, or 6, and $R_1$ is independently selected at each occurrence from —OH or —O—($C_2$-$C_6$ alkylene)-$SO_3^-$-T, wherein T is independently selected at each occurrence from pharmaceutically acceptable cations, provided that at least one $R_1$ is —OH and at least one $R_1$ is O—($C_2$-$C_6$ alkylene)-$SO_3^-$-T. In some embodiments, $R_1$ is independently selected at each occurrence from —OH or —O—($C_4$ alkylene)-$SO_3^-$-T, and -T is $Na^+$ at each occurrence.

In some embodiments, the alkylated cyclodextrin composition is combined with one or more excipients.

In some embodiments, the alkylated cyclodextrin composition is combined with an active agent.

The present invention is also directed to products prepared by the processes described herein.

Further embodiments, features, and advantages of the present inventions, as well as the composition, structure, and operation of various embodiments of the present invention, are described in detail below with reference to the accompanying drawings.

BRIEF DESCRIPTION OF THE DRAWINGS

The accompanying drawings, which are incorporated herein and form a part of the specification, illustrate one or more embodiments of the present invention and, together with the description, further serve to explain the principles of the invention and to enable a person skilled in the pertinent art to make and use the invention. The following drawings are given by way of illustration only, and thus are not intended to limit the scope of the present invention.

DETAILED DESCRIPTION OF THE INVENTION

Figure 1:
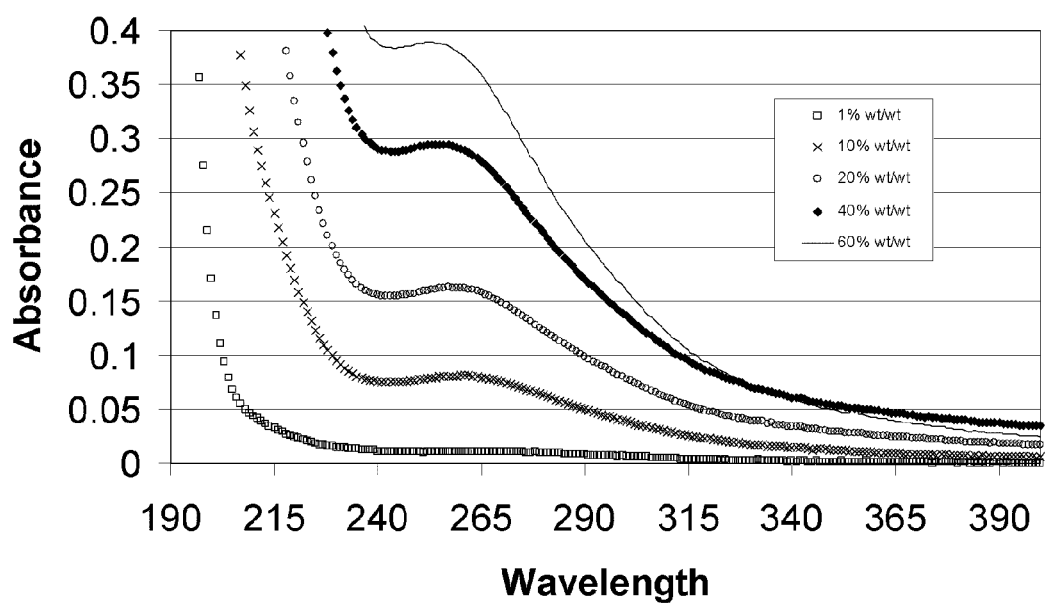
FIG. 1 provides a graphic representation of a UV/vis scan (190 nm to 400 nm) of solutions containing a SAE-CD composition after a single carbon treatment, in which the sulfoalkyl ether cyclodextrin concentration is varied from 1% to 60% by weight.

The invention includes combinations and sub-combinations of the various aspects and embodiments disclosed herein. Further, when a particular feature, structure, or characteristic is described in connection with an embodiment, it is understood that it is within the knowledge of one skilled in the art to affect such feature, structure, or characteristic in connection with other embodiments whether or not explicitly described. These and other aspects of this invention will be apparent upon reference to the following detailed description, examples, claims and attached figures.

As used herein, percentages refer to "% by weight" and/or "w/w" (weight by weight concentration) unless otherwise indicated.

References to spatial descriptions (e.g., "above," "below," "up," "down," "top," "bottom," etc.) made herein are for purposes of description and illustration only, and should be interpreted as non-limiting upon the processes, equipment, compositions and products of any method of the present invention, which can be spatially arranged in any orientation or manner.

Alkylated Cyclodextrin

An "alkylated cyclodextrin composition" is a composition comprising alkylated cyclodextrins having a degree of substitution or an average degree of substitution (ADS) for a specified substituent. An alkylated cyclodextrin composition comprises a distribution of alkylated cyclodextrin species differing in the individual degree of substitution specified substituent for each species, wherein the specified substituent for each species is the same. As used herein, an "alkylated cyclodextrin composition" is a substantially pharmaceutically inactive composition (i.e., a composition which does not contain a pharmaceutically active agent). For example, a cyclodextrin composition may comprise at least 90% (w/w) cyclodextrin, at least 95% (w/w) cyclodextrin, at least 97% (w/w) cyclodextrin, at least 99% (w/w) cyclodextrin, at least 99.9% (w/w) cyclodextrin, or at least 99.99% (w/w) cyclodextrin.

The alkylated cyclodextrin can be a water soluble alkylated cyclodextrin, which is any alkylated cyclodextrin exhibiting enhanced water solubility over its corresponding underivatized parent cyclodextrin and having a molecular structure based upon α-, β- or γ-cyclodextrin. In some embodiments, a derivatized cyclodextrin prepared by a process of the present invention has a solubility in water of 100 mg/mL or higher, or a solubility in water of less than 100 mg/mL.

The cyclodextrin can be derivatized with neutral, anionic or cationic substituents at the C2, C3, or C6 positions of the individual saccharides forming the cyclodextrin ring. Suitable water soluble alkylated cyclodextrins are described herein. The alkylated cyclodextrin can also be a water insoluble alkylated cyclodextrin or a alkylated cyclodextrin possessing a lower water solubility than its corresponding underivatized parent cyclodextrin.

As used herein, a "substituent precursor" or "alkylating agent" refers to a compound, reagent, moiety, or substance capable of reacting with an —OH group present on a cyclodextrin. In some embodiments, the derivatized cyclodextrin includes a substituent such as a sulfoalkyl ether group, an ether group, an alkyl ether group, an alkenyl ether group, a hydroxyalkyl ether group, a hydroxyalkenyl ether group, a thioalkyl ether group, an aminoalkyl ether group, a mercapto group, an amino group, an alkylamino group, a carboxyl group, an ester group, a nitro group, a halo group, an aldehyde group, a 2,3-epoxypropyl group, and combinations thereof. In some embodiments, alkylating agents include an alkyl sultone (e.g., 1,4-butane sultone, 1,5-pentane sultone, 1,3-propane sultone, and the like). An alkylated cyclodextrin is a cyclodextrin in which one or more —OH groups is replaced with an —O—R group, wherein the R contains an alkyl moiety. For example, the —O—R group can be an alkyl ether or a sulfoalkyl ether.

In some embodiments, alkylated cyclodextrins such as mixed ether alkylated cyclodextrins include, by way of example, those listed Table 1 below.

TABLE 1

| Mixed ether CD derivative | Mixed ether CD derivative | Mixed ether CD derivative |
|---|---|---|
| Sulfobutyl-hydroxybutyl-CD (SBE-HBE-CD) | Sulfopropyl-hydroxybutyl-CD (SPE-HBE-CD) | Sulfoethyl-hydroxybutyl-CD (SEE-HBE-CD) |
| Sulfobutyl-hydroxypropyl-CD (SBE-HPE-CD) | Sulfopropyl-hydroxypropyl-CD (SPE-HPE-CD) | Sulfoethyl-hydroxypropyl-CD (SEE-HPE-CD) |
| Sulfobutyl-hydroxyethyl-CD (SBE-HEE-CD) | Sulfopropyl-hydroxyethyl-CD (SPE-HEE-CD) | Sulfoethyl-hydroxyethyl-CD (SEE-HEE-CD) |
| Sulfobutyl-hydroxybutenyl-CD (SBE-HBNE-CD) | Sulfopropyl-hydroxybutenyl-CD (SPE-HBNE-CD) | Sulfoethyl-hydroxybutenyl-CD (SEE-HBNE-CD) |
| Sulfobutyl-ethyl (SBE-EE-CD) | Sulfopropyl-ethyl (SPE-EE-CD) | Sulfoethyl-ethyl (SEE-EE-CD) |
| Sulfobutyl-methyl (SBE-ME-CD) | Sulfopropyl-methyl (SPE-ME-CD) | Sulfoethyl-methyl (SEE-ME-CD) |
| Sulfobutyl-propyl (SBE-PE-CD) | Sulfopropyl-propyl (SPE-PE-CD) | Sulfoethyl-propyl (SEE-PE-CD) |
| Sulfobutyl-butyl (SBE-BE-CD) | Sulfopropyl-butyl (SPE-BE-CD) | Sulfoethyl-butyl (SEE-BE-CD) |
| Sulfobutyl-carboxymethyl-CD (SBE-CME-CD) | Sulfopropyl-carboxymethyl-CD (SPE-CME-CD) | Sulfoethyl-carboxymethyl-CD (SEE-CME-CD) |
| Sulfobutyl-carboxyethyl-CD (SBE-CEE-CD) | Sulfopropyl-carboxyethyl-CD (SPE-CEE-CD) | Sulfoethyl-carboxyethyl-CD (SEE-CEE-CD) |
| Sulfobutyl-acetate-CD (SBE-AA-CD) | Sulfopropyl-acetate-CD (SPE-AA-CD) | Sulfoethyl-acetate-CD (SEE-AA-CD) |
| Sulfobutyl-propionate-CD (SBE-PA-CD) | Sulfopropyl-propionate-CD (SPE-PA-CD) | Sulfoethyl-propionate-CD (SEE-PA-CD) |
| Sulfobutyl-butyrate-CD (SBE-BA-CD) | Sulfopropyl-butyrate-CD (SPE-BA-CD) | Sulfoethyl-butyrate-CD (SEE-BA-CD) |
| Sulfobutyl-methoxycarbonyl-CD (SBE-MC-CD) | Sulfopropyl-methoxycarbonyl-CD (SPE-MC-CD) | Sulfoethyl-methoxycarbonyl-CD (SEE-MC-CD) |
| Sulfobutyl-ethoxycarbonyl-CD (SBE-EC-CD) | Sulfopropyl-ethoxycarbonyl-CD (SPE-EC-CD) | Sulfoethyl-ethoxycarbonyl-CD (SEE-EC-CD) |
| Sulfobutyl-propoxycarbonyl-CD (SBE-PC-CD) | Sulfopropyl-propoxycarbonyl-CD (SPE-PC-CD) | Sulfoethyl-propoxycarbonyl-CD (SEE-PC-CD) |
| Hydroxybutyl-hydroxybutenyl-CD (HBE-HBNE-CD) | Hydroxypropyl-hydroxybutenyl-CD (HPE-HBNE-CD) | Hydroxyethyl-hydroxybutenyl-CD (HEE-HBNE-CD) |
| Hydroxybutyl-ethyl (HBE-EE-CD) | Hydroxypropyl-ethyl (HPE-EE-CD) | Hydroxyethyl-ethyl (HEE-EE-CD) |
| Hydroxybutyl-methyl (HBE-ME-CD) | Hydroxypropyl-methyl (HPE-ME-CD) | Hydroxyethyl-methyl (HEE-ME-CD) |
| Hydroxybutyl-propyl (HBE-PE-CD) | Hydroxypropyl-propyl (HPE-PE-CD) | Hydroxyethyl-propyl (HEE-PE-CD) |
| Hydroxybutyl-butyl (HBE-BE-CD) | Hydroxypropyl-butyl (HPE-BE-CD) | Hydroxyethyl-butyl (HEE-BE-CD) |
| Hydroxybutyl-carboxymethyl-CD (HBE-CME-CD) | Hydroxypropyl-carboxymethyl-CD (HPE-CME-CD) | Hydroxyethyl-carboxymethyl-CD (HEE-CME-CD) |
| Hydroxybutyl-carboxyethyl-CD (HBE-CEE-CD) | Hydroxypropyl-carboxyethyl-CD (HPE-CEE-CD) | Hydroxyethyl-carboxyethyl-CD (HEE-CEE-CD) |
| Hydroxybutyl-acetate-CD (HBE-AA-CD) | Hydroxypropyl-acetate-CD (HPE-AA-CD) | Hydroxyethyl-acetate-CD (HEE-AA-CD) |
| Hydroxybutyl-propionate-CD (HBE-PA-CD) | Hydroxypropyl-propionate-CD (HPE-PA-CD) | Hydroxyethyl-propionate-CD (HEE-PA-CD) |
| Hydroxybutyl-butyrate-CD (HBE-BA-CD) | Hydroxypropyl-butyrate-CD (HPE-BA-CD) | Hydroxyethyl-butyrate-CD (HEE-BA-CD) |
| Hydroxybutyl-methoxycarbonyl-CD (HBE-MC-CD) | Hydroxypropyl-methoxycarbonyl-CD (HPE-MC-CD) | Hydroxyethyl-methoxycarbonyl-CD (HEE-MC-CD) |
| Hydroxybutyl-ethoxycarbonyl-CD (HBE-EC-CD) | Hydroxypropyl-ethoxycarbonyl-CD (HPE-EC-CD) | Hydroxyethyl-ethoxycarbonyl-CD (HEE-EC-CD) |
| Hydroxybutyl-propoxycarbonyl-CD (HBE-PC-CD) | Hydroxypropyl-propoxycarbonyl-CD (HPE-PC-CD) | Hydroxyethyl-propoxycarbonyl-CD (HEE-PC-CD) |
| Hydroxybutenyl-ethyl (HBNE-EE-CD) | Hydroxypropenyl-ethyl (HPNE-EE-CD) | Hydroxypentenyl-ethyl (HPTNE-EE-CD) |
| Hydroxybutenyl-methyl (HBNE-ME-CD) | Hydroxypropenyl-methyl (HPNE-ME-CD) | Hydroxypentenyl-methyl (HPTNE-ME-CD) |
| Hydroxybutenyl-propyl (HBNE-PE-CD) | Hydroxypropenyl-propyl (HPNE-PE-CD) | Hydroxypentenyl-propyl (HPTNE-PE-CD) |
| Hydroxybutenyl-butyl (HBNE-BE-CD) | Hydroxypropenyl-butyl (HPNE-BE-CD) | Hydroxypentenyl-butyl (HPTNE-BE-CD) |
| Hydroxybutenyl-carboxymethyl-CD (HBNE-CME-CD) | Hydroxypropenyl-carboxymethyl-CD (HPNE-CME-CD) | Hydroxypentenyl-carboxymethyl-CD (HPTNE-CME-CD) |
| Hydroxybutenyl-carboxyethyl-CD (HBNE-CEE-CD)- | Hydroxypropenyl-carboxyethyl-CD (HPNE-CEE-CD) | Hydroxypentenyl-carboxyethyl-CD (HPTNE-CEE-CD) |
| Hydroxybutenyl-acetate-CD (HBNE-AA-CD) | Hydroxypropenyl-acetate-CD (HPNE-AA-CD) | Hydroxypentenyl-acetate-CD (HPTNE-AA-CD) |
| Hydroxybutenyl-propionate-CD (HBNE-PA-CD) | Hydroxypropenyl-propionate-CD (HPNE-PA-CD) | Hydroxypentenyl-propionate-CD (HPTNE-PA-CD) |
| Hydroxybutenyl-butyrate-CD (HBNE-BA-CD) | Hydroxypropenyl-butyrate-CD (HPNE-BA-CD) | Hydroxypentenyl-butyrate-CD (HPTNE-BA-CD) |
| Hydroxybutenyl-methoxycarbonyl-CD (HBNE-MC-CD) | Hydroxypropenyl-methoxycarbonyl-CD (HPNE-MC-CD) | Hydroxypentenyl-methoxycarbonyl-CD (HPTNE-MC-CD) |
| Hydroxybutenyl-ethoxycarbonyl-CD (HBNE-EC-CD) | Hydroxypropenyl-ethoxycarbonyl-CD (HPNE-EC-CD) | Hydroxypentenyl-ethoxycarbonyl-CD (HPTNE-EC-CD) |
| Hydroxybutenyl-propoxycarbonyl-CD (HBNE-PC-CD) | Hydroxypropenyl-propoxycarbonyl-CD (HPNE-PC-CD) | Hydroxypentenyl-propoxycarbonyl-CD (HPTNE-PC-CD) |

After reaction, purification, and/or isolation, the alkylated cyclodextrin composition of the present invention can comprise small amounts (e.g., 1% or less, 0.5% or less, 0.1% or less, 0.05% or less, 0.001% or less, 0.0005% or less, or 0.0001% or less, by weight) of a cyclodextrin starting material (e.g., an underivatized parent cyclodextrin).

The alkylated cyclodextrin can be present in high purity form. See U.S. Pat. No. 7,635,773. In some embodiments, the alkylated cyclodextrin is a high purity SAE-CD composition having a reduced amount of drug-degrading agent as compared to known commercial lots of Captisol®. The composition optionally has a reduced amount of phosphate or excludes phosphate entirely as compared to known commercial lots of Captisol®. The composition also optionally has lower amounts of a color-forming agent as compared to known commercial lots of Captisol®. The SAE-CD composition can also have reduced amounts of 1,4-butane sultone and 4-hydroxy-butane-1-sulfonic acid as compared to known commercial lots of Captisol®.

An alkylated cyclodextrin composition of the present invention provides unexpected advantages over other structurally related alkylated cyclodextrin compositions. By "structurally related" is meant, for example, that the substituent of the alkylated cyclodextrin in the composition is essentially the same as the substituent of the other alkylated cyclodextrin to which it is being compared. Exemplary advantages can include an enhanced purity, reduced content of pyrogens, reduced content of drug-degrading components, reduced content of color-forming agents, reduced content of unreacted substituent precursor, and/or reduced content of unreacted cyclodextrin starting material. An exemplary advantage also includes a reduced chloride content.

A water soluble alkylated cyclodextrin composition can comprise a sulfoalkyl ether cyclodextrin (SAE-CD) compound, or mixture of compounds, of the Formula I:

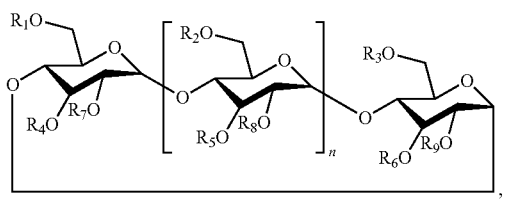

wherein: n is 4, 5 or 6; wherein $R_1$, $R_2$, $R_3$, $R_4$, $R_5$, $R_6$, $R_7$, $R_8$ and $R_9$ are independently —H, a straight-chain or branched $C_1$-$C_8$-(alkylene)-$SO_3^-$ group, or an optionally substituted straight-chain or branched $C_1$-$C_6$ group; wherein at least one of $R_1$, $R_2$, $R_3$, $R_4$, $R_5$, $R_6$, $R_7$, $R_8$ and $R_9$ is a straight-chain or branched $C_1$-$C_8$-(alkylene)-$SO_3^-$ group.

In some embodiments, a SAE-CD composition comprises a water-soluble alkylated cyclodextrin of Formula II:

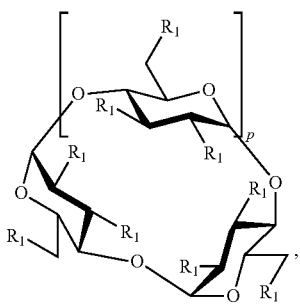

wherein: p is 4, 5 or 6;
$R_1$ is independently selected at each occurrence from —OH or -SAE-T;
-SAE- is a —O—($C_2$-$C_6$ alkylene)-$SO_3^-$ group, wherein at least one SAE is independently a —O—($C_2$-$C_6$ alkylene)-$SO_3^-$ group, a —O—$(CH_2)_g SO_3^-$ group, wherein g is 2 to 6, or 2 to 4, (e.g. —$OCH_2CH_2CH_2SO_3^-$ or —$OCH_2CH_2CH_2CH_2SO_3^-$); and -T is independently selected at each occurrence from the group consisting of pharmaceutically acceptable cations, which group includes, for example, $H^+$, alkali metals (e.g., $Li^+$, $Na^+$, $K^+$), alkaline earth metals (e.g., $Ca^{+2}$, $Mg^{+2}$), ammonium ions and amine cations such as the cations of ($C_1$-$C_6$)-alkylamines, piperidine, pyrazine, ($C_1$-$C_6$)-alkanolamine, ethylenediamine and ($C_4$-$C_8$)-cycloalkanolamine among others; provided that at least one $R_1$ is a hydroxyl moiety and at least one $R_1$ is -SAE-T.

When at least one $R_1$ of a derivatized cyclodextrin molecule is -SAE-T, the degree of substitution, in terms of the -SAE-T moiety, is understood to be at least one (1). When the term -SAE- is used to denote a sulfoalkyl-(alkylsulfonic acid)-ether moiety it being understood that the -SAE- moiety comprises a cation (-T) unless otherwise specified. Accordingly, the terms "SAE" and "-SAE-T" can, as appropriate, be used interchangeably herein.

Since SAE-CD is a poly-anionic cyclodextrin, it can be provided in different salt forms. Suitable counterions include cationic organic atoms or molecules and cationic inorganic atoms or molecules. The SAE-CD can include a single type of counterion or a mixture of different counterions. The properties of the SAE-CD can be modified by changing the identity of the counterion present. For example, a first salt form of a SAE-CD composition can possess greater osmotic potential or greater water activity reducing power than a different second salt form of same SAE-CD.

In some embodiments, a sulfoalkyl ether cyclodextrin is complexed with one or more pharmaceutically acceptable cations selected from, e.g., $H^+$, alkali metals (e.g., $Li^+$, $Na^+$, $K^+$), alkaline earth metals (e.g., $Ca^{+2}$, $Mg^{+2}$), ammonium ions and amine cations such as the cations of ($C_1$-$C_6$)-alkylamines, piperidine, pyrazine, ($C_1$-$C_6$)-alkanolamine, ethylenediamine and ($C_4$-$C_8$)-cycloalkanolamine, and the like, and combinations thereof.

Further exemplary sulfoalkyl ether (SAE)-CD derivatives include:

TABLE 2

| $SAE_x$-α-CD | $SAE_x$-β-CD | $SAE_x$-γ-CD |
|---|---|---|
| (Sulfoethyl ether)$_x$-α-CD | (Sulfoethyl ether)$_x$-β-CD | (Sulfoethyl-ether)$_x$-γ-CD |
| (Sulfopropyl ether)$_x$-α-CD | (Sulfopropyl ether)$_x$-β-CD | (Sulfopropyl-ether)$_x$-γ-CD |
| (Sulfobutyl ether)$_x$-α-CD | (Sulfobutyl ether)$_x$-β-CD | (Sulfobutyl-ether)$_x$-γ-CD |
| (Sulfopentyl ether)$_x$-α-CD | (Sulfopentyl ether)$_x$-β-CD | (Sulfopentyl-ether)$_x$-γ-CD |
| (Sulfohexyl ether)$_x$-α-CD | (Sulfohexyl ether)$_x$-β-CD | (Sulfohexyl-ether)$_x$-γ-CD | wherein x denotes the average degree of substitution. In some embodiments, the alkylated cyclodextrins are formed as salts.

Various embodiments of a sulfoalkyl ether cyclodextrin include eicosa-O-(methyl)-6G-O-(4-sulfobutyl)-β-cyclodextrin, heptakis-O-(sulfomethyl)-tetradecakis-O-(3-sulfopropyl)-β-cyclodextrin, heptakis-O-[(1,1-dimethylethyl)dimethylsilyl]-tetradecakis-O-(3-sulfopropyl)-β-cyclodextrin, heptakis-O-(sulfomethyl)-tetradecakis-O-(3-sulfopropyl)-β-cyclodextrin, and heptakis-O-[(1,1-dimethylethyl)dimethylsilyl]-tetradecakis-O-(sulfomethyl)-β-cyclodextrin. Other known alkylated cyclodextrins containing a sulfoalkyl moiety include sulfoalkylthio and sulfoalkylthioalkyl ether derivatives such as octakis-(S-sulfopropyl)-octathio-γ-cyclodextrin, octakis-O-[3-[(2-sulfoethyl)thio]propyl]-β-cyclodextrin], and octakis-S-(2-sulfoethyl)-octathio-γ-cyclodextrin.

In some embodiments, an alkylated cyclodextrin composition of the present invention is a sulfoalkyl ether-β-cyclodextrin composition having an ADS of 2 to 9, 4 to 8, 4 to 7.5, 4 to 7, 4 to 6.5, 4.5 to 8, 4.5 to 7.5, 4.5 to 7, 5 to 8, 5 to 7.5, 5 to 7, 5.5 to 8, 5.5 to 7.5, 5.5 to 7, 5.5 to 6.5, 6 to 8, 6 to 7.5, 6 to 7.1, 6.5 to 7.1, 6.2 to 6.9, or 6.5 per alkylated cyclodextrin, and the remaining substituents are —H.

In some embodiments, the alkylated cyclodextrin is a compound of Formula III:

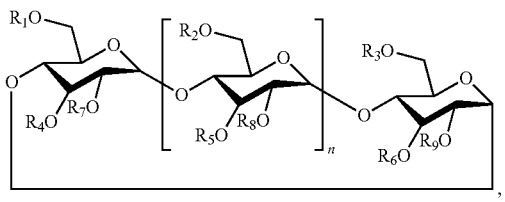

III wherein n is 4, 5 or 6, wherein $R_1$, $R_2$, $R_3$, $R_4$, $R_5$, $R_6$, $R_7$, $R_8$ and $R_9$ are independently selected from: —H, a straight-chain or branched $C_1$-$C_8$-(alkylene)-$SO_3^-$ group, and an optionally substituted straight-chain or branched $C_1$-$C_6$ group.

A water soluble alkylated cyclodextrin composition can comprise an alkyl ether (AE)-cyclodextrin compound, or mixture of compounds, of the Formula IV:

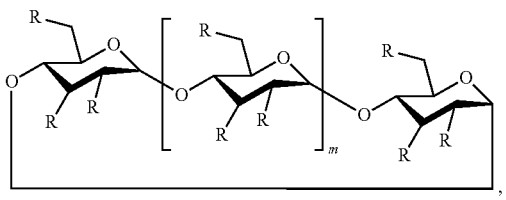

IV wherein: m is 4, 5 or 6; R is independently selected at each occurrence from the group consisting of —OH and AE; and AE is —O—($C_1$-$C_6$ alkyl); provided that at least one R is —OH; and at least one AE is present.

Further exemplary AE-CD derivatives include:

TABLE 3

| (Alkylether)$_y$-α-CD | (Alkylether)$_y$-β-CD | (Alkylether)$_y$-γ-CD |
|---|---|---|
| ME$_y$-α-CD | ME$_y$-β-CD | ME$_y$-γ-CD |
| EE$_y$-α-CD | EE$_y$-β-CD | EE$_y$-γ-CD |
| PE$_y$-α-CD | PE$_y$-β-CD | PE$_y$-γ-CD |
| BE$_y$-α-CD | BE$_y$-β-CD | BE$_y$-γ-CD |
| PtE$_y$-α-CD | PtE$_y$-β-CD | PtE$_y$-γ-CD |
| HE$_y$-α-CD | HE$_y$-β-CD | HE$_y$-γ-CD | wherein ME denotes methyl ether, EE denotes ethyl ether, PE denotes propyl ether, BE denotes butyl ether, PtE denotes pentyl ethyl, HE denotes hexyl ether, and y denotes the average degree of substitution.

A water soluble alkylated cyclodextrin composition can comprise a HAE-cyclodextrin compound, or mixture of compounds, of the Formula V:

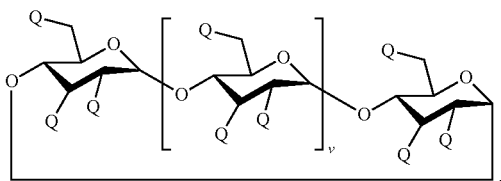

V wherein: "v" is 4, 5 or 6; "Q" is independently selected at each occurrence from the group consisting of —OH, and -HAE; and HAE is HO($C_1$-$C_6$ alkyl)-O—, provided that at least one -HAE moiety is present.

Further exemplary hydroxyalkyl ether (HAE)-CD derivatives include:

TABLE 4

| (HAE)$_z$-α-CD | (HAE)$_z$-β-CD | (HAE)$_z$-γ-CD |
|---|---|---|
| HMEz-α-CD | HMEz-β-CD | HMEz-γ-CD |
| HEEz-α-CD | HEEz-β-CD | HEEz-γ-CD |
| HPEz-α-CD | HPEz-β-CD | HPEz-γ-CD |
| HBEz-α-CD | HBEz-β-CD | HBEz-γ-CD |
| HPtEz-α-CD | HPtEz-β-CD | HPtEz-γ-CD |
| HHEz-α-CD | HHEz-β-CD | HHEz-γ-CD | wherein HME denotes hydroxymethyl ether, HEE denotes hydroxyethyl ether, HPE denotes hydroxypropyl ether, HBE denotes hydroxybutyl ether, HPtE denotes hydroxypentyl ether, HHE denotes hydroxyhexyl ether, and z denotes the average degree of substitution.

A water soluble alkylated cyclodextrin composition can comprise a SAE-AE-CD compound, or mixture of compounds, of Formula VI:

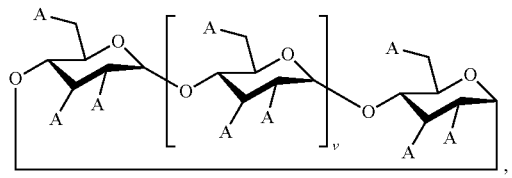

VI wherein: "v" is 4, 5 or 6; "A" is independently selected at each occurrence from the group consisting of —OH, -SAET and -AE; x is the degree of substitution for the SAET moiety and is 1 to 3v+5; y is the degree of substitution for the AE moiety and is 1 to 3v+5; -SAE is —O—($C_2$-$C_6$ alkylene)-$SO_3^-$; T is independently at each occurrence a cation; and AE is —O($C_1$-$C_3$ alkyl); provided that at least one -SAET moiety and at least one -AE moiety are present; and the sum of x, y and the total number of —OH groups in an alkylated cyclodextrin is 3v+6.

Specific embodiments of the derivatives of the present invention include those wherein: 1) the alkylene moiety of the SAE has the same number of carbons as the alkyl moiety of the AE; 2) the alkylene moiety of the SAE has a different number of carbons than the alkyl moiety of the AE; 3) the alkyl and alkylene moieties are independently selected from the group consisting of a straight chain or branched moiety; 4) the alkyl and alkylene moieties are independently selected from the group consisting of a saturated or unsaturated moiety; 5) the ADS for the SAE group is greater than or approximates the ADS for the AE group; or 6) the ADS for the SAE group is less than the ADS for the AE group.

A water soluble alkylated cyclodextrin composition can comprise a SAE-HAE-CD compound, or mixture of compounds, of Formula VII:

VII

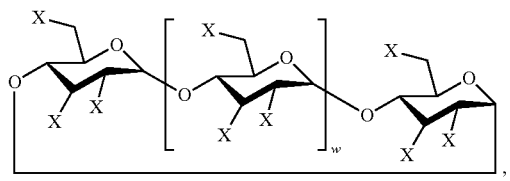

wherein: "v" is 4, 5 or 6; "X" is independently selected at each occurrence from the group consisting of —OH, SAET and HAE; x is the degree of substitution for the SAET moiety and is 1 to 3w+5; y is the degree of substitution for the HAE moiety and is 1 to 3w+5; -SAE is —O—($C_2$-$C_6$ alkylene)-$SO_3^-$; T is independently at each occurrence a cation; and HAE is HO—($C_1$-$C_6$ alkyl)-O—; provided that at least one -SAET moiety and at least one -HAE moiety are present; and the sum of x, y and the total number of —OH groups in an alkylated cyclodextrin is 3w+6.

The alkylated cyclodextrin can include SAE-CD, HAE-CD, SAE-HAE-CD, HANE-CD, HAE-AE-CD, HAE-SAE-CD, AE-CD, SAE-AE-CD, neutral cyclodextrin, anionic cyclodextrin, cationic cyclodextrin, halo-derivatized cyclodextrin, amino-derivatized cyclodextrin, nitrile-derivatized cyclodextrin, aldehyde-derivatized cyclodextrin, carboxylate-derivatized cyclodextrin, sulfate-derivatized cyclodextrin, sulfonate-derivatized cyclodextrin, mercapto-derivatized cyclodextrin, alkylamino-derivatized cyclodextrin, or succinyl-derivatized cyclodextrin.

Within a given alkylated cyclodextrin composition, the substituents of the alkylated cyclodextrin(s) thereof can be the same or different. For example, SAE or HAE moieties can have the same type or different type of alkylene (alkyl) radical upon each occurrence in an alkylated cyclodextrin composition. In such embodiments, the alkylene radical in the SAE or HAE moiety can be ethyl, propyl, butyl, pentyl or hexyl in each occurrence in an alkylated cyclodextrin composition.

The alkylated cyclodextrins can differ in their degree of substitution by functional groups, the number of carbons in the functional groups, their molecular weight, the number of glucopyranose units contained in the base cyclodextrin used to form the derivatized cyclodextrin and or their substitution patterns. In addition, the derivatization of a cyclodextrin with functional groups occurs in a controlled, although not exact manner. For this reason, the degree of substitution is actually a number representing the average number of functional groups per cyclodextrin (for example, $SBE_7$-β-CD has an average of 7 substitutions per cyclodextrin). Thus, it has an average degree of substitution ("ADS") of 7. In addition, the regiochemistry of substitution of the hydroxyl groups of the cyclodextrin is variable with regard to the substitution of specific hydroxyl groups of the hexose ring. For this reason, substitution of the different hydroxyl groups is likely to occur during manufacture of the derivatized cyclodextrin, and a particular derivatized cyclodextrin will possess a preferential, although not exclusive or specific, substitution pattern. Given the above, the molecular weight of a particular derivatized cyclodextrin composition can vary from batch to batch.

In a single parent cyclodextrin molecule, there are 3v+6 hydroxyl moieties available for derivatization. Where v=4 (α-cyclodextrin), "y" the degree of substitution for the moiety can range in value from 1 to 18. Where v=5 (β-cyclodextrin), "y" the degree of substitution for the moiety can range in value from 1 to 21. Where v=6 (γ-cyclodextrin), "y" the degree of substitution for the moiety can range in value from 1 to 24. In general, "y" also ranges in value from 1 to 3v+g, where g ranges in value from 0 to 5. In some embodiments, "y" ranges from 1 to 2v+g, or from 1 to 1v+g.

The degree of substitution ("DS") for a specific moiety (SAE, HAE or AE, for example) is a measure of the number of SAE (HAE or AE) substituents attached to an individual cyclodextrin molecule, in other words, the moles of substituent per mole of cyclodextrin. Therefore, each substituent has its own DS for an individual alkylated cyclodextrin species. The average degree of substitution ("ADS") for a substituent is a measure of the total number of substituents present per cyclodextrin molecule for the distribution of alkylated cyclodextrins within an alkylated cyclodextrin composition of the present invention. Therefore, $SAE_4$-CD has an ADS (per CD molecule) of 4.

Some embodiments of the present invention include those wherein: 1) more than half of the hydroxyl moieties of the alkylated cyclodextrin are derivatized; 2) half or less than half of the hydroxyl moieties of the alkylated cyclodextrin are derivatized; 3) the substituents of the alkylated cyclodextrin are the same upon each occurrence; 4) the substituents of the alkylated cyclodextrin comprise at least two different substituents; or 5) the substituents of the alkylated cyclodextrin comprise one or more of substituents selected from the group consisting of unsubstituted alkyl, substituted alkyl, halide (halo), haloalkyl, amine (amino), aminoalkyl, aldehyde, carbonylalkyl, nitrile, cyanoalkyl, sulfoalkyl, hydroxyalkyl, carboxyalkyl, thioalkyl, unsubstituted alkylene, substituted alkylene, aryl, arylalkyl, heteroaryl, and heteroarylalkyl.

Alkylated cyclodextrin compositions can comprise plural individual alkylated cyclodextrin species differing in individual degree of substitution, such that the average degree of substitution is calculated, as described herein, from the individual degrees of substitution of the species. More specifically, a SAE-CD derivative composition can comprise plural SAE-CD species each having a specific individual degree of substitution with regard to the SAE substituent. As a consequence, the ADS for SAE of a SAE-CD derivative composition represents an average of the IDS values of the population of individual molecules in the composition. For example, a $SAE_{5.2}$-CD composition comprises a distribution of plural $SAE_x$-CD molecules, wherein "x" (the DS for SAE groups) can range from 1 to 10-11 for individual cyclodextrin molecules; however, the population of SAE-cyclodextrin molecules is such that the average value for "x" (the ADS for SAE groups) is 5.2.

The alkylated cyclodextrin compositions can have a high to moderate to low ADS. The alkylated cyclodextrin compositions can also have a wide or narrow "span," which is the number of individual DS species within an alkylated cyclodextrin composition. For example, a alkylated cyclodextrin composition comprising a single species of alkylated cyclodextrin having a single specified individual DS is said to have a span of one, and the individual DS of the alkylated cyclodextrin equals the ADS of its alkylated cyclodextrin composition. An electropherogram, for example, of an alkylated cyclodextrin with a span of one should have only one alkylated cyclodextrin species with respect to DS. An alkylated cyclodextrin composition having a span of two comprises two individual alkylated cyclodextrin species differing in their individual DS, and its electropherogram, for example, would indicate two different alkylated cyclodextrin species differing in DS. Likewise, the span of an alkylated cyclodextrin composition having a span of three comprises three individual alkylated cyclodextrin species differing in their individual DS. The span of an alkylated cyclodextrin composition typically ranges from 5 to 15, or 7 to 12, or 8 to 11.

A parent cyclodextrin includes a secondary hydroxyl group on the C-2 and C-3 positions of the glucopyranose residues forming the cyclodextrin and a primary hydroxyl on the C-6 position of the same. Each of these hydroxyl moieties is available for derivatization by substituent precursor. Depending upon the synthetic methodology employed, the substituent moieties can be distributed randomly or in a somewhat ordered manner among the available hydroxyl positions. The regioisomerism of derivatization by the substituent can also be varied as desired. The regioisomerism of each composition is independently selected. For example, a majority of the substituents present can be located at a primary hydroxyl group or at one or both of the secondary hydroxyl groups of the parent cyclodextrin. In some embodiments, the primary distribution of substituents is C-3>C-2>C-6, while in other embodiments the primary distribution of substituents is C-2>C-3>C-6. Some embodiments of the present invention include an alkylated cyclodextrin molecule wherein a minority of the substituent moieties is located at the C-6 position, and a majority of the substituent moieties is located at the C-2 and/or C-3 position. Still other embodiments of the present invention include an alkylated cyclodextrin molecule wherein the substituent moieties are substantially evenly distributed among the C-2, C-3, and C-6 positions.

An alkylated cyclodextrin composition comprises a distribution of plural individual alkylated cyclodextrin species, each species having an individual degree of substitution ("IDS"). The content of each of the cyclodextrin species in a particular composition can be quantified using capillary electrophoresis. The method of analysis (capillary electrophoresis, for example, for charged alkylated cyclodextrins) is sufficiently sensitive to distinguish between compositions having only 5% of one alkylated cyclodextrin and 95% of another alkylated cyclodextrin from starting alkylated cyclodextrin compositions containing.

The above-mentioned variations among the individual species of alkylated cyclodextrins in a distribution can lead to changes in the complexation equilibrium constant $K_{1:1}$ which in turn will affect the required molar ratios of the derivatized cyclodextrin to active agent. The equilibrium constant is also somewhat variable with temperature and allowances in the ratio are required such that the agent remains solubilized during the temperature fluctuations that can occur during manufacture, storage, transport, and use. The equilibrium constant can also vary with pH and allowances in the ratio can be required such that the agent remains solubilized during pH fluctuations that can occur during manufacture, storage, transport, and use. The equilibrium constant can also vary due the presence of other excipients (e.g., buffers, preservatives, antioxidants). Accordingly, the ratio of derivatized cyclodextrin to active agent can be varied from the ratios set forth herein in order to compensate for the above-mentioned variables.

The alkylated cyclodextrins made according to a process of the present invention can be employed in compositions, formulations, methods and systems as such those disclosed in U.S. Pat. Nos. 5,134,127, 5,376,645, 5,914,122, 5,874,418, 6,046,177, 6,133,248, 6,153,746, 6,407,079, 6,869,939, 7,034,013, 7,625,878, 7,629,331, and 7,635,773; U.S. Pub. Nos. 2005/0164986, 2005/0186267, 2005/0250738, 2006/0258537, 2007/0020196, 2007/0020298, 2007/0020299, 2007/0175472, 2007/0202054, 2008/0194519, 2009/0011037, 2009/0012042, 2009/0123540; U.S. application Ser. Nos. 12/404,174, 12/407,734, 61/050,918, 61/177,718, and 61/182,560; and PCT International Application Nos. PCT/US06/62346, PCT/US07/71758, PCT/US07/71748, PCT/US07/72387, PCT/US07/72442, PCT/US07/78465, PCT/US08/61697, PCT/US08/61698, PCT/US08/70969, and PCT/US08/82730, the entire disclosures of which are hereby incorporated by reference. The alkylated cyclodextrins prepared according to the processes herein can also be used as suitable substitutes for other known grades of alkylated cyclodextrins possessing the same functional groups.

In some embodiments, an alkylated cyclodextrin possesses greater water solubility than a corresponding cyclodextrin from which an alkylated cyclodextrin composition of the present invention is prepared. For example, in some embodiments, an underivatized cyclodextrin is utilized as a starting material, e.g., α-, β- or γ-cyclodextrin, commercially available from, e.g., WACKER BIOCHEM CORP. (Adrian, Mich.), and other sources. Underivatized cyclodextrins have limited water solubility compared to the alkylated cyclodextrins compositions of the present invention. For example, underivatized α-CD, β-CD, γ-CD have a solubility in water solubility of about 145 g/L, 18.5 g/L, and 232 g/L, respectively, at saturation.

The water-soluble alkylated cyclodextrin composition is optionally processed to remove a major portion (e.g., >50%) of an underivatized cyclodextrin, or other contaminants.

The terms "alkylene" and "alkyl," as used herein (e.g., in the —O—($C_2$-$C_6$-alkylene)$SO_3^-$ group or in the alkylamine cations), include linear, cyclic, and branched, saturated and unsaturated (i.e., containing one or more double bonds), divalent alkylene groups and monovalent alkyl groups, respectively. For example, SAE or HAE moieties can have the same type or different type of alkylene (alkyl) radical upon each occurrence in an alkylated cyclodextrin composition. In such embodiments, the alkylene radical in the SAE or HAE moiety can be ethyl, propyl, butyl, pentyl or hexyl in each occurrence in an alkylated cyclodextrin composition.

The term "alkanol" in this text likewise includes both linear, cyclic and branched, saturated and unsaturated alkyl components of the alkanol groups, in which the hydroxyl groups can be situated at any position on the alkyl moiety. The term "cycloalkanol" includes unsubstituted or substituted (e.g., by methyl or ethyl)cyclic alcohols.

In some embodiments, the present invention provides an alkyl ether cyclodextrin (AE-CD) composition, comprising an alkyl ether cyclodextrin having an average degree of substitution of 2 to 9, less than 500 ppm of a phosphate, and less than 0.5% (w/w) of a chloride, wherein the AE-CD composition has an absorption of less than 1 A.U., as determined by UV/vis spectrophotometry at a wavelength of 245 nm to 270 nm for an aqueous solution containing 300 mg of the AE-CD composition per mL of solution in a cell having a 1 cm path length. In some embodiments, said absorption of less than 1 A.U. is due to a drug degrading agent. In some embodiments, the alkyl ether cyclodextrin composition is not a sulfobutyl ether cyclodextrin composition. In some embodiments, the alkyl ether cyclodextrin is not a sulfobutyl ether β-cyclodextrin. In some embodiments, the AE-CD composition has an absorption of 0.5 A.U. or less as determined by UV/vis spectrophotometry at a wavelength of 245 nm to 270 nm for an aqueous solution containing 300 mg of the AE-CD composition per mL of solution in a cell having a 1 cm path length. In some embodiments, said absorption of 0.5 A.U. or less is due to a drug degrading agent. In some embodiments, the AE-CD composition has an absorption of 0.2 A.U. or less as determined by UV/vis spectrophotometry at a wavelength of 245 nm to 270 nm for an aqueous solution containing 300 mg of the AE-CD composition per mL of solution in a cell having a 1 cm path length. In some embodiments, said absorption of 0.2 A.U. or less is due to a drug degrading agent. In some embodiments, the absorption of the AE-CD composition is determined by UV/vis spectrophotometry at a wavelength of 245 nm to 270 nm for an aqueous solution containing 500 mg of the AE-CD composition per mL of solution in a cell having a 1 cm path length.

In some embodiments, the present invention provides an alkyl ether cyclodextrin (AE-CD) composition, comprising an alkyl ether cyclodextrin having an average degree of substitution of 2 to 9, less than 500 ppm of a phosphate, and less than 0.5% (w/w) of a chloride, wherein the AE-CD composition has an absorption of less than 1 A.U., as determined by UV/vis spectrophotometry at a wavelength of 320 nm to 350 nm for an aqueous solution containing 300 mg of the AE-CD composition per mL of solution in a cell having a 1 cm path length. In some embodiments, said absorption of less than 1 A.U. is due to a color forming agent. In some embodiments, the alkyl ether cyclodextrin composition is not a sulfobutyl ether cyclodextrin composition. In some embodiments, the alkyl ether cyclodextrin is not a sulfobutyl ether β-cyclodextrin. In some embodiments, the AE-CD composition has an absorption of 0.5 A.U. or less as determined by UV/vis spectrophotometry at a wavelength of 320 nm to 350 nm for an aqueous solution containing 300 mg of the SAE-CD composition per mL of solution in a cell having a 1 cm path length. In some embodiments, said absorption of 0.5 A.U. or less is due to a color forming agent. In some embodiments, the AE-CD composition has an absorption of 0.2 A.U. or less as determined by UV/vis spectrophotometry at a wavelength of 245 nm to 270 nm for an aqueous solution containing 300 mg of the AE-CD composition per mL of solution in a cell having a 1 cm path length. In some embodiments, said absorption of 0.2 A.U. or less is due to a color forming agent. In some embodiments, the absorption of the AE-CD composition is determined by UV/vis spectrophotometry at a wavelength of 320 nm to 350 nm for an aqueous solution containing 500 mg of the SAE-CD composition per mL of solution in a cell having a 1 cm path length.

In some embodiments, the average degree of substitution of the AE-CD is 4.5 to 7.5. In some embodiments, the average degree of substitution of the AE-CD is 6 to 7.5. In some embodiments, the average degree of substitution of the AE-CD is 6.2 to 6.9.

In some embodiments, the present invention provides a composition comprising a AE-CD composition and an active agent.

In some embodiments, the present invention provides a sulfoalkyl ether cyclodextrin (SAE-CD) composition, comprising a sulfoalkyl ether cyclodextrin having an average degree of substitution of 2 to 9, less than 500 ppm of a phosphate, and less than 0.5% (w/w) of a chloride, wherein the SAE-CD composition has an absorption of less than 1 A.U., as determined by UV/vis spectrophotometry at a wavelength of 245 nm to 270 nm for an aqueous solution containing 300 mg of the SAE-CD composition per mL of solution in a cell having a 1 cm path length. In some embodiments, said absorption of less than 1 A.U. is due to a drug degrading agent. In some embodiments, the sulfoalkyl ether cyclodextrin composition is not a sulfobutyl ether cyclodextrin composition. In some embodiments, the sulfoalkyl ether cyclodextrin is not a sulfobutyl ether β-cyclodextrin. In some embodiments, the SAE-CD composition has an absorption of 0.5 A.U. or less as determined by UV/vis spectrophotometry at a wavelength of 245 nm to 270 nm for an aqueous solution containing 300 mg of the SAE-CD composition per mL of solution in a cell having a 1 cm path length. In some embodiments, said absorption of 0.5 A.U. or less is due to a drug degrading agent. In some embodiments, the SAE-CD composition has an absorption of 0.2 A.U. or less as determined by UV/vis spectrophotometry at a wavelength of 245 nm to 270 nm for an aqueous solution containing 300 mg of the SAE-CD composition per mL of solution in a cell having a 1 cm path length. In some embodiments, said absorption of 0.2 A.U. or less is due to a drug degrading agent. In some embodiments, the absorption of the SAE-CD composition is determined by UV/vis spectrophotometry at a wavelength of 245 nm to 270 nm for an aqueous solution containing 500 mg of the SAE-CD composition per mL of solution in a cell having a 1 cm path length.

In some embodiments, the sulfoalkyl ether cyclodextrin is a compound of Formula (II):

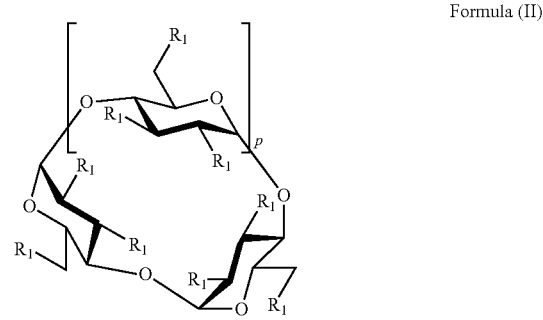

Formula (II)

wherein p is 4, 5, or 6, and $R_1$ is independently selected at each occurrence from —OH or —O—($C_2$-$C_6$ alkylene)-$SO_3^-$-T, wherein T is independently selected at each occurrence from pharmaceutically acceptable cations, provided that at least one $R_1$ is —OH and at least one $R_1$ is O—($C_2$-$C_6$ alkylene)-$SO_3^-$-T. In some embodiments, $R_1$ is independently selected at each occurrence from —OH or —O—($C_4$ alkylene)-$SO_3^-$-T, and -T is $Na^+$ at each occurrence.

In some embodiments, the present invention provides a sulfoalkyl ether cyclodextrin (SAE-CD) composition, comprising a sulfoalkyl ether cyclodextrin having an average degree of substitution of 2 to 9, less than 500 ppm of a phosphate, and less than 0.5% (w/w) of a chloride, wherein the SAE-CD composition has an absorption of 1 A.U. or less, as determined by UV/vis spectrophotometry at a wavelength of 320 nm to 350 nm for an aqueous solution containing 300 mg of the SAE-CD composition per mL of solution in a cell having a 1 cm path length. In some embodiments, said absorption of 1 A.U. or less is due to a color forming agent. In some embodiments, the sulfoalkyl ether cyclodextrin composition is not a sulfobutyl ether cyclodextrin composition. In some embodiments, the sulfoalkyl ether cyclodextrin is not a sulfobutyl ether β-cyclodextrin. In some embodiments, the SAE-CD composition has an absorption of 0.5 A.U. or less as determined by UV/vis spectrophotometry at a wavelength of 320 nm to 350 nm for an aqueous solution containing 300 mg of the SAE-CD composition per mL of solution in a cell having a 1 cm path length. In some embodiments, said absorption of 0.5 A.U. or less is due to a color forming agent. In some embodiments, the SAE-CD composition has an absorption of 0.2 A.U. or less as determined by UV/vis spectrophotometry at a wavelength of 245 nm to 270 nm for an aqueous solution containing 300 mg of the SAE-CD composition per mL of solution in a cell having a 1 cm path length. In some embodiments, said absorption of 0.2 A.U. or less is due to a color forming agent. In some embodiments, the absorption of the SAE-CD composition is determined by UV/vis spectrophotometry at a wavelength of 320 nm to 350 nm for an aqueous solution containing 500 mg of the SAE-CD composition per mL of solution in a cell having a 1 cm path length.

In some embodiments, the average degree of substitution of the SAE-CD is 4.5 to 7.5. In some embodiments, the average degree of substitution of the SAE-CD is 6 to 7.5. In some embodiments, the average degree of substitution of the SAE-CD is 6.2 to 6.9.

In some embodiments, the present invention provides a composition comprising a SAE-CD composition and an active agent.

The present invention is also directed to a method for stabilizing an active agent, the method comprising providing an alkylated cyclodextrin composition comprising an alkylated cyclodextrin, less than 500 ppm of a phosphate, and less than 0.5% of a chloride, wherein the alkylated cyclodextrin composition has an absorption of less than 1 A.U., as determined by UV/vis spectrophotometry at a wavelength of 245 nm to 270 nm for an aqueous solution containing 300 mg of the alkylated cyclodextrin composition per mL of solution in a cell having a 1 cm path length; and combining the alkylated cyclodextrin composition with an active agent. In some embodiments, said absorption of less than 1 A.U. is due to a drug degrading agent.

The present invention is also directed to a method for stabilizing an active agent, the method comprising providing an alkylated cyclodextrin composition comprising an alkylated cyclodextrin, less than 500 ppm of a phosphate, and less than 0.5% of a chloride, wherein the alkylated cyclodextrin composition has an absorption of less than 1 A.U., as determined by UV/vis spectrophotometry at a wavelength of 245 nm to 270 nm for an aqueous solution containing 300 mg of the alkylated cyclodextrin composition per mL of solution in a cell having a 1 cm path length; and combining the alkylated cyclodextrin composition with an active agent. In some embodiments, said absorption of less than 1 A.U. is due to a color forming agent.

The present invention provides a process for preparing an alkylated cyclodextrin composition, the process comprising:

(a) mixing a cyclodextrin with an alkylating agent in the presence of an alkalizing agent to form a reaction milieu comprising an alkylated cyclodextrin, one or more unwanted components, and one or more drug-degrading impurities;

(b) conducting one or more separations to remove the one or more unwanted components from the reaction milieu to form a partially purified solution comprising the alkylated cyclodextrin and the one or more drug-degrading impurities, wherein the one or more separations are ultrafiltration, diafiltration, centrifugation, extraction, solvent precipitation, or dialysis;

(c) treating the partially purified solution with a phosphate-free activated carbon having a conductivity of 10 µS or less and producing the alkylated cyclodextrin.

The term "batch" or "lot" as used herein refers to a discrete manufacturing or processing run from start of the processing run to the finish of the processing run. In some embodiments, the present invention provides a process for preparing more than one lot of an alkylated cyclodextrin composition comprising an alkylated cyclodextrin, the process comprising: (a) mixing a cyclodextrin with an alkylating agent to form a reaction milieu comprising an alkylated cyclodextrin, one or more unwanted components, and one or more drug-degrading impurities; (b) conducting one or more separations to remove the one or more unwanted components from the reaction milieu to form a partially purified solution comprising the alkylated cyclodextrin and the one or more drug-degrading impurities, wherein the one or more separations are ultrafiltration, diafiltration, centrifugation, extraction, solvent precipitation, or dialysis; (c) treating the partially purified solution with a phosphate-free activated carbon having a residual conductivity of 10 µS or less and producing a lot of an alkylated cyclodextrin; and (d) repeating (a)-(c) to obtain another lot of an alkylated cyclodextrin composition.

In some embodiments, the more than one lot of an alkylated cyclodextrin composition is at least 4 lots, at least 5 lots, at least 6 lots, at least 7 lots, at least 8 lots, at least 9 lots, at least 10 lots, at least 11 lots, at least 12 lots, at least 13 lots, at least 14 lots, at least 15 lots, at least 16 lots, at least 17 lots, at least 18 lots, at least 19 lots, at least 20 lots, at least 30 lots, at least 40 lots, at least 50 lots, at least 60 lots, at least 70 lots, at least 80 lots, at least 90 lots, or at least 100 lots. In some embodiments, the more than one lot of an alkylated cyclodextrin composition is 4 to 100 lots, 10 to 100 lots, 20 to 100 lots, 30 to 100 lots, 40 to 100 lots, 50 to 100 lots, 10 to 20 lots, 10 to 30 lots, 10 to 40 lots, or 10 to 50 lots.

In some embodiments, 50% or more of the lots of the alkylated cyclodextrin composition have a chloride level of less than 0.1% (w/w), 65% or more of the lots of the alkylated cyclodextrin composition have a chloride level of less than 0.1% (w/w), 75% or more of the lots of the alkylated cyclodextrin composition have a chloride level of less than 0.1% (w/w), 80% or more of the lots of the alkylated cyclodextrin composition have a chloride level of less than 0.1% (w/w), 85% or more of the lots of the alkylated cyclodextrin composition have a chloride level of less than 0.1% (w/w), 90% or more of lots of the alkylated cyclodextrin composition have a chloride level of less than 0.1% (w/w), 95% or more of the lots of the alkylated cyclodextrin composition have a chloride level of less than 0.1% (w/w), 98% or more of the lots of the alkylated cyclodextrin composition have a chloride level of less than 0.1% (w/w), 50% or more of the lots of the alkylated cyclodextrin composition have a chloride level of less than 0.08% (w/w), 65% or more of the lots of the alkylated cyclodextrin composition have a chloride level of less than 0.08% (w/w), 75% or more of the lots of the alkylated cyclodextrin composition have a chloride level of less than 0.08% (w/w), 80% or more of the lots of the alkylated cyclodextrin composition have a chloride level of less than 0.08% (w/w), 85% or more of the lots of the alkylated cyclodextrin composition have a chloride level of less than 0.08% (w/w), 90% or more of the lots of the alkylated cyclodextrin composition have a chloride level of less than 0.08% (w/w), 95% or more of the lots of the alkylated cyclodextrin composition have a chloride level of less than 0.08% (w/w), 98% or more of the lots of the alkylated cyclodextrin composition have a chloride level of less than 0.08% (w/w), 50% or more of the lots of the alkylated cyclodextrin composition have a chloride level of less than 0.05% (w/w), 65% or more of the lots of the alkylated cyclodextrin composition have a chloride level of less than 0.05% (w/w), 75% or more of the lots of the alkylated cyclodextrin composition have a chloride level of less than 0.05% (w/w), 80% or more of the lots of the alkylated cyclodextrin composition have a chloride level of less than 0.05% (w/w), 85% or more of the lots of the alkylated cyclodextrin composition have a chloride level of less than 0.05% (w/w), 90% or more of the lots of the alkylated cyclodextrin composition have a chloride level of less than 0.05% (w/w), 95% or more of the lots of the alkylated cyclodextrin composition have a chloride level of less than 0.05% (w/w), or 98% or more of the lots of the alkylated cyclodextrin composition have a chloride level of less than 0.05% (w/w).

In some embodiments, the lots of the alkylated cyclodextrin composition are prepared sequentially.

Preparation of Alkylated Cyclodextrin Compositions

The present invention describes several methods for preparing an alkylated cyclodextrin composition. In general, an underivatized cyclodextrin starting material in neutral to alkaline aqueous media is exposed to substituent precursor. The substituent precursor can be added incrementally or as a bolus, and the substituent precursor can be added before, during, or after exposure of the cyclodextrin starting material to the optionally alkaline aqueous media. Additional alkaline material or buffering material can be added as needed to maintain the pH within a desired range. The derivatization reaction can be conducted at ambient to elevated temperatures. Once derivatization has proceeded to the desired extent, the reaction is optionally quenched by addition of an acid. The reaction milieu is further processed (e.g., solvent precipitation, filtration, centrifugation, evaporation, concentration, drying, chromatography, dialysis, and/or ultrafiltration) to remove undesired materials and form the target composition. After final processing, the composition can be in the form of a solid, liquid, semi-solid, gel, syrup, paste, powder, aggregate, granule, pellet, compressed material, reconstitutable solid, suspension, glass, crystalline mass, amorphous mass, particulate, bead, emulsion, or wet mass.

The invention provides a process of making an alkylated cyclodextrin composition comprising an alkylated cyclodextrin, optionally having a pre-determined degree of substitution, the process comprising: combining an unsubstituted cyclodextrin starting material with an alkylating agent in an amount sufficient to effect the pre-determined degree of substitution, in the presence of an alkali metal hydroxide; conducting alkylation of the cyclodextrin within a pH of 9 to 11 until residual unreacted cyclodextrin is less than 0.5% by weight, or less than 0.1%; adding additional hydroxide in an amount sufficient to achieve the degree of substitution and allowing the alkylation to proceed to completion; and adding additional hydroxide to destroy any residual alkylating agent.

Adding an additional hydroxide can be conducted using a quantity of hydroxide, and under conditions (i.e., amount of additional hydroxide added, temperature, length of time during which the alkylating agent hydrolysis is conducted) such that the level of residual alkylating agent in the aqueous crude product is reduced to less than 20 ppm or less than 2 ppm.

It is possible that the reaction milieu or the partially purified aqueous solution will comprise unreacted alkylating agent. The alkylating agent can be degraded in situ by adding additional alkalizing agent or by heating a solution containing the agent. Degrading an excess alkylating agent will be required where unacceptable amounts of alkylating agent are present in the reaction milieu following termination of the mixing. The alkylating agent can be degraded in situ by adding additional alkalizing agent or by heating a solution containing the agent.

Degrading can be conducted by: exposing the reaction milieu to an elevated temperature of at least 60° C., at least 65° C., or 60° C. to 85° C., 60° C. to 80° C., or 60° C. to 95° C. for a period of at least 6 hours, at least 8 hours, 8 hours to 12 hours, 6 hours to 72 hours, or 48 hours to 72 hours, thereby degrading the alkylating agent in situ and reducing the amount of or eliminating the alkylating agent in the aqueous liquid.

After the reaction has been conducted as described herein, the aqueous medium containing the alkylated cyclodextrin can be neutralized to a pH of 7 in order to quench the reaction. The solution can then be diluted with water in order to lower viscosity, particularly if further purification is to be conducted. Further purifications can be employed, including, but not limited to, diafiltration on an ultrafiltration unit to purge the solution of reaction by-products such as salts (e.g., NaCl if sodium hydroxide was employed as the base) and other low molecular weight by-products. The product can further be concentrated by ultrafiltration. The product solution can then be treated with activated carbon in order to improve its color, reduce bioburden, and substantially remove one or more drug degrading impurities. The product can be isolated by a suitable drying technique such as freeze drying, spray drying, or vacuum drum drying.

The reaction can initially be prepared by dissolving an unsubstituted α-, β-, or γ-cyclodextrin starting material in an aqueous solution of base, usually a hydroxide such as lithium, sodium, or potassium hydroxide. The base is present in a catalytic amount (i.e., a molar ratio of less than 1:1 relative to the cyclodextrin), to achieve a pre-determined or desired degree of substitution. That is, the base is present in an amount less than one molar equivalent for each hydroxyl sought to be derivatized in the cyclodextrin molecule. Because cyclodextrins become increasingly soluble in aqueous solution as the temperature is raised, the aqueous reaction mixture containing base and cyclodextrin should be raised to a temperature of 50° C. to ensure complete dissolution. Agitation is generally employed throughout the course of the alkylation reaction.

After dissolution is complete, the alkylating agent is added to start the alkylation reaction. The total amount of alkylating agent added throughout the reaction will generally be in excess of the stoichiometric amount required to complete the reaction relative to the amount of cyclodextrin, since some of the alkylating agent is hydrolyzed and/or otherwise destroyed/degraded during the reaction such that it is not available for use in the alkylation reaction. The exact amount of alkylating agent to use for a desired degree of substitution can be determined through the use of trial runs. The entire amount of alkylating agent needed to complete the reaction can be added prior to initiating the reaction. Because the system is aqueous, the reaction is generally conducted at a temperature 50° C. and 100° C. The reaction can be conducted at a temperature less than 100° C., so that specialized pressure equipment is not required. In general, a temperature of 65° C. to 95° C. is suitable.

During the initial phase of the reaction (herein referred to as the pH-control phase), care should be taken to monitor the pH and maintain it at least basic, or in at a pH of 8 to 11. Monitoring of pH can be effected conventionally as by using a standard pH meter. Adjustment of the pH can be effected by adding an aqueous solution of hydroxide, e.g., a 10-15% solution. During the initial pH-control phase, unreacted cyclodextrin is reacted to the extent that less than 0.5% by weight, or less than 0.1% by weight, of unreacted cyclodextrin remains in solution. Substantially the entire initial charge of cyclodextrin is thus reacted by being partially substituted, but to less than the desired pre-determined degree of substitution. Residual cyclodextrin can be monitored throughout this initial phase, for example by HPLC as described below, until a desired endpoint of less than 0.5%, or less than 0.1%, of residual cyclodextrin starting material, has been achieved. The pH can be maintained and/or raised by adding concentrated hydroxide to the reaction medium continuously or in discrete amounts as small increments. Addition in small increments is particularly suitable.

Once an alkylation procedure has been standardized or optimized so that it is known that particular amounts of reactants can be combined in a procedure which produces the desired degree of substitution in conjunction with low residual cyclodextrin, then the procedure can simply be checked at the end, as opposed to throughout or during the initial pH-control, to ensure that a low level of residual (unreacted) cyclodextrin starting material has been achieved. The following table sets forth a relationship between the amount of butane sultone charged into a reactor and the resulting average degree of substitution of the SAE-CD.

| Butane Sultone Charged (Approximate equivalents of BS per mole of cyclodextrin) | Corresponding Approximate Predetermined ADS for SAE-CD formed |
|---|---|
| 2 | 2 |
| 3 | 3 |
| 4 | 4 |
| 5 | 5 |
| 6 | 5-5.5 |
| 7 | 5.5 to 6.5 |
| 8 | 6.5 to 7 |
| 9 | 7-8 |
| 12 | 8-9 |

It is noted that the initial pH of the reaction medium can be above 11, for example after combining the initial charge of cyclodextrin starting material and base, but prior to addition of alkylating agent. After an alkylating agent has been added and the reaction commences, however, the pH quickly drops, necessitating addition of base to maintain a basic pH of about 8 to about 11.

Once the level of residual unreacted cyclodextrin has reached a desired level, e.g., below 0.5% by weight, during the pH control stage, the pH can be raised to above 11, for example a level above 12, by adding additional base to drive the reaction to completion. The pH can be at least 12 so that the reaction proceeds at a reasonable rate, but not so high that unreacted alkylating agent is hydrolyzed rapidly rather than reacting with cyclodextrin. During this latter phase of the reaction, additional substitution of the cyclodextrin molecule is effected until the pre-determined degree of substitution has been attained. The total amount of hydroxide added throughout the reaction is typically on the order of the amount stoichiometrically required plus a 10-20% molar excess relative to the amount of alkylating agent employed. The addition of more than a 10-20% excess is also feasible. The reaction end point, as noted above, can be detected by HPLC. A suitable temperature is 65° C. to 95° C. The HPLC system typically employs an anion exchange analytical column with pulsed amperometric detection (PAD). Elution can be by gradient using a two-solvent system, e.g., Solvent A being 25 mM (millimolar) aqueous sodium hydroxide, and Solvent B being 1 M sodium nitrate in 250 mM sodium hydroxide.

Once the alkylation reaction is complete and the low residual cyclodextrin end point has been reached, additional hydroxide can be added to destroy and/or degrade any residual alkylating agent. The additional hydroxide is typically added in an amount of 0.5 to 3 molar equivalents relative to cyclodextrin, and the reaction medium is allowed to continue heating at 65° C. to 95° C., typically for 6 hours to 72 hours.

After residual alkylating agent destruction, the resulting crude product can be additionally treated to produce a final product by being diluted, diafiltered to reduce or rid the product of low molecular weight components such as salts, concentrated, carbon treated, and dried.

The pH is initially monitored to ensure that it remains at 8 to 11 as the alkyl derivatization reaction proceeds. In this initial stage, addition of a hydroxide to facilitate the alkylation can be staged or step-wise. Monitoring the pH of the reaction ensures that the reaction can be controlled such that the entire initial stock of cyclodextrin starting material is essentially reacted to the extent of effecting, on average, at least one alkyl substitution per cyclodextrin molecule. The entire cyclodextrin reactant is thus consumed at the beginning of the process, so that the level of residual (unreacted) cyclodextrin in the crude product is low, relative to the crude product produced by a process which features initially combining the entire stoichiometric or excess amount of base with cyclodextrin and alkylating agent and allowing the reaction to proceed uncontrolled. After the entire charge of cyclodextrin starting material has been partially reacted, the remaining hydroxide can be added to drive the reaction to completion by finishing the alkyl substitution to the pre-determined, desired degree. After the initial charge of cyclodextrin has been consumed in the first pH-controlled phase, the rate of hydroxide addition is not critical. Thus, the hydroxide can be added (e.g., as a solution) continuously or in discrete stages. In addition, the pH of the reaction medium should be maintained above about 12 so that the rate of reaction is commercially useful.

Reduction and Removal of Impurities in a Cyclodextrin Composition

Initial pH control provides a means for reducing certain by-products from the reaction mixture. For example, an acid is produced as a result of the alkylation and the pH of the reaction mixture tends to decrease (i.e., become more acidic) as the reaction proceeds. On one hand, the reaction is maintained basic because if the reaction medium becomes acidic, then the reaction will slow considerably or stop. Accordingly, the pH of the reaction medium should be maintained at a level of at least 8 by adding aqueous hydroxide as needed. On the other hand, if the pH is allowed to exceed a certain level, for example, a pH greater than 12, then the reaction can produce a high level of by-products such as 4-hydroxyalkylsulfonate and bis-sulfoalkyl ether, thus consuming the alkylating agent starting material. By monitoring the pH of the reaction solution and maintaining the pH at 8 to 12, or 8 to 11, the reaction proceeds while producing a relatively low-level of by-products, and a relatively clean reaction mixture containing relatively low levels of the aforementioned by-products is provided.

Reference above to a reactant being provided in an amount which is "stoichiometrically sufficient," and the like, is with respect to the amount of reactant needed to fully derivatize the cyclodextrin of interest to a desired degree of substitution. As used herein, an "alkali metal hydroxide" refers to LiOH, NaOH, KOH, and the like. If it is desired to produce a product suitable for parenteral administration, then NaOH can be used.

The degree of substitution can be controlled by using correspondingly lower or higher amounts of alkylating agent, depending upon whether a lower or higher degree of substitution is desired. Generally, the degree of substitution that can be achieved is an average of from 4.5 to 7.5, 5.5 to 7.5, or 6 to 7.1.

The crude product of the process herein, i.e., the product obtained following residual alkylating agent destruction, contains a lower level of residual cyclodextrin than that produced by a process in which the base is initially added in a single charge, and is provided as a further feature of the invention. The crude product produced by the process of this invention typically contains less than 0.5% by weight residual cyclodextrin, or less than 0.1%. As explained below, the crude product is also advantageous in that it contains very low residual alkylating agent levels.

Typically, the crude aqueous cyclodextrin product solution obtained following residual alkylating agent destruction is purified by ultrafiltration, a process in which the crude product is contacted with a semipermeable membrane that passes low molecular weight impurities through the membrane. The molecular weight of the impurities passed through the membrane depends on the molecular weight cut-off for the membrane. For the instant invention, a membrane having a molecular weight cutoff of 1,000 Daltons ("Da") is typically employed. Diafiltrations and/or ultrafiltrations can be conducted with filtration membranes having a molecular weight cut-off of 500 Da to 2,000 Da, 500 Da to 1,500 Da, 750 Da to 1,250 Da, or 900 Da to 1,100 Da, or about 1,000 Da. The desired product which is in the retentate is then further treated with activated carbon to substantially remove drug-degrading impurities. The crude aqueous cyclodextrin product solution (i.e., obtained after residual alkylating agent destruction but before purification) is advantageous in that it contains less than 2 ppm residual alkylating agent based on the weight of the solution, less than 1 ppm, or less than 250 ppb. The crude solution can also contain essentially no residual alkylating agent.

A final, commercial product can be isolated at this point by, e.g., filtration to remove the activated carbon, followed by evaporation of the water (via, e.g., distillation, spray dying, lyophilization, and the like). The final product produced by the instant invention advantageously contains very low residual levels of alkylating agent, e.g., less than 2 ppm based on the weight of the dry (i.e., containing less than 10% by weight water) final product, less than 1 ppm, less than 250 ppb, or essentially no residual alkylating agent. The final product containing less than 250 ppb of alkylating agent is accordingly provided as an additional feature of the invention. The alkylating agent is reduced following completion of the alkylation to the desired degree of substitution by an alkaline hydrolysis treatment as previously described, i.e., by adding extra hydroxide solution in an amount and under conditions sufficient to reduce the amount of unreacted alkylating agent in the dry product to the desired level below 2 ppm, less than 1 ppm, or less than 250 ppb.

Activated carbon suitable for use in the process of the present invention can be phosphate-free, and can be powder or granular, or a suspension or slurry produced therefrom. Generally, phosphate-free activated carbon is a carbon that was not activated using, or otherwise exposed to, phosphoric acid.

A wide variety of activated carbon is available. For example, Norit-Americas commercializes over 150 different grades and varieties of activated carbon under trademarks such as DARCO®, HYDRODARCO®, NORIT®, BENTONORIT®, PETRODARCO®, and SORBONORIT®. The carbons differ in particle size, application, method of activation, and utility. For example, some activated carbons are optimized for color and/or flavor removal. Other activated carbons are optimized for removal of protein, mineral, and/or amino acid moieties, or for clarifying solutions.

Activated carbons suitable for use according to the present invention include, but are not limited to: DARCO® 4×12, 12×20, or 20×40 granular from lignite, steam activated (Norit Americas, Inc., Amersfoort, Nebr.); DARCO® S 51 HF (from lignite, steam activated, powder); and SHIRASAGI® DC-32 powered or granular carbon from wood, zinc chloride activated (Takeda Chemical Industries, Ltd., Osaka, JP).

Carbon that is activated with phosphoric acid, as used in the prior art for purifying alkyl ether cyclodextrins, is generally unsuitable for use with the present invention, and includes: DARCO® KB-G, DARCO® KB-B and DARCO® KB-WJ, as well as NORIT® CASP and NORIT® CN1.

In some embodiments, the phosphate level in the alkylated cyclodextrin composition is less than 200 ppm, less than 150 ppm, less than 125 ppm, less than 100 ppm, less than 95 ppm, less than 90 ppm, less than 85 ppm, less than 80 ppm, less than 75 ppm, less than 70 ppm, less than 65 ppm, less than 60 ppm, less than 55 ppm, less than 50 ppm, less than 45 ppm, less than 40 ppm, less than 35 ppm, less than 30 ppm, less than 25 ppm, less than 20 ppm, less than 15 ppm, less than 10 ppm, or less than 5 ppm. In some embodiments, the phosphate level in the alkylated cyclodextrin composition is 200 ppm to 5 ppm, 150 ppm to 5 ppm, 125 ppm to 5 ppm, 100 ppm to 5 ppm, 75 ppm to 5 ppm, 50 ppm to 5 ppm, 150 ppm to 10 ppm, 125 ppm to 10 ppm, 100 ppm to 10 ppm, or 75 ppm to 10 ppm.

The loading ratio of activated carbon ultimately depends upon the amount or concentration of the alkylated cyclodextrin, color-forming agents, and drug-degrading agents in solution as well as the physical properties of the activated carbon used. In general, the weight ratio of a cyclodextrin to activated carbon is 5:1 to 10:1, 6:1 to 9:1, 7:1 to 9:1, 8:1 to 9:1, 8.3:1 to 8.5:1, 8.4:1 to 8.5:1, or 8.44:1 by weight per treatment cycle.

As used herein, "treatment cycle" refers to a contacting a predetermined amount of a cyclodextrin composition with a predetermined amount of activated carbon. A treatment cycle can be performed as a single treatment or as a multiple (recycling) pass-through treatment.

The Examples provided herein detail procedures used to evaluate and compare the efficiency of different grades, lots, sources, and types of activated carbon in removing the one or more drug-degrading components and one or more color-forming components present in an in-process milieu or solution of SAE-CD. In general, an in-process milieu or solution is treated with activated carbon and agitated for 120 min. If a loose, particulate, or powdered form of activated carbon is used, it can be removed by filtration of a liquid containing the carbon through a filtration medium to provide the clarified solution.

The filtration membrane can include nylon, TEFLON®, PVDF or another compatible material. The pore size of the filtration membrane can be varied as needed according to the particle size or molecular weight of species being separated from the SAE-CD in a solution containing the same.

The Examples provided herein detail procedures for conducting one or more separations and/or purifications on an aqueous reaction milieu of the present invention. A reaction solution is diluted with aqueous solution and subjected to diafiltration during which the volume of the retentate is maintained substantially constant. The diafiltration can be conducted over a 1,000 Da filter such that one or more unwanted components pass through the filter but the majority of the alkyl ether present in the alkylated cyclodextrin composition is retained in the retentate rather than passing through with the filtrate. The ultrafiltration is then conducted by allowing the volume of the retentate to decrease thereby concentrating the retentate. A filter having a molecular weight cut-off of about 1,000 Da can also be used for the ultrafiltration. The retentate comprises the alkylated cyclodextrin, which can then be treated with activated carbon as described herein.

The one or more unwanted components can include, but are not limited to, low molecular weight impurities (i.e., impurities having a molecular weight of about 500 Da or less), water-soluble and/or water-insoluble ions (i.e., salts), hydrolyzed alkylating agent, 5-(hydroxymethyl)-2-furaldehyde, unreacted cyclodextrin starting material, degraded cyclodextrin species (e.g., degraded and/or ring-opened species formed from unreacted cyclodextrin, partially reacted cyclodextrin, and/or SAE-CD), unreacted alkylating agent (e.g., 1,4-butane sultone), and combinations thereof.

In some embodiments, the compositions of the present invention are substantially free of one or more drug degrading agents. The presence of one or more drug degrading agents can be determined, inter alia, by UV/visible ("UV/vis") spectrophotometry. As used herein, a "drug degrading agent" or "drug degrading impurity" refers to a species, moiety, and the like, that degrades certain active components in aqueous solution. It will be understood that a drug degrading agent may not degrade all drugs with which an alkylated cyclodextrin composition may be combined, depending on the chemical structure of the drug and its degradation pathways. In some embodiments, a drug-degrading species has an absorption in the UV/visible region of the spectrum, for example, an absorption maximum at a wavelength of 245 nm to 270 nm.

The presence of drug degrading agents in the alkylated cyclodextrin composition can be measured by UV/vis in absorbance units (A.U.). In some embodiments, the alkylated cyclodextrin composition has an absorption of less than 1 A.U., less than 0.9 A.U., less than 0.8 A.U., less than 0.7 A.U., less than 0.6 A.U., 0.5 A.U., less than 0.4 A.U., less than 0.3 A.U., less than 0.2 A.U., or less than 0.1 A.U.

The absorbance of the solution becomes linear with the concentration according to the formula:

$$A = \epsilon l c$$

wherein
A=absorbance
$\epsilon$=extinction coefficient
l=path length
c=molar concentration.

The presence of a drug-degrading agent in the alkylated cyclodextrin composition can be measured using UV/vis spectrophotometry at a wavelength of 245 to 270 nm using a cell having a path length of 1 cm. In some embodiments, the alkylated cyclodextrin composition has an absorption of less than 1 A.U. at a wavelength of 245 nm to 270 nm for an aqueous solution containing 200 mg of the alkylated cyclodextrin composition per mL of solution, less than 1 A.U. at a wavelength of 245 nm to 270 nm for an aqueous solution containing 300 mg of the alkylated cyclodextrin composition per mL of solution, less than 1 A.U. at a wavelength of 245 nm to 270 nm for an aqueous solution containing 400 mg of the alkylated cyclodextrin composition per mL of solution, less than 1 A.U. at a wavelength of 245 nm to 270 nm for an aqueous solution containing 500 mg of the alkylated cyclodextrin composition per mL of solution, 0.9 A.U. or less at a wavelength of 245 nm to 270 nm for an aqueous solution containing 200 mg of the alkylated cyclodextrin composition per mL of solution, 0.9 A.U. or less at a wavelength of 245 nm to 270 nm for an aqueous solution containing 300 mg of the alkylated cyclodextrin composition per mL of solution, 0.9 A.U. or less at a wavelength of 245 nm to 270 nm for an aqueous solution containing 400 mg of the alkylated cyclodextrin composition per mL of solution, 0.9 A.U. or less at a wavelength of 245 nm to 270 nm for an aqueous solution containing 500 mg of the alkylated cyclodextrin composition per mL of solution, 0.8 A.U. or less at a wavelength of 245 nm to 270 nm for an aqueous solution containing 200 mg of the alkylated cyclodextrin composition per mL of solution, 0.8 A.U. or less at a wavelength of 245 nm to 270 nm for an aqueous solution containing 300 mg of the alkylated cyclodextrin composition per mL of solution, 0.8 A.U. or less at a wavelength of 245 nm to 270 nm for an aqueous solution containing 400 mg of the alkylated cyclodextrin composition per mL of solution, 0.8 A.U. or less at a wavelength of 245 nm to 270 nm for an aqueous solution containing 500 mg of the alkylated cyclodextrin composition per mL of solution, 0.7 A.U. or less at a wavelength of 245 nm to 270 nm for an aqueous solution containing 200 mg of the alkylated cyclodextrin composition per mL of solution, 0.7 A.U. or less at a wavelength of 245 nm to 270 nm for an aqueous solution containing 300 mg of the alkylated cyclodextrin composition per mL of solution, 0.7 A.U. or less at a wavelength of 245 nm to 270 nm for an aqueous solution containing 400 mg of the alkylated cyclodextrin composition per mL of solution, 0.7 A.U. or less at a wavelength of 245 nm to 270 nm for an aqueous solution containing 500 mg of the alkylated cyclodextrin composition per mL of solution, 0.6 A.U. or less at a wavelength of 245 nm to 270 nm for an aqueous solution containing 200 mg of the alkylated cyclodextrin composition per mL of solution, 0.6 A.U. or less at a wavelength of 245 nm to 270 nm for an aqueous solution containing 300 mg of the alkylated cyclodextrin composition per mL of solution, 0.6 A.U. or less at a wavelength of 245 nm to 270 nm for an aqueous solution containing 400 mg of the alkylated cyclodextrin composition per mL of solution, 0.6 A.U. or less at a wavelength of 245 nm to 270 nm for an aqueous solution containing 500 mg of the alkylated cyclodextrin composition per mL of solution, 0.5 A.U. or less at a wavelength of 245 nm to 270 nm for an aqueous solution containing 200 mg of the alkylated cyclodextrin composition per mL of solution, 0.5 A.U. or less at a wavelength of 245 nm to 270 nm for an aqueous solution containing 300 mg of the alkylated cyclodextrin composition per mL of solution, 0.5 A.U. or less at a wavelength of 245 nm to 270 nm for an aqueous solution containing 400 mg of the alkylated cyclodextrin composition per mL of solution, 0.5 A.U. or less at a wavelength of 245 nm to 270 nm for an aqueous solution containing 500 mg of the alkylated cyclodextrin composition per mL of solution, 0.4 A.U. or less at a wavelength of 245 nm to 270 nm for an aqueous solution containing 200 mg of the alkylated cyclodextrin composition per mL of solution, 0.4 A.U. or less at a wavelength of 245 nm to 270 nm for an aqueous solution containing 300 mg of the alkylated cyclodextrin composition per mL of solution, 0.4 A.U. or less at a wavelength of 245 nm to 270 nm for an aqueous solution containing 400 mg of the alkylated cyclodextrin composition per mL of solution, 0.4 or less A.U. at a wavelength of 245 nm to 270 nm for an aqueous solution containing 500 mg of the alkylated cyclodextrin composition per mL of solution, 0.3 A.U. or less at a wavelength of 245 nm to 270 nm for an aqueous solution containing 200 mg of the alkylated cyclodextrin composition, 0.3 A.U. or less at a wavelength of 245 nm to 270 nm for an aqueous solution containing 300 mg of the alkylated cyclodextrin composition per mL of solution, 0.3 A.U. or less at a wavelength of 245 nm to 270 nm for an aqueous solution containing 400 mg of the alkylated cyclodextrin composition per mL of solution, 0.3 A.U. or less at a wavelength of 245 nm to 270 nm for an aqueous solution containing 500 mg of the alkylated cyclodextrin composition per mL of solution, 0.2 A.U. or less at a wavelength of 245 nm to 270 nm for an aqueous solution containing 200 mg of the alkylated cyclodextrin composition per mL of solution, 0.2 A.U. or less at a wavelength of 245 nm to 270 nm for an aqueous solution containing 300 mg of the alkylated cyclodextrin composition per mL of solution, 0.2 A.U. or less at a wavelength of 245 nm to 270 nm for an aqueous solution containing 400 mg of the alkylated cyclodextrin composition per mL of solution, or 0.2 A.U. or less at a wavelength of 245 nm to 270 nm for an aqueous solution containing 500 mg of the alkylated cyclodextrin composition per mL of solution.

The presence of a color-forming agent in the alkylated cyclodextrin composition can be measured using UV/vis spectrophotometry at a wavelength of 320 nm to 350 nm using a cell having a path length of 1 cm. In some embodiments, the alkylated cyclodextrin composition has an absorption of less than 1 A.U. at a wavelength of 320 nm to 350 nm for an aqueous solution containing 200 mg of the alkylated cyclodextrin composition per mL of solution, less than 1 A.U. at a wavelength of 320 nm to 350 nm for an aqueous solution containing 300 mg of the alkylated cyclodextrin composition per mL of solution, less than 1 A.U. at a wavelength of 320 nm to 350 nm for an aqueous solution containing 400 mg of the alkylated cyclodextrin composition per mL of solution, less than 1 A.U. at a wavelength of 320 nm to 350 nm for an aqueous solution containing 500 mg of the alkylated cyclodextrin composition per mL of solution, 0.9 A.U. or less at a wavelength of 320 nm to 350 nm for an aqueous solution containing 200 mg of the alkylated cyclodextrin composition per mL of solution, 0.9 A.U. or less at a wavelength of 320 nm to 350 nm for an aqueous solution containing 300 mg of the alkylated cyclodextrin composition per mL of solution, 0.9 A.U. or less at a wavelength of 320 nm to 350 nm for an aqueous solution containing 400 mg of the alkylated cyclodextrin composition per mL of solution, 0.9 A.U. or less at a wavelength of 320 nm to 350 nm for an aqueous solution containing 500 mg of the alkylated cyclodextrin composition per mL of solution, 0.8 A.U. or less at a wavelength of 320 nm to 350 nm for an aqueous solution containing 200 mg of the alkylated cyclodextrin composition per mL of solution, 0.8 A.U. or less at a wavelength of 320 nm to 350 nm for an aqueous solution containing 300 mg of the alkylated cyclodextrin composition per mL of solution, 0.8 A.U. or less at a wavelength of 320 nm to 350 nm for an aqueous solution containing 400 mg of the alkylated cyclodextrin composition per mL of solution, 0.8 A.U. or less at a wavelength of 320 nm to 350 nm for an aqueous solution containing 500 mg of the alkylated cyclodextrin composition per mL of solution, 0.7 A.U. or less at a wavelength of 320 nm to 350 nm for an aqueous solution containing 200 mg of the alkylated cyclodextrin composition per mL of solution, 0.7 A.U. or less at a wavelength of 320 nm to 350 nm for an aqueous solution containing 300 mg of the alkylated cyclodextrin composition per mL of solution, 0.7 A.U. or less at a wavelength of 320 nm to 350 nm for an aqueous solution containing 400 mg of the alkylated cyclodextrin composition per mL of solution, 0.7 A.U. or less at a wavelength of 320 nm to 350 nm for an aqueous solution containing 500 mg of the alkylated cyclodextrin composition per mL of solution, 0.6 A.U. or less at a wavelength of 320 nm to 350 nm for an aqueous solution containing 200 mg of the alkylated cyclodextrin composition per mL of solution, 0.6 A.U. or less at a wavelength of 320 nm to 350 nm for an aqueous solution containing 300 mg of the alkylated cyclodextrin composition per mL of solution, 0.6 A.U. or less at a wavelength of 320 nm to 350 nm for an aqueous solution containing 400 mg of the alkylated cyclodextrin composition per mL of solution, 0.6 A.U. or less at a wavelength of 320 nm to 350 nm for an aqueous solution containing 500 mg of the alkylated cyclodextrin composition per mL of solution, 0.5 A.U. or less at a wavelength of 320 nm to 350 nm for an aqueous solution containing 200 mg of the alkylated cyclodextrin composition per mL of solution, 0.5 A.U. or less at a wavelength of 320 nm to 350 nm for an aqueous solution containing 300 mg of the alkylated cyclodextrin composition per mL of solution, 0.5 A.U. or less at a wavelength of 320 nm to 350 nm for an aqueous solution containing 400 mg of the alkylated cyclodextrin composition per mL of solution, 0.5 A.U. or less at a wavelength of 320 nm to 350 nm for an aqueous solution containing 500 mg of the alkylated cyclodextrin composition per mL of solution, 0.4 A.U. or less at a wavelength of 320 nm to 350 nm for an aqueous solution containing 200 mg of the alkylated cyclodextrin composition per mL of solution, 0.4 A.U. or less at a wavelength of 320 nm to 350 nm for an aqueous solution containing 300 mg of the alkylated cyclodextrin composition per mL of solution, 0.4 A.U. or less at a wavelength of 320 nm to 350 nm for an aqueous solution containing 400 mg of the alkylated cyclodextrin composition per mL of solution, 0.4 A.U. or less at a wavelength of 320 nm to 350 nm for an aqueous solution containing 500 mg of the alkylated cyclodextrin composition per mL of solution, 0.3 A.U. or less at a wavelength of 320 nm to 350 nm for an aqueous solution containing 200 mg of the alkylated cyclodextrin composition, 0.3 A.U. or less at a wavelength of 320 nm to 350 nm for an aqueous solution containing 300 mg of the alkylated cyclodextrin composition per mL of solution, 0.3 A.U. or less at a wavelength of 320 nm to 350 nm for an aqueous solution containing 400 mg of the alkylated cyclodextrin composition per mL of solution, 0.3 A.U. or less at a wavelength of 320 nm to 350 nm for an aqueous solution containing 500 mg of the alkylated cyclodextrin composition per mL of solution, 0.2 A.U. or less at a wavelength of 320 nm to 350 nm for an aqueous solution containing 200 mg of the alkylated cyclodextrin composition per mL of solution, 0.2 A.U. or less at a wavelength of 320 nm to 350 nm for an aqueous solution containing 300 mg of the alkylated cyclodextrin composition per mL of solution, 0.2 A.U. or less at a wavelength of 320 nm to 350 nm for an aqueous solution containing 400 mg of the alkylated cyclodextrin composition per mL of solution, or 0.2 A.U. or less at a wavelength of 320 nm to 350 nm for an aqueous solution containing 500 mg of the alkylated cyclodextrin composition per mL of solution.

Not being bound by any particular theory, a drug-degrading agent, species, or moiety can include one or more low-molecular weight species (e.g., a species having a molecular weight less than 1,000 Da), such as, but not limited to a species generated as a side-product and/or decomposition product in the reaction mixture. As such, drug-degrading species include, but are not limited to, a glycosidic moiety, a ring-opened cyclodextrin species, a reducing sugar, a glucose degradation product (e.g., 3,4- dideoxyglucosone-3-ene, carbonyl-containing degradants such as 2-furaldehyde, 5-hydroxymethyl-2-furaldehyde and the like), and combinations thereof.

In some embodiments, the alkylated cyclodextrin composition comprises less than 1% wt., less than 0.5% wt., less than 0.2% wt., less than 0.1% wt., less than 0.08% wt., or less than 0.05% wt. of an alkali metal halide salt.

In some embodiments, the alkylated cyclodextrin composition comprises less than 1% wt., less than 0.5% wt., less than 0.25% wt., less than 0.1% wt., less than 0.08% wt., or less than 0.05% wt. of a hydrolyzed alkylating agent.

In some embodiments, the alkylated cyclodextrin composition comprises less than 500 ppm, less than 100 ppm, less than 50 ppm, less than 20 ppm, less than 10 ppm, less than 5 ppm, less than 2 ppm, less than 1 ppm, less than 500 ppb, or less than 250 ppb of an alkylating agent.

In some embodiments, the alkylated cyclodextrin composition comprises less than 0.5% wt., less than 0.2% wt., less than 0.1% wt., or less than 0.08% wt. of underivatized cyclodextrin.

By "complexed" is meant "being part of a clathrate or inclusion complex with," i.e., a "complexed" therapeutic agent is part of a clathrate or inclusion complex with an alkylated cyclodextrin. The term "major portion" refers to 50% or greater, by weight, or on a molar basis. Thus, a formulation according to the present invention can contain an active agent of which more than about 50% by weight is complexed with an alkylated cyclodextrin. The actual percentage of active agent that is complexed will vary according to the complexation equilibrium binding constant characterizing the complexation of a specific cyclodextrin with a specific active agent. The invention also includes embodiments wherein the active agent is not complexed with the cyclodextrin or in which only a minor portion of the active agent is complexed with the alkylated cyclodextrin. It should be noted that an alkylated cyclodextrin, can form one or more ionic bonds with a positively charged compound. This ionic association can occur regardless of whether the positively charged compound is complexed with the cyclodextrin by inclusion complexation.

Figure 6:
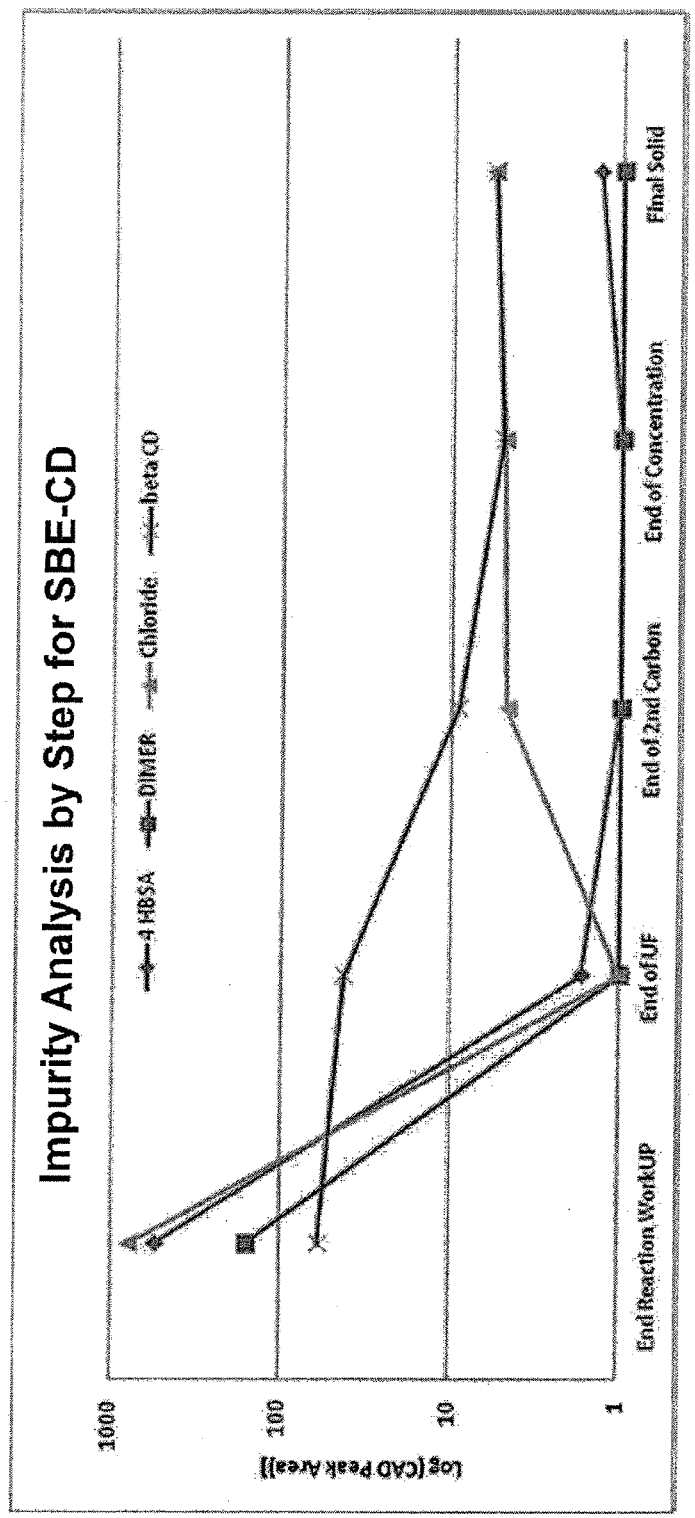
FIG. 6 provides a graphic representation of the impurity levels by a process for preparing $SBE_{6.6}$-β-CD wherein the impurities are measured using a charged aerosol detector.

As shown in FIG. 6, after ultrafiltration of the crude SBE-CD product, impurities such as β-cyclodextrin and 4-hydroxybutane-1-sulfonic acid (4-HBSA) are present. After a second column with activated carbon, the amount of β-cyclodextrin and 4-hydroxybutane-1-sulfonic acid impurities have been reduced. However, as shown in FIG. 6, there are high amounts of chloride present in the product after the two columns.

In the purification process using the activated carbon, although drug-degrading agents have been reduced, high amounts of chloride are present in the alkylated cyclodextrin product. This high amount of chloride in the alkylated cyclodextrin product may react with an active agent and cause degradation of the active agent. Therefore, it is necessary to reduce the chloride levels in the alkylated cyclodextrin product, in particular when the active agent is sensitive to chloride.

Determining whether an active agent is sensitive to chloride can be determined by one of ordinary skill in the art using known techniques.

Figure 7:
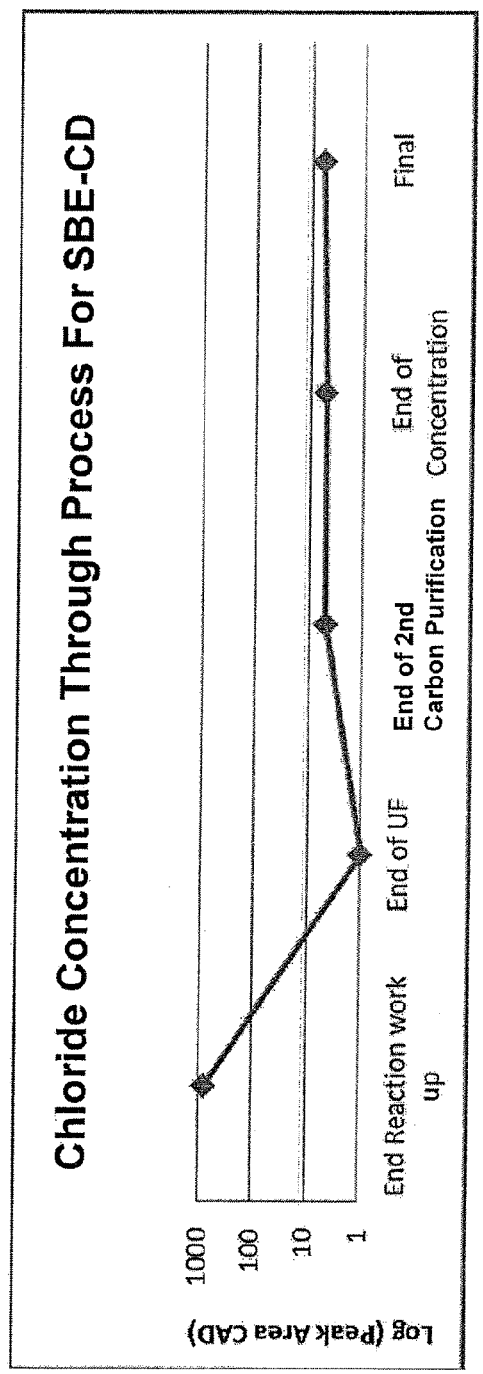
FIG. 7 provides a graphic representation of chloride concentration levels by a process of preparing $SBE_{6.6}$-β-CD wherein the chloride concentration is measured using a charged aerosol detector.

As shown in FIG. 7, after the ultrafiltration, the residual level of chloride drops to approximately zero. After further purification using two columns of activated carbon, chloride is added back into the SBE-CD solution.

During the purification of activated carbon, water is run through the activated carbon column until the conductivity is at a constant level before adding the SBE-CD solution.

The following Table provides details of the amount of water and the resulting conductivity levels measured for columns of activated carbon. As seen in the Table, even in batches where 70,000 liters of water have been used to wash the activated carbon before addition of the SBE-CD solution, a chloride impurity was found in the final SBE-CD solution.

| Batch No. | Water (L) | Column 1 Conductivity (μS) | Column 2 Conductivity (μS) |
|---|---|---|---|
| 17CX01F.HQ00075 | 35,000 | 17.97 | 17.7 |
| discarded | 70,000 | 16.01 | 17.84 |
| 17CX01F.HQ00076 | 36,800 | 18.5 | 36.3 |
| 17CX01F.HQ00077 | 5,420 | 52.0 | 34.7 |
| 17CX01F.HQ00067 | 7,850 | 12.74 | 12.43 |
| 17CX01F.HQ00068 | 7,256 | 9.72 | 9.3 |
| 17CX01F.HQ00069 | 12,131 | 8.86 | 5.58 |
| 17CX01F.HQ00070 | 4,670 | 6.44 | 8.05 |
| 17CX01F.HQ00071 | 6,442 | 6.4 | 6.37 |
| 17CX01F.HQ00072 | 7,500 | 10.98 | 4.74 |
| 17CX01F.HQ00073 | 7,800 | 13.03 | 12.45 |
| 17CX01F.HQ00074 | 2,000 | 4.57 | 8.35 |
| 17CX01F.HQ00078 | 20,630 | 9.68 | 13.14 |

Figure 8:
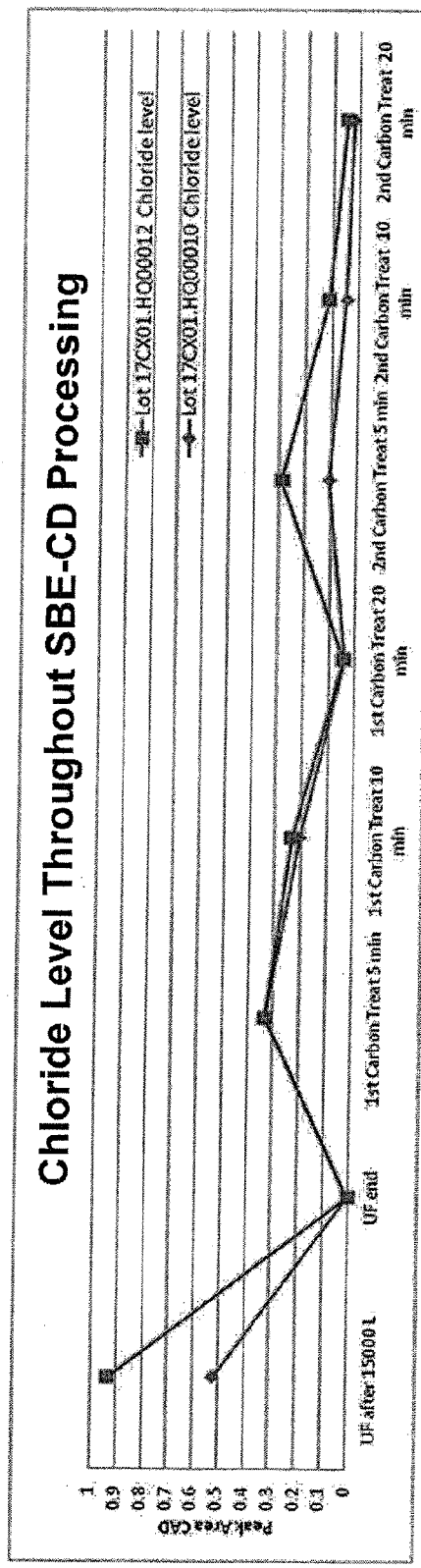
FIG. 8 provides a graphic representation of chloride concentration levels for two batches of $SBE_{6.6}$-β-CD during ultrafiltration, at the end of ultrafiltration processing, 5, 10, and 20 minutes after addition to the first activated carbon column, and 5, 10, and 20 minutes after addition to the second activated carbon column as measured using a charged aerosol detector.

A more extensive examination of the processing before and during circulation with the activated carbon shows that the greatest addition of chloride occurs in the first few minutes of circulation of the SBE-CD solution through the activated carbon bed. As shown in FIG. 8, the chloride impurity level for two SBE-CD commercial batches is approximately zero after the ultrafiltration and increases substantially after treatment with activated carbon during the first 5 minutes, with the level dropping after 10 and 20 minutes.

Figure 9:
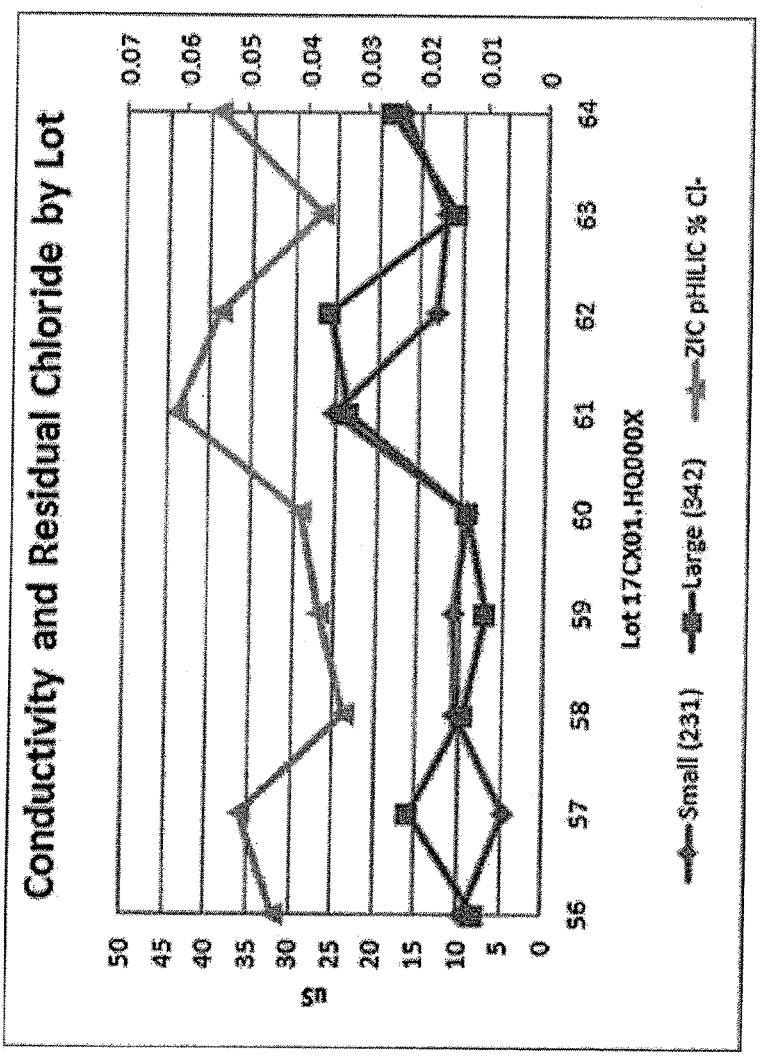
FIG. 9 provides a graphic representation of the level of residual chloride after (a) the first activated carbon column (labeled small) and after (b) the second activated carbon column (labeled large) measured using ion chromatography versus the residual conductivity level (labeled ZIC pHILIC % CO of the final $SBE_{6.6}$-β-CD product measured using a ZIC pHILIC column utilizing a charged aerosol detector (Batch Nos. 17CX01.HQ00056-17CX01.HQ00064).

As shown in FIG. 9, there is a direct correlation between the level of chloride transferred to the SBE-CD solution and the conductivity level at the end of the water wash. In FIG. 9, the conductivity level in a first activated carbon column and a second activated carbon column were measured. The conductivity levels were found to be correlated with the level of residual chloride in the final SBE-CD solid as measured by the ZIC pHILIC method for residual chloride content. Therefore, the conductivity measurement obtained at the end of the wash process correlates with the level of residual chloride in the final SBE-CD product.

The chloride level of the alkylated cyclodextrin composition can be determined using any method commonly used by one of skill in the art. In some embodiments, the chloride level is measured using charged aerosol detection (CAD).

In some embodiments, the chloride level as measured by weight ratio (w/w) in the alkylated cyclodextrin composition is 1% or less, 0.9% or less, 0.8% or less, 0.7% or less, 0.6% or less, 0.5% or less, 0.4% or less, 0.3% or less, 0.2% or less, 0.1% or less, 0.09% or less, 0.08% or less, 0.07% or less, 0.06% or less, 0.05% or less, 0.04% or less, 0.03% or less, 0.02% or less, or 0.01% or less. In some embodiments, the chloride level in the alkylated cyclodextrin composition is 1% to 0.01%, 0.9% to 0.01%, 0.8% to 0.01%, 0.7% to 0.01%, 0.6% to 0.01%, 0.5% to 0.01%, 0.4% to 0.01%, 0.3% to 0.01%, 0.2% to 0.01%, 0.1% to 0.01%, 0.09% to 0.01%, 0.08% to 0.01%, 0.07% to 0.01%, 0.06% to 0.01%, 0.05% to 0.01%, 0.04% to 0.01%, or 0.03% to 0.01%.

The conductivity of the activated carbon's water wash eluent can be determined using any method commonly used by one of skill in the art. In some embodiments, the conductivity is measured using a conductivity meter. In some embodiments, the conductivity is measured using ion chromatography.

In some embodiments, the conductivity of the phosphate-free activated carbon's water wash eluent is measured before addition of the partially purified alkylated cyclodextrin solution. In some embodiments, the conductivity of the activated carbon's water wash eluent prior to addition of the partially purified alkylated cyclodextrin solution is less than 35 µS, less than 34 µS, less than 33 µS, less than 32 µS, less than 31 µS, less than 30 µS, less than 29 µS, less than 28 µS, less than 27 µS, less than 26 µS, less than 25 µS, less than 24 µS, less than 23 µS, less than 22 µS, less than 21 µS, less than 20 µS, less than 19 µS, less than 18 µS, less than 17 µS, less than 16 µS, less than 15 µS, less than 14 µS, less than 13 µS, less than 12 µS, less than 11 µS, less than 10 µS, less than 9 µS, less than 8 µS, less than 7 µS, less than 6 µS, less than 5 µS, less than 4 µS, less than 3 µS, less than 2 µS, or less than 1 µS. In some embodiments, the conductivity of the activated carbon's water wash eluent prior to addition of the partially purified alkylated cyclodextrin solution is 10 µS to 15 µS, 5 µS to 15 µS, 5 µS to 10 µS, 4 µS to 10 µS, 3 µS to 10 µS, or 4 µS to 8 µS.

In some embodiments, the activated carbon is washed 1, 2, 3, 4, 5, 6, 7, 8, 9, 10, 11, 12, 13, 14, or 15 times before addition of the partially purified alkylated cyclodextrin solution. In some embodiments, the activated carbon is washed 1 or more, 2 or more, 3 or more, 4 or more, 5 or more, 6 or more, 7 or more, 8 or more, 9 or more, or 10 or more times before addition of the partially purified alkylated cyclodextrin solution.

Even when the activated carbon in the column is washed with water there may be an inadequate wetting of the activated carbon. In the wash procedure there is no way to control for channeling through the carbon bed. It is believed that by more thoroughly washing the carbon before circulating the alkylated cyclodextrin solution it will reduce or remove all further addition of residual chloride from the alkylated cyclodextrin composition product.

In some embodiments, the activated carbon is added to a dedicated tank system with an agitator and screen system. The activated carbon is charged followed by washing with several portions of water at a determined agitation rate for a determined time period. Following the water wash, the water layer is removed from the dedicated tank and additional water washes occur. After additional water washes the conductivity of the activated carbon is determined and when the conductivity is below a predetermined level the carbon is suspended in water and pumped into carbon housings. The activated carbon would then be ready for addition of the alkylated cyclodextrin solution. The predetermined level of conductivity can be, for example, less than 35 µS, less than 34 µS, less than 33 µS, less than 32 µS, less than 31 µS, less than 30 µS, less than 29 µS, less than 28 µS, less than 27 µS, less than 26 µS, less than 25 µS, less than 24 µS, less than 23 µS, less than 22 µS, less than 21 µS, less than 20 µS, less than 19 µS, less than 18 µS, less than 17 µS, less than 16 µS, less than 15 µS, less than 14 µS, less than 13 µS, less than 12 µS, less than 11 µS, less than 10 µS, less than 9 µS, less than 8 µS, less than 7 µS, less than 6 µS, less than 5 µS, less than 4 µS, less than 3 µS, less than 2 µS, or less than 1 µS.

The agitation can be measured in revolutions per minute (rpm). In some embodiments, the agitation rate can range, for example, from 5 rpm to 300 rpm. For example, the agitation rate can be 5 rpm, 10 rpm, 20 rpm, 30 rpm, 40 rpm, 50 rpm, 60 rpm, 70 rpm, 80 rpm, 90 rpm, or 100 rpm. The agitation time can range from 1 minute to 5 days. The agitation time can be, for example, 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 11 hours, 12 hours, 24 hours, 2 days, 3 days, or 4 days. In some embodiments, the agitation time is 5 minutes to 1 hour, 5 minutes to 2 hours, 5 minutes to 3 hours, 5 minutes to 4 hours, 5 minutes to 5 hours, 10 minutes to 1 hour, 10 minutes to 2 hours, 10 minutes to 3 hours, 10 minutes to 4 hours, 20 minutes to 1 hour, 20 minutes to 2 hours, 20 minutes to 3 hours, 20 minutes to 4 hours, 30 minutes to 1 hour, 30 minutes to 2 hours, 30 minutes to 3 hours, or 30 minutes to 4 hours.

In some embodiments, the tank system is maintained at room temperature (25° C.) during the water washing process. In some embodiments, the tank system can be heated during the water washing process. In some embodiments, the temperature can range, for example, from 30° C. to 100° C. For example, the cooling temperature can be 30° C., 40° C., 50° C., 60° C., 70° C., 80° C., 90° C., or 100° C. The heating time can range from 1 minute to 5 days. The heating time can be, for example, 5 minutes to 4 days, 5 minutes to 60 minutes, 10 minutes to 50 minutes, 20 minutes to 40 minutes, 30 minutes to 60 minutes, 2 hours to 24 hours, 3 hours to 12 hours, 4 hours to 10 hours, 5 hours to 9 hours, 6 hours to 8 hours, 2 days to 4 days, or 3 days to 4 days. In some embodiments, the heating time is 5 minutes to 1 hour, 5 minutes to 2 hours, 5 minutes to 3 hours, 5 minutes to 4 hours, 5 minutes to 5 hours, 10 minutes to 1 hour, 10 minutes to 2 hours, 10 minutes to 3 hours, 10 minutes to 4 hours, 20 minutes to 1 hour, 20 minutes to 2 hours, 20 minutes to 3 hours, 20 minutes to 4 hours, 30 minutes to 1 hour, 30 minutes to 2 hours, 30 minutes to 3 hours, or 30 minutes to 4 hours.

In some embodiments, the activated carbon is washed in the carbon housing until a determined conductivity level has been reached. The activated carbon would then be ready for addition of the alkylated cyclodextrin solution.

In some embodiments, the activated carbon is washed to a constant conductivity level followed by addition of a known amount of alkylated cyclodextrin solution through the activated carbon which is discarded prior to addition of additional alkylated cyclodextrin solution.

The final yield of the alkylated cyclodextrin (in isolated and/or purified or partially purified form) obtained at completion of the process will vary. The final yield of alkylated cyclodextrin based on the cyclodextrin starting material can range from 10% to 95%, 15% to 90%, 20% to 85%, 30% to 85%, 35% to 85%, 40% to 85%, 45% to 80%, 50% to 80%, 55% to 80%, 60% to 80%, 50% to 90%, 55% to 90%, 60% to 90%, 70% to 90%, 80% to 90%, 60% to 98%, 70% to 98%, 80% to 98%, or 90% to 98%. In some embodiments, the final yield of alkylated cyclodextrin based on the cyclodextrin starting material is 80% or greater, 85% or greater, 90% or greater, or 95% or greater.

Uses of Alkylated Cyclodextrin Compositions

Among other uses, an alkylated cyclodextrin composition of the present invention can be used to solubilize and/or stabilize a variety of different materials and to prepare formulations for particular applications. The present alkylated cyclodextrin composition can provide enhanced solubility and/or enhanced chemical, thermochemical, hydrolytic and/or photochemical stability of other ingredients in a composition. For example, an alkylated cyclodextrin composition can be used to stabilize an active agent in an aqueous medium. An alkylated cyclodextrin composition can also be used to increase the solubility of an active agent in an aqueous medium.

The alkylated cyclodextrin composition of the present invention includes one or more active agents. The one or more active agents included in the composition of the present invention can possess a wide range of water solubility, bioavailability and hydrophilicity. Active agents to which the present invention is particularly suitable include water insoluble, poorly water-soluble, slightly water-soluble, moderately water-soluble, water-soluble, very water-soluble, hydrophobic, and/or hydrophilic therapeutic agents. It will be understood by a person of ordinary skill in the art one or more active agents present in a composition of the present invention is independently selected at each occurrence from any known active agent and from those disclosed herein. It is not necessary that the one or more active agents form a complex with the alkylated cyclodextrin, or form an ionic association with the alkylated cyclodextrin.

Active agents generally include physiologically or pharmacologically active substances that produce a systemic or localized effect or effects on animals and human beings. Active agents also include pesticides, herbicides, insecticides, antioxidants, plant growth instigators, sterilization agents, catalysts, chemical reagents, food products, nutrients, cosmetics, vitamins, sterility inhibitors, fertility instigators, microorganisms, flavoring agents, sweeteners, cleansing agents, pharmaceutically effective active agents, and other such compounds for pharmaceutical, veterinary, horticultural, household, food, culinary, agricultural, cosmetic, industrial, cleaning, confectionery and flavoring applications. The active agent can be present in its neutral, ionic, salt, basic, acidic, natural, synthetic, diastereomeric, isomeric, enantiomerically pure, racemic, hydrate, chelate, derivative, analog, or other common form.

Representative pharmaceutically effective active agents include nutrients and nutritional agents, hematological agents, endocrine and metabolic agents, cardiovascular agents, renal and genitourinary agents, respiratory agents, central nervous system agents, gastrointestinal agents, antifungal agents, anti-infective agents, biologic and immunological agents, dermatological agents, ophthalmic agents, antineoplastic agents, and diagnostic agents. Exemplary nutrients and nutritional agents include as minerals, trace elements, amino acids, lipotropic agents, enzymes and chelating agents. Exemplary hematological agents include hematopoietic agents, antiplatelet agents, anticoagulants, coumarin and indandione derivatives, coagulants, thrombolytic agents, antisickling agents, hemorrheologic agents, antihemophilic agents, hemostatics, plasma expanders and hemin. Exemplary endocrine and metabolic agents include sex hormones, uterine-active agents, bisphosphonates, antidiabetic agents, glucose elevating agents, corticosteroids, adrenocortical steroids, parathyroid hormone, thyroid drugs, growth hormones, posterior pituitary hormones, octreotide acetate, imiglucerase, calcitonin-salmon, sodium phenylbutyrate, betaine anhydrous, cysteamine bitartrate, sodium benzoate and sodium phenylacetate, bromocriptine mesylate, cabergoline, agents for gout, and antidotes. Antifungal agents suitable for use with the alkylated cyclodextrin composition of the present invention include, but are not limited to, posaconazole, voriconazole, clotrimazole, ketoconazole, oxiconazole, sertaconazole, tetconazole, fluconazole, itraconazole and miconazole. Antipsychotic agents suitable for use with the alkylated cyclodextrin composition of the present invention include, but are not limited to, clozapine, prochlorperazine, haloperidol, thioridazine, thiothixene, risperidone, trifluoperazine hydrochloride, chlorpromazine, aripiprazole, loxapine, loxitane, olanzapine, quetiapine fumarate, risperidone and ziprasidone.

Exemplary cardiovascular agents include nootropic agents, antiarrhythmic agents, calcium channel blocking agents, vasodilators, antiadrenergics/sympatholytics, renin angiotensin system antagonists, antihypertensive agent combinations, agents for pheochromocytoma, agents for hypertensive emergencies, antihyperlipidemic agents, antihyperlipidemic combination products, vasopressors used in shock, potassium removing resins, edetate disodium, cardioplegic solutions, agents for patent ductus arteriosus, and sclerosing agents. Exemplary renal and genitourinary agents include interstitial cystitis agents, cellulose sodium phosphate, anti-impotence agents, acetohydroxamic acid (aha), genitourinary irrigants, cystine-depleting agents, urinary alkalinizers, urinary acidifiers, anticholinergics, urinary cholinergics, polymeric phosphate binders, vaginal preparations, and diuretics. Exemplary respiratory agents include bronchodilators, leukotriene receptor antagonists, leukotriene formation inhibitors, respiratory inhalant products, nasal decongestants, respiratory enzymes, lung surfactants, antihistamines, normarcotic antitussives, and expectorants. Exemplary central nervous system agents include CNS stimulants, narcotic agonist analgesics, narcotic agonist-antagonist analgesics, central analgesics, acetaminophen, salicylates, normarcotic analgesics, nonsteroidal anti-inflammatory agents, agents for migraine, antiemetic/antivertigo agents, antianxiety agents, antidepressants, antipsychotic agents, cholinesterase inhibitors, nonbarbiturate sedatives and hypnotics, nonprescription sleep aids, barbiturate sedatives and hypnotics, general anesthetics, injectable local anesthetics, anticonvulsants, muscle relaxants, antiparkinson agents, adenosine phosphate, cholinergic muscle stimulants, disulfuram, smoking deterrents, riluzole, hyaluronic acid derivatives, and botulinum toxins. Exemplary gastrointestinal agents including *H pylori* agents, histamine H2 antagonists, proton pump inhibitors, sucralfate, prostaglandins, antacids, gastrointestinal anticholinergics/antispasmodics, mesalamine, olsalazine sodium, balsalazide disodium, sulfasalazine, celecoxib, infliximab, tegaserod maleate, laxatives, antidiarrheals, antiflatulents, lipase inhibitors, GI stimulants, digestive enzymes, gastric acidifiers, hydrocholeretics, gallstone solubilizing agents, mouth and throat products, systemic deodorizers, and anorectal preparations. Exemplary anti-infective agents including penicillins, cephalosporins and related antibiotics, carbapenem, monobactams, chloramphenicol, quinolones, fluoroquinolones, tetracyclines, macrolides, spectinomycin, streptogramins, vancomycin, oxalodinones, lincosamides, oral and parenteral aminoglycosides, colistimethate sodium, polymyxin b sulfate, bacitracin, metronidazole, sulfonamides, nitrofurans, methenamines, folate antagonists, antifungal agents, antimalarial preparations, antituberculosis agents, amebicides, antiviral agents, antiretroviral agents, leprostatics, antiprotozoals, anthelmintics, and cdc anti-infective agents. Exemplary biologic and immunological agents including immune globulins, monoclonal antibody agents, antivenins, agents for active immunization, allergenic extracts, immunologic agents, and antirheumatic agents. Exemplary dermatological agents include topical antihistamine preparations, topical anti-infectives, anti-inflammatory agents, anti-psoriatic agents, antiseborrheic products, arnica, astringents, cleansers, capsaicin, destructive agents, drying agents, enzyme preparations, topical immunomodulators, keratolytic agents, liver derivative complex, topical local anesthetics, minoxidil, eflornithine hydrochloride, photochemotherapy agents, pigment agents, topical poison ivy products, topical pyrimidine antagonist, pyrithione zinc, retinoids, rexinoids, scabicides/pediculicides, wound healing agents, emollients, protectants, sunscreens, ointment and lotion bases, rubs and liniments, dressings and granules, and physiological irrigating solutions. Exemplary ophthalmic agents include agents for glaucoma, mast cell stabilizers, ophthalmic antiseptics, ophthalmic phototherapy agents, ocular lubricants, artificial tears, ophthalmic hyperosmolar preparations, and contact lens products. Exemplary antineoplastic agents include alkylating agents, antimetabolites, antimitotic agents, epipodophyllotoxins, antibiotics, hormones, enzymes, radiopharmaceuticals, platinum coordination complex, anthracenedione, substituted ureas, methylhydrazine derivatives, imidazotetrazine derivatives, cytoprotective agents, DNA topoisomerase inhibitors, biological response modifiers, retinoids, rexinoids, monoclonal antibodies, protein-tyrosine kinase inhibitors, porfimer sodium, mitotane (o, p'-ddd), and arsenic trioxide. Exemplary diagnostic agents include in vivo diagnostic aids, in vivo diagnostic biologicals, and radiopaque agents.

Exemplary active agents also include compounds that are sensitive to chloride levels. Exemplary chloride sensitive active agents include proteasome inhibitors such as bortezomib, disulfuram, epigallocatchin-3-gallate, salinosporamide A, and carfilzomib.

The above-listed active agents should not be considered exhaustive and is merely exemplary of the many embodiments considered within the scope of the invention. Many other active agents can be administered with the formulation of the present invention.

A formulation of the invention can be used to deliver two or more different active agents. Particular combinations of active agents can be provided in a formulation of the invention. Some combinations of active agents include: 1) a first drug from a first therapeutic class and a different second drug from the same therapeutic class; 2) a first drug from a first therapeutic class and a different second drug from a different therapeutic class; 3) a first drug having a first type of biological activity and a different second drug having about the same biological activity; and 4) a first drug having a first type of biological activity and a different second drug having a different second type of biological activity. Exemplary combinations of active agents are described herein.

An active agent contained within a formulation of the invention can be present as its pharmaceutically acceptable salt. As used herein, "pharmaceutically acceptable salt" refers to derivatives of the disclosed compounds wherein the active agent is modified by reacting it with an acid and/or base as needed to form an ionically bound pair. Examples of pharmaceutically acceptable salts include conventional non-toxic salts or the quaternary ammonium salts of a compound formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. Pharmaceutically acceptable salts suitable for use with the present invention can be prepared using an active agent that includes a basic or acidic group by conventional chemical methods. Suitable addition salts are found in *Remington's Pharmaceutical Sciences* (17th ed., Mack Publishing Co., Easton, Pa., 1985), the relevant disclosure of which is hereby incorporated by reference in its entirety.

The present invention is also directed to a method for stabilizing an active agent, the method comprising providing an alkylated cyclodextrin composition comprising an alkylated cyclodextrin, less than 500 ppm of a phosphate, and less than 0.5% of a chloride, wherein the alkylated cyclodextrin composition has an absorption of less than 1 A.U., as determined by UV/vis spectrophotometry at a wavelength of 245 nm to 270 nm for an aqueous solution containing 300 mg of the alkylated cyclodextrin composition per mL of solution in a cell having a 1 cm path length; and combining the alkylated cyclodextrin composition with an active agent. In some embodiments, said absorption of less than 1 A.U. is due to a drug degrading agent.

The present invention is also directed to a method for stabilizing an active agent, the method comprising providing an alkylated cyclodextrin composition comprising an alkylated cyclodextrin, less than 500 ppm of a phosphate, and less than 0.5% of a chloride, wherein the alkylated cyclodextrin composition has an absorption of less than 1 A.U., as determined by UV/vis spectrophotometry at a wavelength of 245 nm to 270 nm for an aqueous solution containing 300 mg of the alkylated cyclodextrin composition per mL of solution in a cell having a 1 cm path length; and combining the alkylated cyclodextrin composition with an active agent. In some embodiments, said absorption of less than 1 A.U. is due to a color forming agent.

The method of stabilizing an active agent can be performed wherein the composition comprising one or more active agents and an alkylated cyclodextrin composition comprising an alkylated cyclodextrin and less than 500 ppm of a phosphate is present as a dry solution, a wet solution, an inhalable composition, a parenteral composition, a solid solution, a solid mixture, a granulate, a gel, and other active agent compositions known to persons of ordinary skill in the art.

In some embodiments, the method of stabilizing an active agent provides 2% or less, 1.5% or less, 1% or less, or 0.5% or less of a drug-degrading agent or color-forming agent after the composition comprising one or more active agents and an alkylated cyclodextrin composition comprising an alkylated cyclodextrin and less than 500 ppm of a phosphate is maintained at a temperature of 80° C. for a period of 120 minutes.

In some embodiments, the method of stabilizing an active agent provides 2% or less, 1.9% or less, 1.8% or less, 1.7% or less, 1.6% or less, 1.5% or less, 1.4% or less, 1.3% or less, 1.2% or less, 1.1% or less, 1% or less, 0.9% or less, 0.8% or less, 0.7% or less, 0.6% or less, 0.5% or less, 0.4% or less, 0.3% or less, 0.2% or less, or 0.1% or less of a chloride after the composition comprising one or more active agents and an alkylated cyclodextrin composition comprising an alkylated cyclodextrin and less than 500 ppm of a phosphate is maintained at a temperature of 80° C. for a period of 120 minutes.

Similarly, in some embodiments, the method of stabilizing an active agent provides an active agent assay of 98% or more, 98.5% or more, 99% or more, or 99.5% or more of the active agent after the composition comprising one or more active agents and an alkylated cyclodextrin composition comprising an alkylated cyclodextrin and less than 500 ppm of a phosphate is maintained at a temperature of 80° C. for a period of 120 minutes.

In some embodiments, the method of stabilizing provides an alkylated cyclodextrin composition comprising an alkylated cyclodextrin with a phosphate level of less than 400 ppm, less than 300 ppm, less than 200 ppm, less than 125 ppm, less than 100 ppm, less than 75 ppm, or less than 50 ppm.

In some embodiments, the method of stabilizing provides an alkylated cyclodextrin composition comprising an alkylated cyclodextrin wherein the alkylated cyclodextrin composition has an absorption of 0.5 A.U. or less, as determined by UV/vis spectrophotometry at a wavelength of 245 nm to 270 nm for an aqueous solution containing 300 mg of the alkylated cyclodextrin composition per mL of solution in a cell having a 1 cm path length. In some embodiments, said absorption of 0.5 A.U. or less is due to a drug degrading agent.

Generally, the alkylated cyclodextrin is present in an amount sufficient to stabilize the active agent. An amount sufficient can be a molar ratio of 0.1:1 to 10:1, 0.5:1 to 10:1, 0.8:1 to 10:1, or 1:1 to 5:1 (alkylated cyclodextrin:active agent).

A cyclodextrin in the combination composition need not bind with another material, such as an active agent, present in a formulation containing it. However, if a cyclodextrin binds with another material, such a bond can be formed as a result of an inclusion complexation, an ion pair formation, a hydrogen bond, and/or a Van der Waals interaction.

An anionic derivatized cyclodextrin can complex or otherwise bind with an acid-ionizable agent. As used herein, the term acid-ionizable agent is taken to mean any compound that becomes or is ionized in the presence of an acid. An acid-ionizable agent comprises at least one acid-ionizable functional group that becomes ionized when exposed to acid or when placed in an acidic medium. Exemplary acid-ionizable functional groups include a primary amine, secondary amine, tertiary amine, quaternary amine, aromatic amine, unsaturated amine, primary thiol, secondary thiol, sulfonium, hydroxyl, enol and others known to those of ordinary skill in the chemical arts.

The degree to which an acid-ionizable agent is bound by non-covalent ionic binding versus inclusion complexation formation can be determined spectrometrically using methods such as $^1$H-NMR, $^{13}$C-NMR, or circular dichroism, for example, and by analysis of the phase solubility data for the acid-ionizable agent and anionic derivatized cyclodextrin. The artisan of ordinary skill in the art will be able to use these conventional methods to approximate the amount of each type of binding that is occurring in solution to determine whether or not binding between the species is occurring predominantly by non-covalent ionic binding or inclusion complex formation. Under conditions where non-covalent ionic bonding predominates over inclusion complex formation, the amount of inclusion complex formation, measured by NMR or circular dichroism, will be reduced even though the phase solubility data indicates significant binding between the species under those conditions; moreover, the intrinsic solubility of the acid-ionizable agent, as determined from the phase solubility data, will generally be higher than expected under those conditions.

As used herein, the term "non-covalent ionic bond" refers to a bond formed between an anionic species and a cationic species. A bond is non-covalent such that the two species together form a salt or ion pair. An anionic derivatized cyclodextrin provides the anionic species of the ion pair and the acid-ionizable agent provides the cationic species of the ion pair. Since an anionic derivatized cyclodextrin is multivalent, an alkylated cyclodextrin can form an ion pair with one or more acid-ionizable or otherwise cationic agents.

A liquid formulation of the invention can be converted to a solid formulation for reconstitution. A reconstitutable solid composition according to the invention comprises an active agent, a derivatized cyclodextrin and optionally at least one other pharmaceutical excipient. A reconstitutable composition can be reconstituted with an aqueous liquid to form a liquid formulation that is preserved. The composition can comprise an admixture (minimal to no presence of an inclusion complex) of a solid derivatized cyclodextrin and an active agent-containing solid and optionally at least one solid pharmaceutical excipient, such that a major portion of the active agent is not complexed with the derivatized cyclodextrin prior to reconstitution. Alternatively, the composition can comprise a solid mixture of a derivatized cyclodextrin and an active agent, wherein a major portion of the active agent is complexed with the derivatized cyclodextrin prior to reconstitution. A reconstitutable solid composition can also comprise a derivatized cyclodextrin and an active agent where substantially all or at least a major portion of the active agent is complexed with the derivatized cyclodextrin.

A reconstitutable solid composition can be prepared according to any of the following processes. A liquid formulation of the invention is first prepared, then a solid is formed by lyophilization (freeze-drying), spray-drying, spray freeze-drying, antisolvent precipitation, aseptic spray drying, various processes utilizing supercritical or near supercritical fluids, or other methods known to those of ordinary skill in the art to make a solid for reconstitution.

A liquid vehicle included in a formulation of the invention can comprise an aqueous liquid carrier (e.g., water), an aqueous alcohol, an aqueous organic solvent, a non-aqueous liquid carrier, and combinations thereof.

The formulation of the present invention can include one or more pharmaceutical excipients such as a conventional preservative, antifoaming agent, antioxidant, buffering agent, acidifying agent, alkalizing agent, bulking agent, colorant, complexation-enhancing agent, cryoprotectant, electrolyte, glucose, emulsifying agent, oil, plasticizer, solubility-enhancing agent, stabilizer, tonicity modifier, flavors, sweeteners, adsorbents, antiadherent, binder, diluent, direct compression excipient, disintegrant, glidant, lubricant, opaquant, polishing agent, complexing agents, fragrances, other excipients known by those of ordinary skill in the art for use in formulations, combinations thereof.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids and trolamine and others known to those of ordinary skill in the art.

As used herein, the term "acidifying agent" is intended to mean a compound used to provide an acidic medium for product stability. Such compounds include, by way of example and without limitation, acetic acid, acidic amino acids, citric acid, fumaric acid and other α-hydroxy acids, hydrochloric acid, ascorbic acid, phosphoric acid, sulfuric acid, tartaric acid and nitric acid and others known to those of ordinary skill in the art.

As used herein, the term "antiadherent" is intended to mean an agent that prevents the sticking of solid dosage formulation ingredients to punches and dies in a tableting machine during production. Such compounds include, by way of example and without limitation, magnesium stearate, talc, calcium stearate, glyceryl behenate, polyethylene glycol, hydrogenated vegetable oil, mineral oil, stearic acid and other materials known to one of ordinary skill in the art.

As used herein, the term "binder" is intended to mean a substance used to cause adhesion of powder particles in solid dosage formulations. Such compounds include, by way of example and without limitation, acacia, alginic acid, carboxymethylcellulose sodium, poly(vinylpyrrolidone), a compressible sugar, ethylcellulose, gelatin, liquid glucose, methylcellulose, povidone and pregelatinized starch and other materials known to one of ordinary skill in the art.

When needed, binders can also be included in the dosage forms. Exemplary binders include acacia, tragacanth, gelatin, starch, cellulose materials such as methyl cellulose and sodium carboxymethylcellulose, alginic acids and salts thereof, polyethylene glycol, guar gum, polysaccharide, bentonites, sugars, invert sugars, poloxamers (PLURONIC™ F68, PLURONIC™ F127), collagen, albumin, gelatin, cellulosics in non-aqueous solvents, combinations thereof and others known to those of ordinary skill in the art. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, a conventional preservative is a compound used to at least reduce the rate at which bioburden increases, but maintains bioburden steady or reduces bioburden after contamination. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl or butyl parabens and others known to those of ordinary skill in the art. It is understood that some preservatives can interact with the alkylated cyclodextrin thus reducing the preservative effectiveness. Nevertheless, by adjusting the choice of preservative and the concentrations of preservative and the alkylated cyclodextrin adequately preserved formulations can be found.

As used herein, the term "diluent" or "filler" is intended to mean an inert substance used as a filler to create the desired bulk, flow properties, and compression characteristics in the preparation of a liquid or solid dosage form. Such compounds include, by way of example and without limitation, a liquid vehicle (e.g., water, alcohol, solvents, and the like), dibasic calcium phosphate, kaolin, lactose, dextrose, magnesium carbonate, sucrose, mannitol, microcrystalline cellulose, powdered cellulose, precipitated calcium carbonate, sorbitol, and starch and other materials known to one of ordinary skill in the art.

As used herein, the term "direct compression excipient" is intended to mean a compound used in compressed solid dosage forms. Such compounds include, by way of example and without limitation, dibasic calcium phosphate, and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, acetone, potassium metabisulfite, potassium sulfite, ascorbic acid, ascorbyl palmitate, citric acid, butylated hydroxyanisole, butylated hydroxytoluene, hypophosphorous acid, monothioglycerol, propyl gallate, sodium ascorbate, sodium citrate, sodium sulfide, sodium sulfite, sodium bisulfate, sodium formaldehyde sulfoxylate, thioglycolic acid, EDTA, pentetate, and sodium metabisulfite and others known to those of ordinary skill in the art.

As used herein, the term "buffering agent" is intended to mean a compound used to resist change in pH upon dilution or addition of acid or alkali. Such compounds include, by way of example and without limitation, acetic acid, sodium acetate, adipic acid, benzoic acid, sodium benzoate, boric acid, sodium borate, citric acid, glycine, maleic acid, monobasic sodium phosphate, dibasic sodium phosphate, 4-(2-hydroxyethyl)-1-piperazineethanesulfonic acid, lactic acid, tartaric acid, potassium metaphosphate, potassium phosphate, monobasic sodium acetate, sodium bicarbonate, tris, sodium tartrate and sodium citrate anhydrous and dihydrate and others known to those of ordinary skill in the art.

A complexation-enhancing agent can be added to a formulation of the invention. When such an agent is present, the ratio of cyclodextrin/active agent can be changed. A complexation-enhancing agent is a compound, or compounds, that enhance(s) the complexation of the active agent with the cyclodextrin. Suitable complexation enhancing agents include one or more pharmacologically inert water-soluble polymers, hydroxy acids, and other organic compounds typically used in preserved formulations to enhance the complexation of a particular agent with cyclodextrins.

Hydrophilic polymers can be used as complexation-enhancing, solubility-enhancing and/or water activity reducing agents to improve the performance of formulations containing a CD-based preservative. Loftsson has disclosed a number of polymers suitable for combined use with a cyclodextrin (underivatized or derivatized) to enhance the performance and/or properties of the cyclodextrin. Suitable polymers are disclosed in *Pharmazie* 56:746 (2001); *Int. J. Pharm.* 212:29 (2001); Cyclodextrin: From Basic Research to Market, 10th Int'l Cyclodextrin Symposium, Ann Arbor, Mich., US, May 21-24, p. 10-15 (2000); PCT Int'l Pub. No. WO 99/42111; *Pharmazie* 53:733 (1998); *Pharm. Technol. Eur.* 9:26 (1997); *J. Pharm. Sci.* 85:1017 (1996); European Patent Appl. No. 0 579 435; Proc. of the 9th Int'l Symposium on Cyclodextrins, Santiago de Comostela, E S, May 31-Jun. 3, 1998, pp. 261-264 (1999); *S.T.P. Pharma Sciences* 9:237 (1999); *Amer. Chem. Soc. Symposium Series* 737 (Polysaccharide Applications): 24-45 (1999); *Pharma. Res.* 15:1696 (1998); *Drug Dev. Ind. Pharm.* 24:365 (1998); *Int. J. Pharm.* 163:115 (1998); Book of Abstracts, 216th Amer. Chem. Soc. Nat'l Meeting, Boston, August 23-27 CELL-016 (1998); *J. Controlled Release* 44:95 (1997); *Pharm. Res.* (1997) 14(11), 5203; *Invest. Ophthalmol. Vis. Sci.* 37:1199 (1996); Proc. of the 23rd Int'l Symposium on Controlled Release of Bioactive Materials 453-454 (1996); *Drug Dev. Ind. Pharm.* 22:401 (1996); Proc. of the 8th Int'l Symposium on Cyclodextrins, Budapest, H U, Mar. 31-Apr. 2, 1996, pp. 373-376 (1996); *Pharma. Sci.* 2:277 (1996); *Eur. J. Pharm. Sci.* 4S:S144 (1996); 3rd Eur. Congress of Pharma. Sci. Edinburgh, Scotland, UK Sep. 15-17, 1996; *Pharmazie* 51:39 (1996); *Eur. J. Pharm. Sci.* 4S:S143 (1996); U.S. Pat. Nos. 5,472,954 and 5,324,718; *Int. J. Pharm.* 126:73 (1995); Abstracts of Papers of the Amer. Chem. Soc. 209:33-CELL (1995); *Eur. J. Pharm. Sci.* 2:297 (1994); *Pharm. Res.* 11:S225 (1994); *Int. J. Pharm.* 104:181

(1994); and *Int. J. Pharm.* 110:169 (1994), the entire disclosures of which are hereby incorporated by reference in their entirety.

Other suitable polymers are well-known excipients commonly used in the field of pharmaceutical formulations and are included in, for example, *Remington's Pharmaceutical Sciences*, 18th ed., pp. 291-294, A. R. Gennaro (editor), Mack Publishing Co., Easton, Pa. (1990); A. Martin et al., *Physical Pharmacy. Physical Chemical Principles in Pharmaceutical Sciences*, 3d ed., pp. 592-638 (Lea & Febinger, Philadelphia, Pa. (1983); A. T. Florence et al., Physicochemical Principles of Pharmacy, 2d ed., pp. 281-334, MacMillan Press, London, UK (1988), the disclosures of which are incorporated herein by reference in their entirety. Still other suitable polymers include water-soluble natural polymers, water-soluble semi-synthetic polymers (such as the water-soluble derivatives of cellulose) and water-soluble synthetic polymers. The natural polymers include polysaccharides such as inulin, pectin, algin derivatives (e.g. sodium alginate) and agar, and polypeptides such as casein and gelatin. The semi-synthetic polymers include cellulose derivatives such as methylcellulose, hydroxyethylcellulose, hydroxypropylcellulose, their mixed ethers such as hydroxypropylmethylcellulose and other mixed ethers such as hydroxyethyl-ethylcellulose and hydroxypropylethylcellulose, hydroxypropylmethylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Other natural, semi-synthetic and synthetic polymers not named here which meet the criteria of water solubility, pharmaceutical acceptability and pharmacological inactivity are likewise considered to be within the ambit of the present invention.

As used herein, a fragrance is a relatively volatile substance or combination of substances that produces a detectable aroma, odor or scent. Exemplary fragrances include those generally accepted as safe by the U.S. Food and Drug Administration.

As used herein, the term "glidant" is intended to mean an agent used in solid dosage formulations to promote flowability of the solid mass. Such compounds include, by way of example and without limitation, colloidal silica, cornstarch, talc, calcium silicate, magnesium silicate, colloidal silicon, tribasic calcium phosphate, silicon hydrogel and other materials known to one of ordinary skill in the art.

As used herein, the term "lubricant" is intended to mean a substance used in solid dosage formulations to reduce friction during compression. Such compounds include, by way of example and without limitation, calcium stearate, magnesium stearate, polyethylene glycol, talc, mineral oil, stearic acid, and zinc stearate and other materials known to one of ordinary skill in the art.

As used herein, the term "opaquant" is intended to mean a compound used to render a coating opaque. An opaquant can be used alone or in combination with a colorant. Such compounds include, by way of example and without limitation, titanium dioxide, talc and other materials known to one of ordinary skill in the art.

As used herein, the term "polishing agent" is intended to mean a compound used to impart an attractive sheen to solid dosage forms. Such compounds include, by way of example and without limitation, carnauba wax, white wax and other materials known to one of ordinary skill in the art.

As used herein, the term "disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, bentonite, microcrystalline cellulose (e.g., AVICEL®), carboxymethylcellulose calcium, croscarmellose sodium, alginic acid, sodium alginate, cellulose polacrilin potassium (e.g., AMBERLITE®), alginates, sodium starch glycolate, gums, agar, guar, locust bean, karaya, pectin, tragacanth, crospovidone and other materials known to one of ordinary skill in the art.

As used herein, the term "stabilizer" is intended to mean a compound used to stabilize the therapeutic agent against physical, chemical, or biochemical process which would reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and other known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those of ordinary skill in the art. In some embodiments, the tonicity of the liquid formulation approximates the tonicity of blood or plasma.

As used herein, the term "antifoaming agent" is intended to mean a compound or compounds that prevents or reduces the amount of foaming that forms on the surface of the liquid formulation. Suitable antifoaming agents include dimethicone, simethicone, octoxynol and others known to those of ordinary skill in the art.

As used herein, the term "bulking agent" is intended to mean a compound used to add bulk to the solid product and/or assist in the control of the properties of the formulation during lyophilization. Such compounds include, by way of example and without limitation, dextran, trehalose, sucrose, polyvinylpyrrolidone, lactose, inositol, sorbitol, dimethylsulfoxide, glycerol, albumin, calcium lactobionate, and others known to those of ordinary skill in the art.

As used herein, the term "cryoprotectant" is intended to mean a compound used to protect an active therapeutic agent from physical or chemical degradation during lyophilization. Such compounds include, by way of example and without limitation, dimethyl sulfoxide, glycerol, trehalose, propylene glycol, polyethylene glycol, and others known to those of ordinary skill in the art.

As used herein, the term "emulsifier" or "emulsifying agent" is intended to mean a compound added to one or more of the phase components of an emulsion for the purpose of stabilizing the droplets of the internal phase within the external phase. Such compounds include, by way of example and without limitation, lecithin, polyoxylethylene-polyoxypropylene ethers, polyoxylethylene-sorbitan monolaurate, polysorbates, sorbitan esters, stearyl alcohol, tyloxapol, tragacanth, xanthan gum, acacia, agar, alginic acid, sodium alginate, bentonite, carbomer, sodium carboxymethylcellulose, cholesterol, gelatin, hydroxyethyl cellulose, hydroxypropyl cellulose, octoxynol, oleyl alcohol, polyvinyl alcohol, povidone, propylene glycol monostearate, sodium lauryl sulfate, and others known to those of ordinary skill in the art.

A solubility-enhancing agent can be added to the formulation of the invention. A solubility-enhancing agent is a compound, or compounds, that enhance(s) the solubility of the active agent when in a liquid formulation. When such an agent is present, the ratio of cyclodextrin/active agent can be changed. Suitable solubility enhancing agents include one or more organic solvents, detergents, soaps, surfactant and other organic compounds typically used in parenteral formulations to enhance the solubility of a particular agent.

Suitable organic solvents include, for example, ethanol, glycerin, polyethylene glycols, propylene glycol, poloxomers, and others known to those of ordinary skill in the art.

Formulations comprising the alkylated cyclodextrin composition of the invention can include oils (e.g., fixed oils, peanut oil, sesame oil, cottonseed oil, corn oil olive oil, and the like), fatty acids (e.g., oleic acid, stearic acid, isostearic acid, and the like), fatty acid esters (e.g., ethyl oleate, isopropyl myristate, and the like), fatty acid glycerides, acetylated fatty acid glycerides, and combinations thereof. Formulations comprising the alkylated cyclodextrin composition of the invention can also include alcohols (e.g., ethanol, iso-propanol, hexadecyl alcohol, glycerol, propylene glycol, and the like), glycerol ketals (e.g., 2,2-dimethyl-1,3-dioxolane-4-methanol, and the like), ethers (e.g., poly (ethylene glycol) 450, and the like), petroleum hydrocarbons (e.g., mineral oil, petrolatum, and the like), water, surfactants, suspending agents, emulsifying agents, and combinations thereof.

It should be understood, that compounds used in the art of pharmaceutical formulations generally serve a variety of functions or purposes. Thus, if a compound named herein is mentioned only once or is used to define more than one term herein, its purpose or function should not be construed as being limited solely to that named purpose(s) or function(s).

Formulations comprising the alkylated cyclodextrin composition of the invention can also include biological salt(s), sodium chloride, potassium chloride, and other electrolyte(s).

Since some active agents are subject to oxidative degradation, a liquid formulation according to the invention can be substantially oxygen-free. For example, the headspace of a container containing a liquid formulation can made oxygen-free, substantially oxygen-free, or oxygen-reduced by purging the headspace with an inert gas (e.g., nitrogen, argon, carbon dioxide, and the like), or by bubbling an inert gas through a liquid formulation. For long-term storage, a liquid formulation containing an active agent subject to oxidative degradation can be stored in an oxygen-free or oxygen-reduced environment. Removal of oxygen from the formulation will enhance preservation of the formulation against aerobic microbes; whereas, addition of oxygen to the formulation will enhance preservation against anaerobic microbes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "patient" or "subject" are taken to mean warm blooded animals such as mammals, for example, cats, dogs, mice, guinea pigs, horses, bovine cows, sheep, non-humans, and humans.

A formulation of the invention will comprise an active agent present in an effective amount. By the term "effective amount," is meant the amount or quantity of active agent that is sufficient to elicit the required or desired response, or in other words, the amount that is sufficient to elicit an appreciable biological response when administered to a subject.

The compositions of the present invention can be present in formulations for dosage forms such as a reconstitutable solid, tablet, capsule, pill, troche, patch, osmotic device, stick, suppository, implant, gum, effervescent composition, injectable liquid, ophthalmic or nasal solutions, or inhalable powders or solutions.

The invention also provides methods of preparing a liquid formulation comprising one or more active agents and an alkylated cyclodextrin composition, wherein the alkylated cyclodextrin composition comprises an alkylated cyclodextrin and less than 500 ppm of a phosphate. A first method comprises: forming a first aqueous solution comprising an alkylated cyclodextrin composition; forming a second solution or suspension comprising one or more active agents; and mixing the first and second solutions to form a liquid formulation. A similar second method comprises adding one or more active agents directly to a first solution without formation of the second solution. A third method comprises adding an alkylated cyclodextrin composition directly to the a solution/suspension containing one or more active agents. A fourth method comprises adding a solution comprising one or more active agents to a powdered or particulate alkylated cyclodextrin composition. A fifth method comprises adding one or more active agents directly to a powdered or particulate alkylated cyclodextrin composition, and adding the resulting mixture to a second solution. A sixth method comprises creating a liquid formulation by any of the above methods and then isolating a solid material by lyophilization, spray-drying, aseptic spray drying, spray-freeze-drying, antisolvent precipitation, a process utilizing a supercritical or near supercritical fluid, or another method known to those of ordinary skill in the art to make a powder for reconstitution.

Specific embodiments of the methods of preparing a liquid formulation include those wherein: 1) the method further comprises sterile filtering the formulation using a filtration medium having a pore size of 0.1 μm or larger; 2) the liquid formulation is sterilized by irradiation or autoclaving; 3) the method further comprises isolating a solid from the solution; 4) the solution is purged with nitrogen or argon or other inert pharmaceutically acceptable gas such that a substantial portion of the oxygen dissolved in, and/or in surface contact with, the solution is removed.

The invention also provides a reconstitutable solid pharmaceutical composition comprising one or more active agents, an alkylated cyclodextrin composition and optionally at least one other pharmaceutical excipient. When this composition is reconstituted with an aqueous liquid to form a preserved liquid formulation, it can be administered by injection, infusion, topically, by inhalation or orally to a subject.

Some embodiments of the reconstitutable solid pharmaceutical composition includes those wherein: 1) the pharmaceutical composition comprises an admixture of an alkylated cyclodextrin composition and a solid comprising one or more active agents and optionally at least one solid pharmaceutical excipient, such that a major portion of the active agent is not complexed with an alkylated cyclodextrin prior to reconstitution; and/or 2) the composition comprises a solid mixture of an alkylated cyclodextrin composition and one or more active agents, wherein a major portion of the one or more active agents is complexed with the alkylated cyclodextrin prior to reconstitution.

A composition of the invention can be used in a pharmaceutical dosage form, pharmaceutical composition or other such combination of materials. These alkylated cyclodextrin compositions are also useful as, but not limited to, analytical reagents, food and cosmetics adjuvants and/or additives, and as environmental clean-up agents.

In view of the above description and the examples below, one of ordinary skill in the art will be able to practice the invention as claimed without undue experimentation. The foregoing will be better understood with reference to the following examples that detail certain procedures for the preparation of molecules, compositions, and formulations according to the present invention. All references made to these examples are for the purposes of illustration. The following examples should not be considered exhaustive, but merely illustrative of only a few of the many embodiments contemplated by the present invention.

EXAMPLES

Example 1

Determination of Active Agent Solubility

Comparative evaluation of the solubilization effect of various sulfoalkyl ether cyclodextrin compositions on pharmaceutical active agents was determined as follows. A 0.04 M stock solutions of each selected cyclodextrin was prepared with purified water. Clarity of solutions was determined by visual inspection or instrumentally. A clear solution is at least clear by visual inspection with the unaided eye. Each pharmaceutical active agent, tested in duplicate, was combined with 2 mL or 4 mL of a SAE-CD aqueous solution.

Pharmaceutical active agents were weighed in amounts in excess of their anticipated solubility, and placed in TEFLON®-lined screw-capped vials. The active agents were present in amounts of at least 3 mg/mL. Each vial was then filled with the appropriate amount of cyclodextrin solution (either 2 mL or 4 mL). The vials were vortexed and sonicated to aid in wetting the solids with the fluid. The vials were then placed on a lab quake or a roller mixer for equilibration. The vials were visually inspected periodically to assure that the solids were adequately being wetted and in contact with the fluid. The fluid within the vials was then sampled periodically to determine the concentration of the pharmaceutical active agent present in solution. Samples were typically measured at 24 hour intervals.

Sampling of the vials to determine active agent solubility was performed by decanting 1 mL of solution from the vial followed by optional centrifuging. The removed supernatant was then filtered using a 0.22 μm syringe filter, and diluted with the mobile phase to an appropriate concentration within the standard curve. The samples were then analyzed by HPLC to determine concentration of the solubilized drug derivatives.

Example 2

Determination of Moisture Content

The following procedure was used to evaluate the moisture content of the alkylated cyclodextrins. Determinations were performed in duplicate on 250 mg of each using a Brinkman Karl-Fischer Coulometer (Brinkman Instruments Co., IL). A known weight of solid cyclodextrin was added to the Karl-Fischer Coulometer and the total amount of water in the sample is measured. The total amount of water present is then converted to a percentage of the solid to give the percent moisture content of the sample.

Example 3

Analysis by Capillary Electrophoresis

The following procedure was used to analyze the SAE-CD derivative compositions by capillary electrophoresis. A Beckman P/ACE 2210 capillary electrophoresis system coupled with a UV absorbance detector (Beckman Instruments, Inc., Fullereton, Calif.) was used to analyze solutions of SBE-β-CD and SBE-γ-CD derivatives. The separations were performed at 25° C. using a fused silica capillary (having a 50 μm inner diameter, a total length of 57 cm, and an effective length of 50 cm) with a pH adjusted running buffer of 30 mM benzoic acid and 100 mM TRIS (tris-hydroxymethyl-aminomethanol).

The capillary was treated with the following wash sequence before each injection: water, 0.01 N NaOH, and running buffer. The detector was set at 214 nm. The voltage was 30 kV. Samples were introduced by pressure injections: 20 seconds at 0.5 psi.

Example 4

An α-CD derivative composition having a monomodal distribution profile can be prepared according to Example 5 or any of the literature methods cited herein, except that α-CD would be used in place of the β-CD or γ-CD. An exemplary SBE-α-CD is made using the following procedure, wherein an α-cyclodextrin in an alkaline aqueous medium is derivatized with an SBE precursor to form the SBE-α-CD. The α-CD is dissolved in NaOH aqueous solution, heated to 70° C., and stirred until complete dissolution. Once dissolution is complete the reaction temperature is increased to between 70° C. to 75° C. Then, 1,4-butanesultone was added over a period of at least 30 minutes. The pH is monitored during the first 4 hours and the reaction is allowed to continue at 70° C. for at least an additional 16 hours. The reaction mixture is cooled and diluted with water (roughly one third the total reaction volume). The solution is further treated with carbon (0.07 gram of carbon/gram of cyclodextrin), neutralized with HCl to pH 6-6.5 and filtered through a 0.45 μm filter. The solution is purified by ultrafiltration using a 650 MWCO membrane. The ultrafiltration end point is determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution is filtered through a 0.22 μm filter and neutralized (pH 6-6.5). The resulting solution is concentrated to roughly a 50% solution by rotary evaporation at between 50° C. to 60° C. under less than 30 mmHg vacuum. The solution is freeze-dried to yield a SBE-α-CD white solid.

Example 5

$SBE_{6.6}$-β-CD Synthesis

A $SBE_{6.6}$-β-CD composition was synthesized according to the following procedure, in which a β-cyclodextrin in an alkaline aqueous medium was derivatized with an SBE precursor to form the $SBE_{6.6}$-β-CD. An aqueous solution of sodium hydroxide was prepared by charging 61.8 kg of sodium hydroxide to 433 kg of water for a 12.5% w/w solution. The reactor contents were heated to between 40° C. to 50° C. before beginning the addition of 270 kg of β-CD over 30 to 60 minutes. The reaction temperature was adjusted to between 65° C. to 95° C. before the addition of 259 kg of 1,4-butane sultone over 30 to 60 minutes. Over the next 6 hours the pH of the solution was maintained above 9 using an aqueous solution of sodium hydroxide. Following the reaction an additional 13.5 kg of sodium hydroxide as a 20% solution was charged to the reaction. The contents were maintained at between 70° C. to 80° C. until the residual level of 1,4-butane sultone was sufficiently low. The contents were cooled to less than 30° C. and the reaction solution was adjusted to pH 6.5-7.5 with aqueous solution of hydrochloric acid. This process yielded 350 to 450 kg of SAE-CD.

Example 6

$SBE_{6.6}$-β-CD Diafiltration and Ultrafiltration

The $SBE_{6.6}$-β-CD of Example 5 was purified by the following procedure. The reaction solution was diluted with 800 kg of water. The solution was transferred and further diluted with 500 kg of water. Diafiltration was initiated using a Millipore Helicon Automated Ultrafiltration System using 1000 MWCO spiral wound regenerated cellulose membranes having at least 750 ft$^2$ of membrane area and maintaining a constant solution volume (±1%) until a sample of the returnate has 25 ppm or less of sodium chloride. The solution was concentrated by ultrafiltration until an appropriate solution mass was achieved.

Example 7

$SBE_{6.6}$-β-CD Carbon Processing of the Present Invention

Following the diafiltration and ultrafiltration in Example 6, the $SBE_{6.6}$-β-CD was carbon purified by the following procedure. A column was charged with 32 kg (about 11-12% wt. (11.8-12% wt.) of the starting amount of β-cyclodextrin) of SHIRASAGI®DC32 granular activated carbon and washed thoroughly with water until the wash samples have a constant conductivity. The ratio of $SBE_{6.6}$-β-CD to activated carbon was about 8.4:1 to 8.5:1 (about 8.44:1). Once washed, the reaction solution was passed (recycled) through the carbon for at least 2 hours to complete a first treatment cycle.

A second column was charged with 32 kg (about 11-12% wt. of the starting amount of β-cyclodextrin) of SHIRASAGI® DC32 granular activated carbon and washed thoroughly with water until the wash samples have a constant conductivity. Once washed, the reaction solution was passed through the carbon for at least 2 hours to complete a second treatment cycle.

Example 8

$SBE_{6.6}$-β-CD Concentration and Isolation

The carbon-treated $SBE_{6.6}$-β-CD solutions prepared in Example 7 were concentrated and isolated using the following procedure: a $SBE_{6.6}$-β-CD solution was filtered through 0.65 μm and 0.22 μm filters and then concentrated at a reduced pressure of −0.6 bar to −0.7 bar at a temperature of 65° C. to 72° C., with agitation at 70 rpm to 100 rpm, until a solution having a $SBE_{6.6}$-β-CD concentration of 50% w/w was achieved. The concentrated solution was cooled to below 60° C., and then filtered through 0.65 μm and 0.22 μm filters. The filtered solution was then spray dried using a fluidized spray dryer ("FSD") system at an inlet temperature of 170° C., an initial pressure of 20 bar, and chambers 1-3 having set points of 125° C., 105° C., and 100° C., respectively.

Example 9

Determination of Cyclodextrin Substitution Pattern by $^1$H-NMR, $^{13}$C-NMR, COSY-NMR and HMQC on a Bruker AVANCE® 400 or 500 Instrument in $D_2O$ Solutions Determination of the substitution pattern is conducted according to the method of Example 6 of WO 2005/042584, the relevant disclosures of which are hereby incorporated by reference.

Example 10

$SBE_{66}$-O-CD Comparative Carbon Processing

An exemplary $SBE_{6.6}$-β-CD was carbon purified by the following procedure: a column was charged with 32 kg (about 11-12% wt. (11.8-12% wt.) of the starting amount of β-cyclodextrin in Example 5) of SHIRASAGI® DC32 granular activated carbon and washed thoroughly with water until the wash samples have a constant conductivity. Once washed the reaction solution was passed through the carbon for at least 2 hours.

Example 11

$SBE_{6.6}$-β-CD Impurity Analysis I $SBE_{6.6}$-β-CD samples treated either once or twice with activated carbon according to Examples 10 and 7, respectively, concentrated and isolated by the process described in Example 8, were then analyzed by UV/vis spectrophotometry. The analysis was performed by dissolving an appropriate amount of $SBE_{6.6}$-β-CD in water (e.g., 0.1 g to 6 g of $SBE_{6.6}$-β-CD, corrected for water content, dissolved in 10 mL of water) to provide solutions containing from 1% to 60% w/w of the derivatized cyclodextrin.

Figure 2:
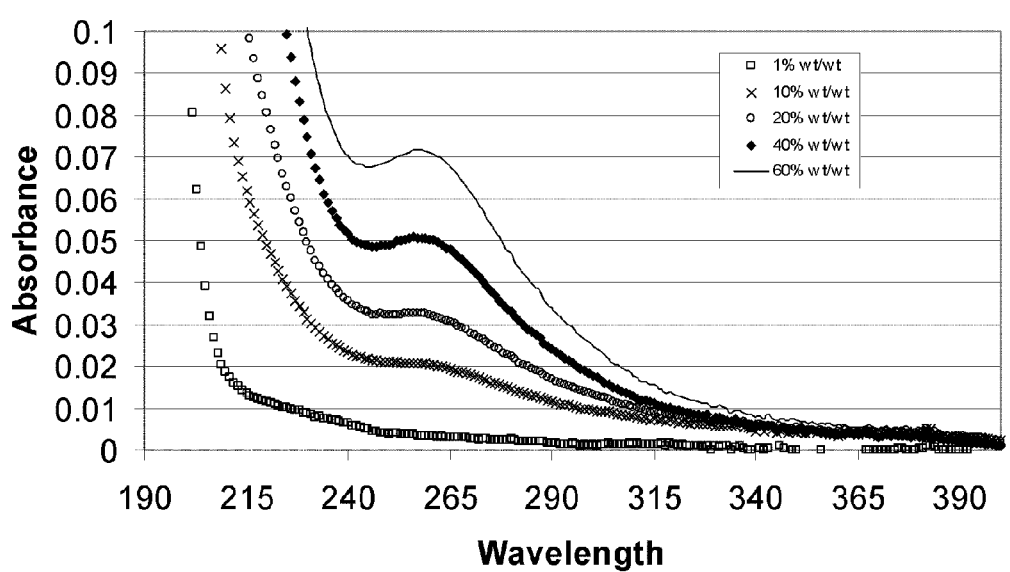
FIG. 2 provides a graphic representation of a UV/vis scan (190 nm to 400 nm) of solutions containing a SAE-CD composition after a second carbon treatment, in which the sulfoalkyl ether cyclodextrin concentration is varied from 1% to 60% by weight.

The carbon-treated cyclodextrin solutions were analyzed on a Perkin Elmer Lambda 35 UV/Vis spectrophotometer, scanning from 190 nm to 400 nm at a speed of 240 nm/min and a slit width of 1.0 nm. The samples were blanked against water before analysis. The UV/vis absorption spectra of various concentrations of $SBE_{6.6}$-β-CD solutions after one and two activated carbon treatments is provided graphically in FIGS. 1 and 2, respectively, which provide a graphic representation of the $SBE_{6.6}$-β-CD lots after one or two carbon treatments analyzed by the UV method. Referring to FIG. 1, the data shows that a higher concentration of impurities having an absorption in the UV/visible region of the spectrum is present when an $SBE_{6.6}$-β-CD solution is treated only once with activated carbon. Referring to FIG. 2, the data show that a second carbon treatment reduces the level of UV/vis absorbing impurities at least five fold or more.

Example 12

SBE$_{6.6}$-β-CD Impurity Analysis II

An exemplary SBE$_{6.6}$-β-CD sample was analyzed by UV/Vis spectrophotometry using the following procedure: a 50% w/w SBE$_{6.6}$-β-CD solution was prepared by dissolving 54.1 grams of SBE$_{6.6}$-β-CD, corrected for water content, in a caustic solution of 12.5 grams of sodium hydroxide in 100 mL of water. The initial solution was analyzed on a PERKIN ELMER Lambda 35 UV/Vis spectrophotometer, scanning from 190 nm to 400 nm at a speed of 240 nm/min and a slit width of 1.0 nm. The sample was blanked against water before analysis. The solution was placed in a 60° C. oven for up to 168 hours. Solution samples were analyzed at 24 hours, 72 hours, 96 hours, and 168 hours.

Figure 3:
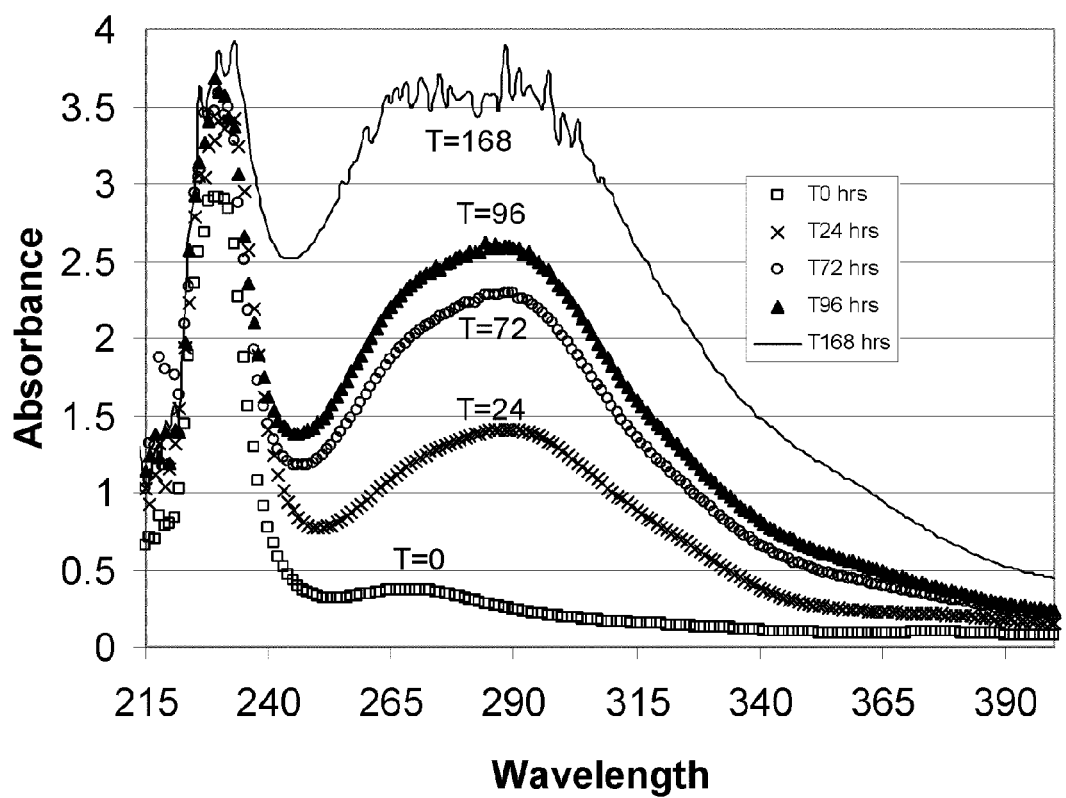
FIG. 3 provides a graphic representation of a UV/vis scan (190 nm to 400 nm) of a $SBE_{6.6}$-β-CD solution after thermal and caustic degradation at a temperature of 60° C. for a period of 0, 24, 72, 96, and 168 hours to demonstrate degradation of β-cyclodextrin and formation of drug-degrading impurities having an absorption at a wavelength of 245 nm to 270 nm and/or color-forming agents having an absorption at a wavelength of 320 nm to 350 nm.

FIG. 3 provides a graphical representation of the results from the thermal and caustic stress on the SBE$_{6.6}$-β-CD compositions. Referring to FIG. 3, the data shows that within 24 hours, a significant absorption at a wavelength of 245 nm to 270 nm has formed, and that this absorption increases with the duration of thermal and caustic exposure. By 168 hours (7 days), the absorption maximum at a wavelength of 245 nm to 270 nm has increased to an equal magnitude with the absorption having a maximum at about 230 nm. Also of note is that the absorption at a wavelength of 320 nm to 350 nm also increases with time of exposure. The data shows that a drug-degrading impurity having an absorption at a wavelength of 245 nm to 270 nm, as well as a color forming agent having an absorption at a wavelength of 320 nm to 350 nm, increase in concentration over time under exposure to heat and/or caustic conditions.

Example 13

Measurements of Color-Forming Agents

SBE$_{6.6}$-β-CD compositions that underwent single- or double-treatment with activated carbon (according to Examples 10 and 7, respectively) were formulated with a triazole antifungal API (posaconazole, which was purchased from Schering-Plough as an aqueous oral suspension, NOXAFIL®). The formulation procedure is provided below.

Aqueous solution samples of a triazole antifungal API (5 mg/mL) and a SBE$_{6.6}$-β-CD composition (100 mM, pH 3) were prepared using SBE$_{6.6}$-β-CD Lot Nos. 17CX01.HQ00044, 17CX01.HQ00037, 17CX01.HQ00035, 17CX01.HQ00033, and 17CX01.HQ00029. All solution samples were filtered through 0.22 μm PVDF filter, and separated into vials. The UV/Vis absorption of a portion of the initial solutions was measured using a 1 cm Hunter cuvette on a PERKIN ELMER Lambda 35 UV/Vis spectrophotometer, scanning from 190 nm to 400 nm at a speed of 240 nm/min and a slit width of 1.0 nm, and analyzed on a Hunter Labs ULTRASCAN® colorimeter using Hunter Labs universal software, version 4.10. The samples were blanked against water before measurement. The remaining portions of samples were then placed into a 60° C. oven for 7 days and then reanalyzed for color changes using the same procedure. The data is shown in the following tables.

| SBE$_{6.6}$-β-CD Initial Solutions: UV/Vis Analysis | | |
|---|---|---|
| 30% SBE$_{6.6}$-β-CD Solutions Lot No. | Carbon Processing Condition | UV analysis (Max Abs @ λ = 245-270 nm) |
| 17CX01.HQ00044 | 2 Granular carbon treatments (SHIRASAGI® DC-32) | 0.05 |
| 17CX01.HQ00037 | 2 Granular carbon treatments (SHIRASAGI® DC-32) | 0.11 |
| 17CX01.HQ00035 | 2 Granular carbon treatments (SHIRASAGI® DC-32) | 0.16 |
| 17CX01.HQ00033 | 1 Granular carbon treatments (SHIRASAGI® DC-32) | 0.25 |
| 17CX01.HQ00029 | 1 Granular carbon treatments (SHIRASAGI® DC-32) | 0.32 |

| SBE$_{6.6}$-β-CD Solution Color Analysis | | | |
|---|---|---|---|
| SBE$_{6.6}$-β-CD (100 mM) | Carbon Processing Cond. | t = 0 (DE) | t = 7 days @ 60° C. (DE) |
| 17CX01.HQ00044 | 2 Granular carbon treatments (SHIRASAGI® DC-32) | 0.08 | 0.01 |
| 17CX01.HQ00037 | 2 Granular carbon treatments (SHIRASAGI® DC-32) | 0.12 | 0.15 |
| 17CX01.HQ00035 | 2 Granular carbon treatments (SHIRASAGI® DC-32) | 0.09 | 0.18 |
| 17CX01.HQ00033 | 1 Granular carbon treatments (SHIRASAGI® DC-32) | 0.2 | 0.41 |
| 17CX01.HQ00029 | 1 Granular carbon treatments (SHIRASAGI® DC-32) | 0.12 | 0.38 |

L = lightness; 100 for perfect white and 0 for black;
a = measures redness when positive, grey when zero, and greenness when negative;
b = measures yellowness when positive, grey when zero, and blueness when negative;
DE = Total Differences $\sqrt{(\Delta L^2 + \Delta a^2 + \Delta b^2)}$ from the Standard

| Triazole API/SBE$_{6.6}$-β-CD Solution Color Analysis | | |
|---|---|---|
| | UV/Vis Analysis (DE) | |
| Formulation | t = 0 (DE) | t = 7 days @ 60° C. (DE) |
| 17CX01.HQ00044 | 0.46 | 4.37 |
| 17CX01.HQ00037 | 0.2 | 3.76 |
| 17CX01.HQ00035 | 0.24 | 4.43 |
| 17CX01.HQ00033 | 0.45 | 5 |
| 17CX01.HQ00029 | 0.36 | 6.26 |

L = lightness; 100 for perfect white and 0 for black;
a = measures redness when positive, grey when zero, and greenness when negative;
b = measures yellowness when positive, grey when zero, and blueness when negative;
DE = Total Differences $\sqrt{(\Delta L^2 + \Delta a^2 + \Delta b^2)}$ from the Standard.

The UV analysis demonstrated that the UV-active impurities present in the initial SBE$_{6.6}$-β-CD composition are much lower when the cyclodextrin composition is treated twice with activated carbon. The Hunter color analysis of the SBE$_{6.6}$-β-CD composition indicated lower DE values for those SBE$_{6.6}$-β-CD lots that were processed using a double activated carbon treatment. Thus, the lower impurity levels in the SBE$_{6.6}$-β-CD composition that was treated twice with activated carbon resulted in reduced formation of color-forming agents.

Example 14

SBE$_{6.6}$-β-CD DS Subjected to Heat then Carbon Treatment

The effect of heating a derivatized cyclodextrin composition of the present invention was studied as follows. The SBE$_{6.6}$-β-CD composition prepared according to Example 5 was dissolved in aqueous solution and analyzed using UV/vis spectrophotometry. Specifically, a 30% w/w β-cyclodextrin solution was prepared by dissolving 70 grams of SBE$_{6.6}$-β-CD Lot No. 17CX01.HQ00044 (corrected for water content) in 230 mL of water. This initial solution was analyzed on a PERKIN ELIMER Lambda 35 UV/Vis spectrophotometer, scanning from 190 nm to 400 nm at a speed of 240 nm/min and a slit width of 1.0 nm. The sample was blanked against water before analysis. The solution was heated with agitation to 70° C. for 48 hours. The solution was cooled to ambient temperature and divided. To each of the divided solutions, pre-washed SHIRASAGI® DC32 granular activated carbon was added. The SBE$_{6.6}$-β-CD solutions were stirred for 3 hours, and then the activated carbon was filtered using a 0.22 PVDF filter. The solutions were analyzed using a PERKIN ELMER Lambda 35 UV/Vis spectrophotometer, scanning from 190 nm to 400 nm at a speed of 240 nm/min and a slit width of 1.0 nm. The samples were blanked against water before analysis.

Figure 4:
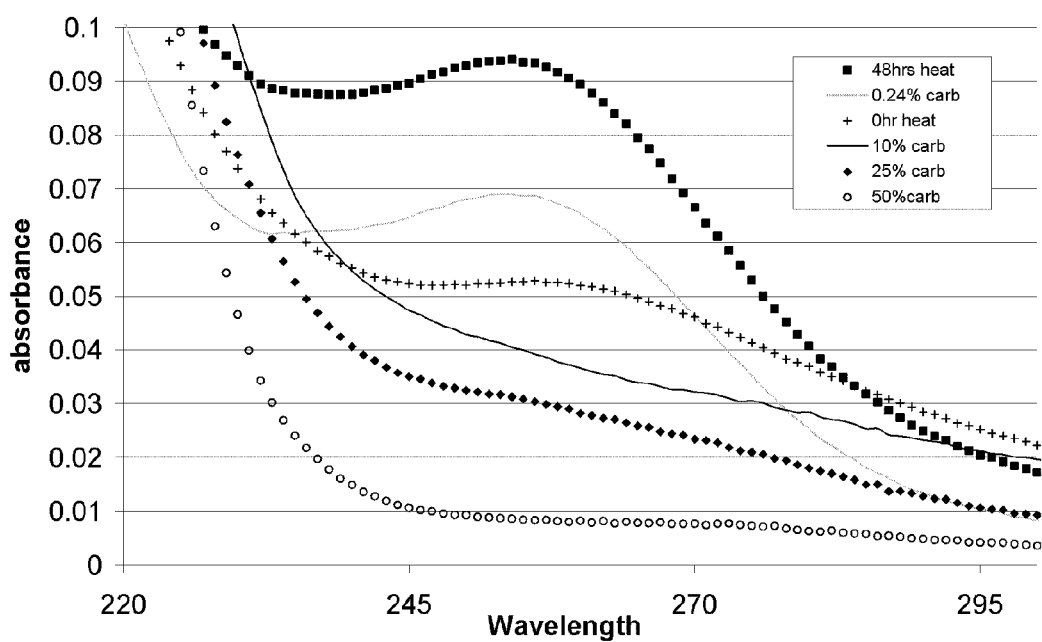
FIG. 4 provides a graphic representation of a UV scan (190 nm to 400 nm) of a solution containing a SAE-β-CD after exposure to a temperature of 70° C. for a period of 48 hours, with subsequent treatment with varying amounts of activated carbon.

The data is depicted graphically in FIG. 4. Referring to FIG. 4, the UV/vis absorption of the solution prior to heat treatment (+ + + +), immediately after 48 hours of heat treatment (■ ■ ■ ■), and after exposure to activated carbon at a loading of 0.24% w/w (• • • • • • • •) 10% w/w (———) 25% w/w (♦ ♦ ♦ ♦), and 50% w/w (□ □ □ □), (according to the concentration of SBE$_{6.6}$-β-CD), is provided. The data show that exposing the SBE$_{6.6}$-β-CD solution to heat for 48 hours resulted in a significant increase (approximately 95%) in the absorption maximum at a wavelength of 245 nm to 270 nm. However, treatment with activated carbon decreases the absorption in this wavelength range. Thus, the drug-degrading impurity having an absorption at a wavelength of 245 nm to 270 nm increases with heating, but can be removed through carbon treatment.

Example 15

SBE$_{6.6}$-β-CD DS and API Stability

Comparative evaluation of various lots of SBE$_{6.6}$-β-CD processed with a single or a double carbon treatment with an antipsychotic API (aripiprazole) were examined by UV/vis spectrophotometry and HPLC analysis. The general procedure used to evaluate the stability of the SBE$_{6.6}$-β-CD/API formulations is provided below.

Aqueous solutions comprising samples of the API (aripiprazole) were prepared with an API concentration of 7.5 mg/mL and a SBE$_{6.6}$-β-CD concentration of 150 mg/mL. Tartaric acid was added to water until dissolved, and the SBE$_{6.6}$-β-CD was then added to the tartaric acid solution. The API was then added to the solutions, and dissolved within about 10 minutes of the additions. The mixture was stirred about 1 hour, heated treated, and then filtered through a sterile filter. This process was performed using the following lots of SBE$_{6.6}$-β-CD, some of which underwent a single treatment with activated carbon and others that underwent two treatments with activated carbon (SBE$_{6.6}$-β-CD Lot Nos. 17CX01.HQ00021, 17CX01.HQ00025, 17CX01.HQ00029, 17CX01.HQ00035, 17CX01.HQ00036, 17CX01.HQ00037, 17CX01.HQ00038, 17CX01.HQ00039, 17CX01.HQ00040, 17CX01.HQ00041, 17CX01.HQ00042, 17CX01.HQ00043, and 17CX01.HQ00044). Solution samples were placed in a stability chamber at 50° C. for up to 9 weeks. Samples were removed at 4 weeks and again at 9 weeks, and HPLC analysis was performed to determine the extent of API degradation.

Aqueous solution samples were analyzed by UV/vis spectrophotometry using the following procedure. A 30% w/w β-cyclodextrin solution was prepared by dissolving of the above SBE$_{6.6}$-β-CD lots (corrected for water content) in water. The solution was analyzed in a 1 cm cuvette using a PERKIN ELMER Lambda 35 UV/Vis spectrophotometer, scanning from 190 nm to 400 nm at a speed of 240 nm/min and a slit width of 1.0 nm. The samples were blanked against water before analysis. The following tables include the data from this study.

| SBE$_{6.6}$-β-CD Lot Summary and UV Content | | |
|---|---|---|
| 30% SBE$_{6.6}$-β-CD Solutions Lots | # of Carbon Treatments | SAE-CD UV Analysis (Max Abs @ λ = 245-270 nm) |
| 17CX01.HQ00021 | 1 | 0.21 |
| 17CX01.HQ00025 | 1 | 0.44 |
| 17CX01.HQ00029 | 1 | 0.21 |
| 17CX01.HQ00035 | 2 | 0.16 |
| 17CX01.HQ00036 | 2 | 0.14 |
| 17CX01.HQ00037 | 2 | 0.15 |
| 17CX01.HQ00038 | 2 | 0.1 |
| 17CX01.HQ00039 | 2 | 0.09 |
| 17CX01.HQ00040 | 2 | 0.09 |
| 17CX01.HQ00041 | 2 | 0.08 |
| 17CX01.HQ00042 | 2 | 0.07 |
| 17CX01.HQ00043 | 2 | 0.1 |
| 17CX01.HQ00044 | 2 | 0.05 |

| SAE-CD & API Impurity Analysis | | | | | |
|---|---|---|---|---|---|
| SBE$_{6.6}$-β-CD | API Assay | | | | |
| (150 mg/mL) API (7.5 mg/mL) | t = 0 | t = 4 wks @ 50° C. | Δ Assay (t = 0→t = 4 wks) | t = 9 wks @ 50° C. | Δ Assay (t = 0→t = 9 wks) |
| 17CX01.HQ00021 | 0.05 | 0.90 | 0.85 | 1.24 | 1.19 |
| 17CX01.HQ00025 | 0.00 | 1.08 | 1.08 | 1.42 | 1.42 |
| 17CX01.HQ00029 | 0.23 | 1.04 | 0.81 | 1.52 | 1.29 |
| 17CX01.HQ00035 | 0.08 | 0.63 | 0.55 | 0.96 | 0.88 |
| 17CX01.HQ00036 | 0.08 | 0.58 | 0.50 | 0.87 | 0.79 |
| 17CX01.HQ00037 | 0.08 | 0.65 | 0.57 | 0.85 | 0.77 |
| 17CX01.HQ00038 | 0.07 | 0.52 | 0.45 | 0.78 | 0.71 |
| 17CX01.HQ00039 | 0.07 | 0.55 | 0.48 | 0.86 | 0.79 |
| 17CX01.HQ00040 | 0.00 | 0.21 | 0.21 | 0.53 | 0.53 |
| 17CX01.HQ00041 | 0.00 | 0.27 | 0.27 | 0.51 | 0.51 |
| 17CX01.HQ00042 | 0.00 | 0.34 | 0.34 | 0.64 | 0.64 |

-continued

| SBE$_{6.6}$-β-CD | | SAE-CD & API Impurity Analysis | | | |
|---|---|---|---|---|---|
| | | | API Assay | | |
| (150 mg/mL) API (7.5 mg/mL) | t = 0 | t = 4 wks @ 50° C. | Δ Assay (t = 0→t = 4 wks) | t = 9 wks @ 50° C. | Δ Assay (t = 0→t = 9 wks) |
| 17CX01.HQ00043 | 0.07 | 0.61 | 0.54 | 1.00 | 0.93 |
| 17CX01.HQ00044 | 0.00 | 0.13 | 0.13 | 0.35 | 0.35 |

The data show that the API undergoes significantly higher degradation when it is formulated with an SBE$_{6.6}$-β-CD lot that has undergone only a single treatment with activated carbon. The API formulation that contained SBE$_{6.6}$-β-CD Lot No. 17CX01.HQ00025 had the highest UV-active impurity levels (Max. Abs.=0.44 A.U.) and the API underwent a total degradation of 1.42% after 9 weeks. SBE$_{6.6}$-β-CD lots that underwent two treatments with activated carbon were measurably lower in terms of both levels of UV-active impurities and the extent of API degradation. The extent of API degradation that occurred during storage for 9 weeks at 50° C. correlated with the concentration of UV-active impurities present in the formulations. For example, the API formulation containing SBE$_{6.6}$-β-CD Lot No. 17CX01.HQ00044 (which contained UV-active impurities having a Max. Abs.=0.05 AU.) underwent a total degradation of only 0.35% after 9 weeks at 50° C.

Figure 5:
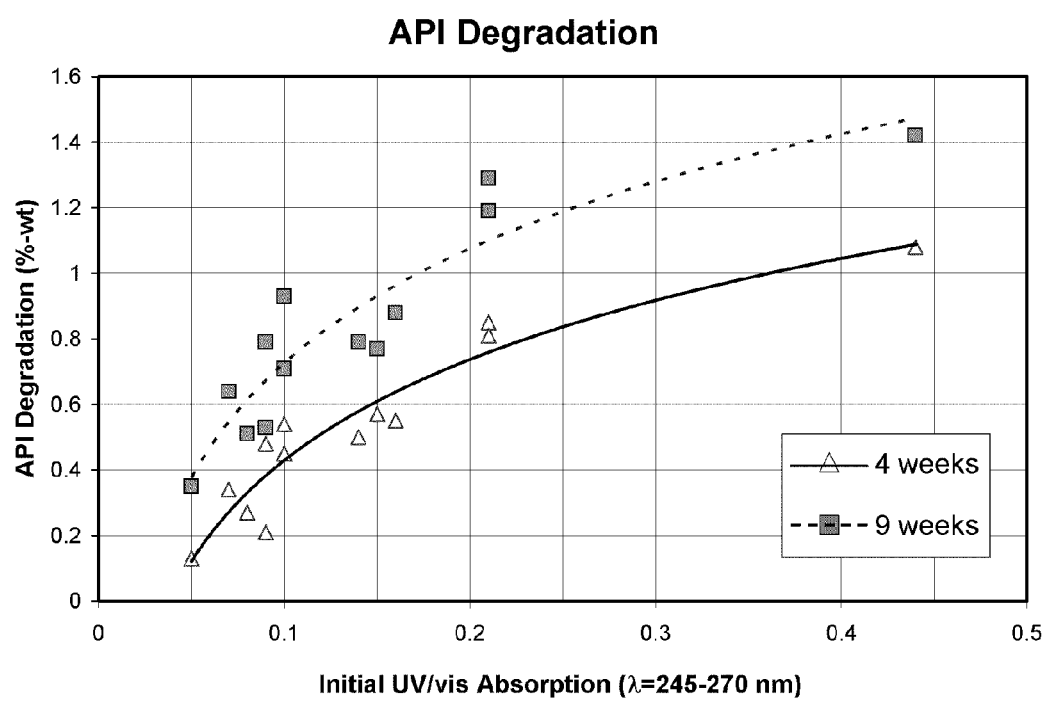
FIG. 5 provides a graphic representation of the effect of initial UV/Vis absorption of a $SBE_{6.6}$-β-CD solution on API stability.

FIG. 5 provides a graphical representation of the correlation between the initial UV/vis absorption of the SBE$_{6.6}$-β-CD lots at a wavelength of 245 nm to 270 nm, and the extent of API degradation determined at 4 weeks and 9 weeks. Referring to FIG. 5, the data shows that at both 4 weeks ( —△— ) and 9 weeks ( - -■- - ), the extent of the API degradation increases with the concentration of the UV/vis absorbing drug-degrading impurities present in the SBE$_{6.6}$-β-CD composition.

Example 16

Measurement of Impurities by Processing

The SBE$_{6.6}$-β-CD samples after reaction workup (Example 5), after ultrafiltration (Example 6), after the second carbon column (Example 7), after concentration (Example 8), and as a final product were separated, identified, and quantified using a Shimadzu Prominence 20A HPLC instrument and a ZIC® pHILIC column (150×4.6 mm, 5 μm, 200 A, PEEK Merck SeQuant™ SN 1479) utilizing a Corona (ESA Bioscience) Charged Aerosol Detector. A gradient mobile phase method is performed using a solution of 100 mM ammonium formate (pH adjusted to 4.6), methanol, 2-propanol, and acetonitrile 15/5/20/65 (A) and a solution of 30 mM ammonium formate (pH adjusted to 4.6), methanol, 2-propanol, and acetonitrile 65/5/20/10 (B). A sample solution of Captisol® is prepared at a concentration of approximately 40 mg/mL in HPLC grade acetonitrile/water and analyzed versus a prepared reference solution of known concentration of 4-hydroxybutane-1-sulfonic acid, disodium bis(4-sulfobutyl)ether, chloride, sodium, phosphate, silicon dioxide, and β-cyclodextrin in acetonitrile/water at the impurity specification limit. Validation studies have shown the method to be specific, linear in the impurity specification range, precise, and stable. The gradient used is shown in the following table.

| Time (min) | % B |
|---|---|
| 0 | 20 |
| 15 | 35 |
| 28 | 90 |
| 32 | 90 |
| 36 | 15 |
| 38 | 20 |
| 45 | 20 |

As shown in FIG. 6, after ultrafiltration of the crude SBE$_{6.6}$-β-CD product, impurities such as β-cyclodextrin and 4-hydroxybutane-1-sulfonic acid (4-HBSA) are present. After a second column with activated carbon, the amount of β-cyclodextrin and 4-hydroxybutane-1-sulfonic acid impurities have been reduced. However, as shown in FIG. 6, there are high amounts of chloride present in the product after the two columns.

Example 17

Measurement of Chloride Concentration

The SBE$_{6.6}$-β-CD samples after reaction workup (Example 5), after ultrafiltration (Example 6), after the second carbon column (Example 7), after concentration (Example 8), and as a final product were analyzed using a Corona (ESA Bioscience) Charged Aerosol Detector to determine chloride concentration.

As shown in FIG. 7, after the ultrafiltration, the residual level of chloride drops to approximately zero. After further purification using two columns of activated carbon, chloride is added back into the SBE$_{6.6}$-β-CD solution.

Example 18

Measurement of Chloride Concentration

The SBE$_{6.6}$-β-CD samples after reaction workup (Example 5), after ultrafiltration (Example 6), 5, 10, and 20 minutes after addition to the first activated carbon column, and 5, 10, and 20 minutes after addition to the second activated carbon column were analyzed using a Corona (ESA Bioscience) Charged Aerosol Detector to determine chloride concentration.

As shown in FIG. 8, the chloride impurity level for two SBE$_{6.6}$-β-CD commercial batches is approximately zero after the ultrafiltration and increases substantially after treatment with activated carbon during the first 5 minutes, with the level dropping after 10 and 20 minutes.

Example 19

Purification of Activated Carbon Using a Dedicated Tank System

The activated carbon can be added to a dedicated tank system with an agitator and screen system. The activated carbon can be charged followed by washing with several portions of water at a determined agitation rate for a determined time period. Following the water wash, the water layer can be removed from the dedicated tank and washed with additional water. After additional water washes the conductivity of the eluted water can be determined using ion chromatography (4.0×250 mm USP packing L50 or similar with mobile phases of 4 mM sodium bicarbonate in methanol/water (1:9), a flow rate of 1 mL/min, a sample volume of 20 μL, and a run time of 10 min) and when the conductivity is below a predetermined level the carbon can be suspended in water and pumped into carbon housings. The activated carbon would then be ready for addition of the alkylated cyclodextrin solution.

Example 20

Purification of $SBE_{6.6}$-β-CD Using Activated Carbon Having a Determined Conductivity Level A column was charged with 32 kg (about 11-12% wt. (11.8-12% wt.) of the starting amount of β-cyclodextrin) of SHIRASAGI® DC32 granular activated carbon and washed thoroughly with water until the wash samples had a conductivity level less than 10 μS as shown in the following Table. Conductivity was determined using ion chromatography (4.0×250 mm USP packing L50 or similar with mobile phases of 4 mM sodium bicarbonate in methanol/water (1:9), a flow rate of 1 mL/min, a sample volume of 20 μL, and a run time of 10 min).

The ratio of $SBE_{6.6}$-β-CD to activated carbon was about 8.4:1 to 8.5:1 (about 8.44:1). Once washed, the reaction solution was passed (recycled) through the carbon for at least 2 hours to complete a first treatment cycle.

A second column was charged with 32 kg (about 11-12% wt. of the starting amount of β-cyclodextrin) of SHIRASAGI® DC32 granular activated carbon and washed thoroughly with water until the wash samples had a conductivity level less than 10 μS (measured by ion chromatography (4.0×250 mm USP packing L50 or similar with mobile phases of 4 mM sodium bicarbonate in methanol/water (1:9), a flow rate of 1 mL/min, a sample volume of 20 μL, and a run time of 10 min)) as shown in the following Table. Once washed, the reaction solution was passed through the carbon for at least 2 hours to complete a second treatment cycle.

After the second treatment cycle, the $SBE_{6.6}$-β-CD was analyzed using a Corona (ESA Bioscience) Charged Aerosol Detector to determine chloride concentration.

Figure 10:
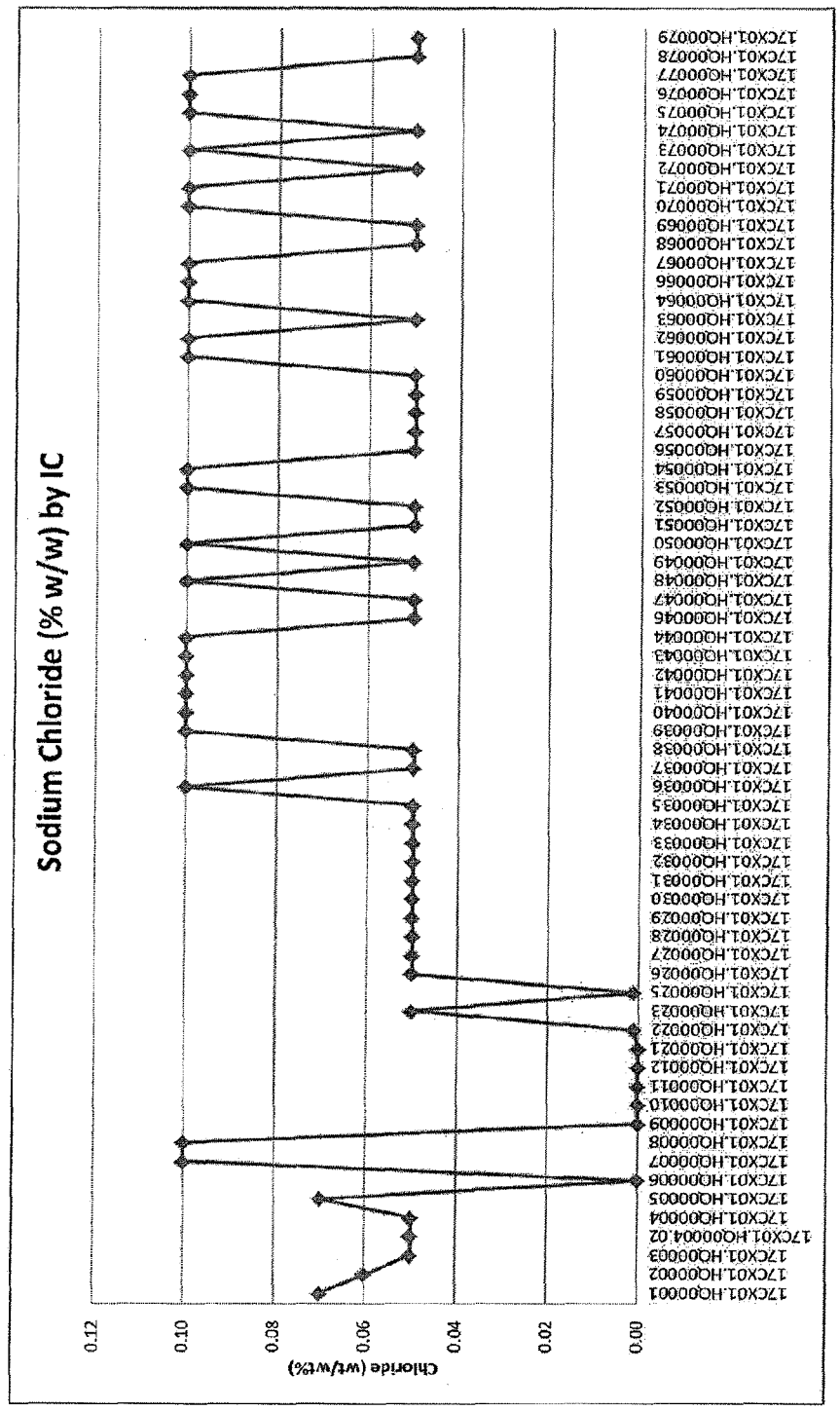
FIG. 10 provides a graphic representation of the sodium chloride concentration (w/w) of $SBE_{6.6}$-β-CD samples after (a) one activated carbon treatment cycle (Batch Nos. 17CX01.HQ00001-17CX001.HQ00003, 17CX01.HQ00004.02, and 17CX01.HQ00005-17CX01.HQ00034) and (b) two activated carbon treatment cycles (Batch Nos. 17CX01.HQ00035-17CX01.HQ00079) measured using ion chromatography. The limit of detection for the ion chromatograph is 0.05% by weight of chloride.

As shown in the Table, all of the samples had a chloride content of 0.07% or less with 6 of the 9 samples having a chloride content of less than 0.05% (the limit of detection for the ion chromatograph). This is an improvement over measurements using the previous method shown in FIG. 10 which had only a 65% success rate (44 out of 68 samples) in obtaining chloride levels of less than 0.10%. This is also a significant improvement over the previous method for samples than had been passed through two activated carbon treatment cycles as shown in FIG. 10 which had only a 48% success rate (20 out of 42 samples) in obtaining chloride levels of less than 0.1%.

| $SBE_{6.6}$-β-CD Lot No. | Chloride Content (w/w) | Column 1 conductivity (μs) | Column 2 conductivity (μs) | Average conductivity (μs) |
|---|---|---|---|---|
| 17CX01.HQ00080 | 0.07 | 10.00 | 10.00 | 10.00 |
| 17CX01.HQ00081 | 0.06 | 9.90 | 6.10 | 8.00 |
| 17CX01.HQ00082 | <0.05 | 6.92 | 8.87 | 7.90 |
| 17CX01.HQ00083 | <0.05 | 8.91 | 8.16 | 8.54 |
| 17CX01.HQ00084 | <0.05 | 9.35 | 8.68 | 9.02 |
| 17CX01.HQ00085 | <0.05 | 8.53 | 8.95 | 8.74 |
| 17CX01.HQ00086 | <0.05 | 6.92 | 8.10 | 7.51 |
| 17CX01.HQ00087 | <0.05 | 8.32 | 8.46 | 8.39 |
| 17CX01.HQ00088 | 0.07 | 10.00 | 10.00 | 10.00 |

Example 21

Purification of Activated Carbon to a Constant Conductivity Level

A column can be charged with 32 kg (about 11-12% wt. (11.8-12% wt.) of the starting amount of alkylated cyclodextrin) of SHIRASAGI® DC32 granular activated carbon and washed thoroughly with water until the wash samples have a constant conductivity. Following the water washes, an alkylated cyclodextrin solution portion can be added to the housing and passed through the carbon for a determined time period before discarding. A further alkylated cyclodextrin solution can be added to the housing and passed through the carbon for at least 2 hours to complete the first treatment cycle.

A second column can be charged with 32 kg (about 11-12% wt. (11.8-12% wt.) of the starting amount of alkylated cyclodextrin) of SHIRASAGI® DC32 granular activated carbon and washed thoroughly with water until the wash samples have a constant conductivity. Following the water washes, an alkylated cyclodextrin solution portion can be added to the housing and passed through the carbon for a determined time period before discarding. A further alkylated cyclodextrin solution can be added to the housing and passed through the carbon for at least 2 hours to complete the first treatment cycle.

CONCLUSION

These examples illustrate possible embodiments of the present invention. While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections can set forth one or more, but not all exemplary embodiments of the present invention as contemplated by the inventor(s), and thus, are not intended to limit the present invention and the appended claims in any way.

All of the various aspects, embodiments, and options described herein can be combined in any and all variations.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A process for preparing an alkylated cyclodextrin composition comprising an alkylated cyclodextrin, the process comprising:
(a) mixing a cyclodextrin with an alkylating agent to form a reaction milieu comprising an alkylated cyclodextrin, one or more unwanted components, and one or more drug-degrading impurities;
(b) conducting one or more separations to remove the one or more unwanted components from the reaction milieu to form a partially purified solution comprising the alkylated cyclodextrin and the one or more drug-degrading impurities, wherein the one or more separations are ultrafiltration, diafiltration, centrifugation, extraction, solvent precipitation, or dialysis; and
(c) treating the partially purified solution with a phosphate-free activated carbon having a residual conductivity of 10 μS or less and producing the alkylated cyclodextrin.

2. The process of claim 1, wherein the alkylated cyclodextrin composition further comprises less than 500 ppm of a phosphate.

3. The process of claim 1, wherein the alkylated cyclodextrin composition further comprises less than 125 ppm of a phosphate.

4. The process of claim 1, wherein the residual conductivity in (c) is 9 μS or less.

5. The process of claim 1, wherein the residual conductivity in (c) is 8 μS or less.

6. The process of claim 1, wherein the alkylated cyclodextrin composition further comprises less than 0.5% (w/w) of a chloride.

7. The process of claim 1, wherein the alkylated cyclodextrin composition further comprises 0.1% (w/w) of a chloride.

8. The process of claim 1, wherein the alkylated cyclodextrin composition further comprises 0.05% (w/w) or less of a chloride.

9. The process of claim 1, wherein the alkylated cyclodextrin composition has an average degree of substitution of 2 to 9.

10. The process of claim 1, wherein the alkylated cyclodextrin composition has an average degree of substitution of 4.5 to 7.5.

11. The process of claim 1, wherein the alkylated cyclodextrin composition has an average degree of substitution of 6 to 7.5.

12. The process of claim 1, wherein the alkylated cyclodextrin composition has an absorption of less than 1 A.U., as determined by UV/vis spectrophotometry at a wavelength of 245 nm to 270 nm for an aqueous solution containing 300 mg of the alkylated cyclodextrin composition per mL of solution in a cell having a 1 cm path length.

13. The process of claim 1, wherein the alkylated cyclodextrin composition has an absorption of less than 0.5 A.U., as determined by UV/vis spectrophotometry at a wavelength of 245 nm to 270 nm for an aqueous solution containing 300 mg of the alkylated cyclodextrin composition per mL of solution in a cell having a 1 cm path length.

14. The process of claim 12, wherein the absorption is due to a drug degrading agent.

15. The process of claim 1, wherein the alkylated cyclodextrin composition has an absorption of less than 1 A.U., as determined by UV/vis spectrophotometry at a wavelength of 245 nm to 270 nm for an aqueous solution containing 500 mg of the alkylated cyclodextrin composition per mL of solution in a cell having a 1 cm path length.

16. The process of claim 1, wherein the alkylated cyclodextrin composition has an absorption of less than 1 A.U., as determined by UV/vis spectrophotometry at a wavelength of 320 nm to 350 nm for an aqueous solution containing 300 mg of the alkylated cyclodextrin composition per mL of solution in a cell having a 1 cm path length.

17. The process of claim 1, wherein the alkylated cyclodextrin composition has an absorption of less than 0.5 A.U., as determined by UV/vis spectrophotometry at a wavelength of 320 nm to 350 nm for an aqueous solution containing 300 mg of the alkylated cyclodextrin composition per mL of solution in a cell having a 1 cm path length.

18. The process of claim 16, wherein the absorption is due to a color forming agent.

19. The process of claim 1, wherein the alkylated cyclodextrin composition has an absorption of less than 1 A.U., as determined by UV/vis spectrophotometry at a wavelength of 320 nm to 350 nm for an aqueous solution containing 500 mg of the alkylated cyclodextrin composition per mL of solution in a cell having a 1 cm path length.

20. The process of claim 1, wherein the phosphate-free activated carbon is washed with a solvent until the eluted solvent has reached the residual conductivity in (c).

21. The process of claim 1, wherein the phosphate-free activated carbon is washed with water until the eluted water has reached the residual conductivity in (c).

22. The process of claim 1, wherein the alkylated cyclodextrin is a sulfoalkyl ether cyclodextrin of Formula (II):

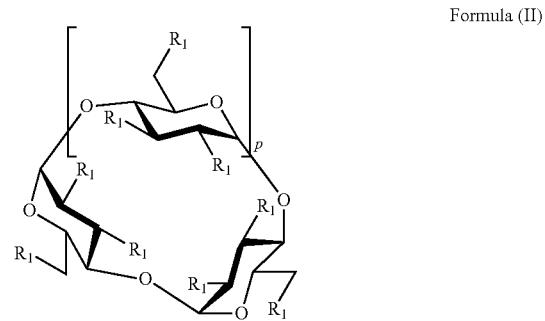

Formula (II)

wherein p is 4, 5, or 6, and $R_1$ is independently selected at each occurrence from —OH or —O—($C_2$-$C_6$ alkylene)-$SO_3^-$-T, wherein T is independently selected at each occurrence from pharmaceutically acceptable cations, provided that at least one $R_1$ is —OH and at least one $R_1$ is O—($C_2$-$C_6$ alkylene)-$SO_3^-$-T.

23. The process of claim 22, wherein $R_1$ is independently selected at each occurrence from —OH or —O—($C_4$ alkylene)-$SO_3^-$-T, and -T is $Na^+$ at each occurrence.

24. The process of claim 1, further comprising combining the alkylated cyclodextrin composition with one or more excipients.

25. The process of claim 1, further comprising combining the alkylated cyclodextrin composition with an active agent.

26. A product prepared by the process of claim 1.

27. An alkylated cyclodextrin composition, comprising:
an alkylated cyclodextrin having an average degree of substitution of 2 to 9;
less than 500 ppm of a phosphate; and
0.07% (w/w) or less of a chloride;
wherein the alkylated cyclodextrin composition has an absorption of less than 1 A.U., as determined by UV/vis spectrophotometry at a wavelength of 245 nm to 270 nm for an aqueous solution containing 300 mg of the alkylated cyclodextrin composition per mL of solution in a cell having a 1 cm path length.

28. The alkylated cyclodextrin composition of claim 27, wherein the alkylated cyclodextrin composition has an absorption of 0.5 A.U. or less as determined by UV/vis spectrophotometry at a wavelength of 245 nm to 270 nm for an aqueous solution containing 300 mg of the alkylated cyclodextrin composition per mL of solution in a cell having a 1 cm path length.

29. The alkylated cyclodextrin composition of claim 27, wherein the alkylated cyclodextrin composition has an absorption of 0.2 A.U. or less as determined by UV/vis spectrophotometry at a wavelength of 245 nm to 270 nm for an aqueous solution containing 300 mg of the alkylated cyclodextrin composition per mL of solution in a cell having a 1 cm path length.

30. The alkylated cyclodextrin composition of claim 27, wherein the absorption is due to a drug degrading agent.

31. An alkylated cyclodextrin composition comprising:
an alkylated cyclodextrin having an average degree of substitution of 2 to 9;
less than 500 ppm of a phosphate; and
0.07% (w/w) or less of a chloride;
wherein the alkylated cyclodextrin composition has an absorption of 0.5 A.U. or less as determined by UV/vis spectrophotometry at a wavelength of 245 nm to 270 nm for an aqueous solution containing 500 mg of the alkylated cyclodextrin composition per mL of solution in a cell having a 1 cm path length.

32. The alkylated cyclodextrin composition of claim 27, wherein the average degree of substitution is 6 to 7.5.

33. The alkylated cyclodextrin composition of claim 27 wherein the alkylated cyclodextrin is a sulfoalkyl ether cyclodextrin of Formula (II):

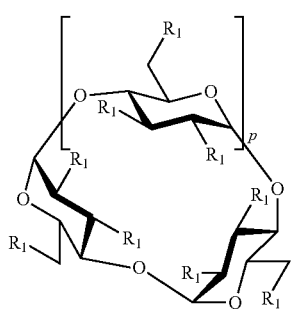

Formula (II)

wherein p is 4, 5, or 6, and $R_1$ is independently selected at each occurrence from —OH or —O—($C_2$-$C_6$ alkylene)-$SO_3^-$-T, wherein T is independently selected at each occurrence from pharmaceutically acceptable cations, provided that at least one $R_1$ is —OH and at least one $R_1$ is O—($C_2$-$C_6$ alkylene)-$SO_3^-$-T.

34. The alkylated cyclodextrin composition of claim 33, wherein $R_1$ is independently selected at each occurrence from —OH or —O—($C_4$ alkylene)-$SO_3^-$-T, and -T is $Na^+$ at each occurrence.

35. The alkylated cyclodextrin composition of claim 27, wherein the alkylated cyclodextrin is a sulfobutyl ether cyclodextrin.

36. An alkylated cyclodextrin composition, comprising:
an alkylated cyclodextrin having an average degree of substitution of 2 to 9;
less than 500 ppm of a phosphate; and
0.07% (w/w) or less of a chloride;
wherein the alkylated cyclodextrin composition has an absorption of less than 1 A.U., as determined by UV/vis spectrophotometry at a wavelength of 320 nm to 350 nm for an aqueous solution containing 300 mg of the alkylated cyclodextrin composition per mL of solution in a cell having a 1 cm path length.

37. The alkylated cyclodextrin composition of claim 36, wherein the alkylated cyclodextrin composition has an absorption of 0.5 A.U. or less as determined by UV/vis spectrophotometry at a wavelength of 320 nm to 350 nm for an aqueous solution containing 300 mg of the alkylated cyclodextrin composition per mL of solution in a cell having a 1 cm path length.

38. The alkylated cyclodextrin composition of claim 36 wherein the alkylated cyclodextrin composition has an absorption of 0.2 A.U. or less as determined by UV/vis spectrophotometry at a wavelength of 245 nm to 270 nm for an aqueous solution containing 300 mg of the alkylated cyclodextrin composition per mL of solution in a cell having a 1 cm path length.

39. The alkylated cyclodextrin composition of claim 36, wherein the absorption is due to a color forming agent.

40. An alkylated cyclodextrin composition comprising:
an alkylated cyclodextrin having an average degree of substitution of 2 to 9;
less than 500 ppm of a phosphate; and
0.07% (w/w) or less of a chloride;
wherein the alkylated cyclodextrin composition has an absorption of 0.5 A.U. or less as determined by UV/vis spectrophotometry at a wavelength of 320 nm to 350 nm for an aqueous solution containing 500 mg of the alkylated cyclodextrin composition per mL of solution in a cell having a 1 cm path length.

41. The alkylated cyclodextrin composition of claim 36, wherein the average degree of substitution is 6 to 7.5.

42. The alkylated cyclodextrin composition of claim 36, wherein the alkylated cyclodextrin is a sulfoalkyl ether cyclodextrin of Formula (II):

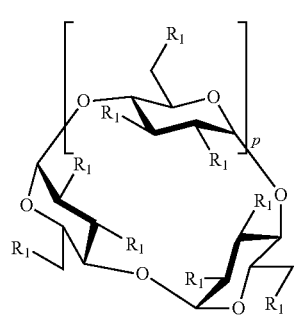

Formula (II)

wherein p is 4, 5, or 6, and $R_1$ is independently selected at each occurrence from —OH or —O—($C_2$-$C_6$ alkylene)-$SO_3^-$-T, wherein T is independently selected at each occurrence from pharmaceutically acceptable cations, provided that at least one $R_1$ is —OH and at least one $R_1$ is O—($C_2$-$C_6$ alkylene)-$SO_3^-$-T.

43. The alkylated cyclodextrin composition of claim 42, wherein $R_1$ is independently selected at each occurrence from —OH or —O—($C_4$ alkylene)-$SO_3^-$-T, and -T is $Na^+$ at each occurrence.

44. The alkylated cyclodextrin composition of claim 36, wherein the alkylated cyclodextrin is a sulfobutyl ether cyclodextrin.

45. A pharmaceutical composition, comprising the alkylated cyclodextrin composition of claim 27 and an active pharmaceutical agent.

46. The pharmaceutical composition of claim 45, wherein the active pharmaceutical agent is a chloride sensitive active agent selecting from the group consisting of bortezomib, disulfiram, epigallocatchin-3-gallate, salinosporamide A, and carfilzomib.

47. The pharmaceutical composition of claim 46, wherein the chloride sensitive active agent is carfilzomib.

48. The process of claim 25, wherein active agent is a chloride sensitive active agent selecting from the group consisting of bortezomib, disulfiram, epigallocatchin-3-gallate, salinosporamide A, and carfilzomib.

49. The process of claim 48, wherein the chloride sensitive active agent is carfilzomib.

50. The process of claim 1, wherein the alkylated cyclodextrin composition further comprises less than 200 ppm of a phosphate.

51. The process of claim 1, wherein the alkylated cyclodextrin composition further comprises 0.07% (w/w) or less of a chloride.

52. The process of claim 1, wherein the alkylated cyclodextrin composition has no detectable levels of a chloride as determined by charged aerosol detection.

53. The composition of claim 27, wherein the alkylated cyclodextrin composition further comprises less than 200 ppm of a phosphate.

54. The composition of claim 27, wherein the alkylated cyclodextrin composition comprises 0.05% (w/w) or less of a chloride.

55. The composition of claim 27, wherein the alkylated cyclodextrin composition has no detectable levels of a chloride as determined by charged aerosol detection.

56. The composition of claim 31, wherein the alkylated cyclodextrin composition further comprises less than 200 ppm of a phosphate.

57. The composition of claim 31, wherein the alkylated cyclodextrin composition comprises 0.05% (w/w) or less of a chloride.

58. The composition of claim 31, wherein the alkylated cyclodextrin composition has no detectable levels of a chloride as determined by charged aerosol detection.

59. The composition of claim 36, wherein the alkylated cyclodextrin composition further comprises less than 200 ppm of a phosphate.

60. The composition of claim 36, wherein the alkylated cyclodextrin composition comprises 0.05% (w/w) or less of a chloride.

61. The composition of claim 36, wherein the alkylated cyclodextrin composition has no detectable levels of a chloride as determined by charged aerosol detection.

62. The composition of claim 40, wherein the alkylated cyclodextrin composition further comprises less than 200 ppm of a phosphate.

63. The composition of claim 40, wherein the alkylated cyclodextrin composition comprises 0.05% (w/w) or less of a chloride.

64. The composition of claim 40, wherein the alkylated cyclodextrin composition has no detectable levels of a chloride as determined by charged aerosol detection.

* * * * *